(12) United States Patent
Leusen et al.

(10) Patent No.: US 11,414,495 B2
(45) Date of Patent: Aug. 16, 2022

(54) CD20 ANTIBODIES

(71) Applicant: Tiga TX, Inc., Westerly, RI (US)

(72) Inventors: Jeannette Henrica Wilhelmina Leusen, Utrecht (NL); Peter Boross, Utrecht (NL); Johannes Hendrik Marco Jansen, Utrecht (NL); Saskia Meyer, Utrecht (NL)

(73) Assignee: TIGA TX, INC., Westerly, RI (US)

( * ) Notice: Subject to any disclaimer, the term of this patent is extended or adjusted under 35 U.S.C. 154(b) by 0 days.

(21) Appl. No.: 16/329,726

(22) PCT Filed: Sep. 1, 2017

(86) PCT No.: PCT/NL2017/050581
§ 371 (c)(1),
(2) Date: Feb. 28, 2019

(87) PCT Pub. No.: WO2018/044172
PCT Pub. Date: Mar. 8, 2018

(65) Prior Publication Data
US 2019/0263922 A1    Aug. 29, 2019

(30) Foreign Application Priority Data
Sep. 1, 2016  (EP) ..................... 16186850

(51) Int. Cl.
*C07K 16/28* (2006.01)
*A61P 35/00* (2006.01)
*A61K 39/00* (2006.01)

(52) U.S. Cl.
CPC .......... *C07K 16/2887* (2013.01); *A61P 35/00* (2018.01); *A61K 2039/505* (2013.01); *C07K 2317/21* (2013.01); *C07K 2317/24* (2013.01); *C07K 2317/34* (2013.01); *C07K 2317/52* (2013.01); *C07K 2317/56* (2013.01); *C07K 2317/73* (2013.01); *C07K 2317/732* (2013.01); *C07K 2317/734* (2013.01); *C07K 2317/90* (2013.01); *C07K 2317/92* (2013.01)

(58) Field of Classification Search
CPC ............ C07K 16/2887; C07K 2317/21; C07K 2317/73; C07K 2317/732; C07K 2317/734; A61P 35/00; A61K 2039/505
See application file for complete search history.

(56) References Cited

PUBLICATIONS

Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Otten et al. "The Fc receptor for IgA (FcalphaRI, CD89)" Immunology Letters 92 (2004) 23-31.
Paiva et al. "FcgammaRlla polymorphism and clinical response to rituximab in non-Hodgkin lymphoma patients" Cancer Genetics and Cytogenetics 183: pp. 35-40 (Feb. 2008).
Polyak et al. "Alanine-170 and proline-172 are critical determinants for extracellular CD20 epitopes; heterogeneity in the fine specificity of CD20 monoclonal antibodies is defined by additional requirements imposed by both amino acid sequence and quaternary structure" Blood 99:3256-3262 (May 2002).
Rafiq et al. "Immune complex-mediated antigen presentation induces tumor immunity" J Clin Invest. vol. 110, Issue 1 pp. 71-79 (Jul. 2002).
Rastetter et al. Rituximab: expanding role in therapy for lymphomas and autoimmune diseases. Annu. Rev. Med. 55:477-503 (2004).
Rezvani et al. "Rituximab resistance." Best Pract Res Clin Haematol, vol. 24, Issue 2, pp. 203-216 (Jun. 2011).
Roos et al. "Human IgA activates the complement system via the mannan-binding lectin pathway" J Immunol, vol. 167, Issue 5: pp. 2861-2868 (Sep. 2001).
Rouwendal et al. "A comparison of anti-HER2 IgA and IgG1 in vivo efficacy is facilitated by high N-glycan sialylation of the IgA" mAbs 8:1, 74-86 (Jan. 2016).
Sandhu et al. "Ofatumumab and its role as immunotherapy in chronic lymphocytic leukemia" Haematologica 100:411-414 (2015).
Sehn et al. "Gadolin: Primary results from a phase III study of obinutuzumab plus bendamustine compared with bendamustine alone in patients with rituximab-refractory indolent non-Hodgkin lymphoma" Journal of Clinical Oncology, 2015 ASCO Annual Meeting vol. 33, No. 15_suppl (May 20 Supplement) (2015).
Senior et al. "The influences of hinge length and composition on the susceptibility of human IgA to cleavage by diverse bacterial IgA1 proteases" J Immunol 174(12): 7792-7799 (Jun. 2005).
Slootstra et al. "Structural aspects of antibody-antigen interaction revealed through small random peptide libraries" Mol. Divers. 1:87-96 (Feb. 1996).
Small et al. "Analysis of innate and acquired resistance to anti-CD20 antibodies in malignant and nonmalignant B cells" PeerJ 1: e31 (Feb. 2013).
Stanglmaier et al. "Rituximab and alemtuzumab induce a nonclassic, caspase-independent apoptotic pathway in B- lymphoid cell lines and in chronic lymphocytic leukemia cells" Ann. Hematol. 83:634-645 (Aug. 2004).
Teeling et al. "Characterization of new human CD20 monoclonal antibodies with potent cytolytic activity against non-Hodgkin lymphomas" Blood 104:1793-1800 (Sep. 2004).

(Continued)

*Primary Examiner* — Sharon X Wen
(74) *Attorney, Agent, or Firm* — Greenberg Traurig, LLP

(57) ABSTRACT

CD20 antibodies with improved characteristics. Some embodiments describe antibodies comprising a mouse IgG2; a human IgG1, IgA1 or IgA2 constant region and a variable domain that can bind the epitope "EPANpSEK" (SEQ ID NO:31) on human CD20 expressed on Ramos cells and which antibody has an increased PCD functionality when compared to Rituximab with a constant region of the same isotype.

11 Claims, 39 Drawing Sheets
Specification includes a Sequence Listing.

(56) References Cited

PUBLICATIONS

Teeling et al. "The biological activity of human CD20 monoclonal antibodies is linked to unique epitopes on CD20" J. Immunol. 177:362-371 (2006).

Timmerman et al. "Rapid and quantitative cyclization of multiple peptide loops onto synthetic scaffolds for structural mimicry of protein surfaces" ChemBioChem. 6:821-824 (2005).

Tipton et al. "Antigenic modulation limits the effector cell mechanisms employed by typ I anti-CD20 monoclonal antibodies" Blood, vol. 125, No. 12, pp. 1901-1909 (Mar. 2015).

Umana et al. "Novel 3rd Generation Humanized Type II CD20 Antibody with Glycoengineered Fc and Modified Elbow Hinge for Enhanced ADCC and Superior Apoptosis Induction" Blood 108 (11): 229 (Nov. 2006).

Van Egmond et al. "Human immunoglobulin A receptor (FcalphaRI, CD89) function in transgenic mice requires both FcR gamma chain and CR3 (CD11b/CD18)" Blood vol. 93, No. 12, pp. 4387-4394 (Jun. 1999).

Vaughan et al. "Inhibitory FcgRIIb (CD32b) becomes activated by therapeutic mAb in both cis and trans and drives internalization according to antibody specificity" Blood (Jan. 2014) vol. 123, No. 5, pp. 669-677.

Weiner "Rituximab: mechanism of action" Semin Hematol 47(2): pp. 115-123 (Apr. 2010).

Weiner et al. "Monoclonal antibodies for cancer immunotherapy" Lancet 373(9668), pp. 1033-1040 (Mar. 2009).

Withoff et al. "Characterization of BIS20x3, a bi-specific antibody activating and retargeting T-cells to CD20-positive B-cells" British Journal of Cancer 84(8), 1115-1121 (2001).

Zhang et al. "FCGR2A and FCGR3A polymorphisms associated with clinical outcome of epidermal growth factor receptor expressing metastatic colorectal cancer patients treated with single-agent cetuximab" J Clin Oncol. vol. 25, No. 24, pp. 3712-3718 (Aug. 2007).

Zhao "Targeting CD47-SIRPa interactions for potentiating therapeutic antibody-mediated tumor cell destruction by phagocytes" University of Amsteram, UvA—Dare (Digital Academic Repository) 2014.

Abes et al. "Long-lasting antitumor protection by anti-CD20 antibody through cellular immune response" Blood vol. 116, No. 6, pp. 926-934 (Aug. 2010).

Badin et al. "Rituximab in the treatment of B-cell non-Hodgkin lymphoma, focus on outcomes and comparative effectiveness" ClinicoEconomics and Outcomes Research, pp. 37-45 (Apr. 2010).

Bakema et al. "Immunoglobulin A: A next generation of therapeutic antibodies?" MAbs 3:4, pp. 352-361 (Jul. 2011).

Beers et al. "Type II (tositumomab) anti-CD20 monoclonal antibody out performs type I (rituximab-like) reagents in B-cell depletion regardless of complement activation" Blood 112:4170-4177 (Nov. 2008).

Beum et al. "Loss of CD20 and bound CD20 antibody from opsonized B cells occurs more rapidly because of trogocytosis-mediated by Fc receptor-expressing effector cells than direct internalization by the B cells" The Journal of Immunology, vol. 187, Issue 6, pp. 3438-3447 (Sep. 2011).

Bologna et al. "Mechanism of action of type II, glycoengineered, anti-CD20 monoclonal antibody GA101 in B-chronic lymphocytic leukemia whole blood assays in comparison with rituximab and alemtuzumab" The Journal of Immunology, vol. 186, pp. 3762-3769 (Feb. 2011).

Bologna et al. "Ofatumumab is more efficient than rituximab in lysing B chronic lymphocytic leukemia cells in whole blood and in combination with chemotherapy" The Journal of Inmmunology, vol. 190, Issue 1, pp. 231-239 (Jan. 2013).

Bornstein et al. "Development of a new fully human anti-CD20 monoclonal antibody for the treatment of B-cell malignancies" Invest. New Drugs 28:561-574 (2010).

Boross et al. "The in vivo mechanism of action of CD20 monoclonal antibodies depends on local tumor burden" Haematologica 96:12, pp. 1822-1830 (Aug. 2011) 28. Esser el al. "Immunoglobulin class switching: molecular and cellular analysis" Annu. Rev. Immunol. 8:717-735 (1990).

Boross et al. "IgA EGFR antibodies mediate tumour killing in vivo" EMBO Mol Med 5: 1213-26 (Jun. 2013).

Boross et al. "Mechanisms of action of CD20 antibodies" Am J Cancer Res 2(6): 676-690 (Nov. 2012).

Chan et al. "CD20-induced lymphoma cell death is independent of both caspases and its redistribution into triton X-100 insoluble membrane rafts" Cancer Res. 63:5480-5489 (Sep. 2003).

Clynes et al. "Inhibitory Fc receptors modulate in vivo cytotoxicity against tumor targets" Nature Medicine, vol. 6, No. 4, pp. 443-446 (Apr. 2000).

Coiffier et al. "Long-term outcome of patients in the LNH-98.5 trial, the first randomized study comparing rituximab-CHOP to standard CHOP chemotherapy in DLBCL patients: a study by the Groupe d'Etudes des Lymphomes de l'Adulte" Blood 116:2040-2045 (May 2010).

Congdon et al. "Antibody Uptake into Neurons Occurs Primarily via Clathrin-dependent Fc? Receptor Endocytosis and Is a Prerequisite for Acute Tau Protein Clearance" J. Biol. Chem. 288:35452-35465 (Dec. 2013).

Cragg et al. "Complement-mediated lysis by anti-CD20 mAb correlates with segregation into lipid rafts" Blood 101:1045-1052 (Feb. 2003).

Dall'ozzo et al. "Rituximab-dependent cytotoxicity by natural killer cells: influence of FCGR3A polymorphism on the concentration-effect relationship" Cancer Research 64, pp. 4664-4669 (Jul. 2004).

Davis et al. "Rituximab anti-CD20 monoclonal antibody therapy in non-Hodgkin's lymphoma: safety and efficacy of re-treatment" J Clin Oncol vol. 18, No. 17, pp. 3135-3143 (Sep. 2000).

De Jong et al. "A Novel Platform for the Potentiation of Therapeutic Antibodies Based on Antigen-Dependent Formation of IgG Hexamers at the Cell Surface" PLOS Biology 14, DOI: 10. 1371/journal.pbio.1002344 (Dec. 2016).

Dechant et al. "Effector mechanisms of recombinant IgA antibodies against epidermal growth factor receptor" The Journal of Immunology, vol. 179, Issue 5, pp. 2936-2943 (Sep. 2007).

Diebolder et al. "Complement is activated by IgG hexamers assembled at the cell surface" Science 343(6176): pp. 1260-1263 (Mar. 2014).

Digaetano et al. "Complement activation determines the therapeutic activity of rituximab in vivo" J. Immunol. 171:1581-1587 (2003).

Du et al. "Structural basis for recognition of CD20 by therapeutic antibody Rituximab" J. Biol. Chem. 282:15073-15080 (May 2007).

Dunkelberger et al. "Complement and its role in innate and adaptive immune responses" Cell Research, vol. 20, pp. 34-50 (2010).

Esser et al. "Immunoglobulin class switching: molecular and cellular analysis" Annu. Rev. Immunol. 8:717-735 (1990) 28. Esser et al. "Immunoglobulin class switching: molecular and cellular analysis" Annu. Rev. Immunol. 8:717-735 (1990).

Geissmann et al. "A subset of human dendritic cells expresses IgA Fc receptor (CD89), which mediates internalization and activation upon cross-linking by IgA complexes" The Journal of Immunology, vol. 166, Issue 1, pp. 346-352 (Jan. 2001).

Glennie et al. "Mechanisms of killing by anti-CD20 monoclonal antibodies" Mol Immunol 44: 3823-3837 (May 2007).

Goede et al. "Obinutuzumab plus chlorambucil in patients with CLL and coexisting conditions" N. Engl. J. Med. 370:1101-1110 (Mar. 2014).

Golay et al. "Mechanism of action of therapeutic monoclonal antibodies: promises and pitfalls of in vitro and in vivo assays" Arch Biochem Biophys 526: pp. 146-153 (Feb. 2012).

Goldenberg et al. "Properties and structure-function relationships of veltuzumab (hA20), a humanized anti-CD20 monoclonal antibody" Blood vol. 113, No. 5, pp. 1062-1070 (Jan. 2009).

Goldenberg et al. "Veltuzumab (humanized anti-CD20 monoclonal antibody): characterization, current clinical results, and future prospects" Leuk. Lymphoma 51:747-755 (May 2010).

Hallek et al. "Addition of rituximab to fludarabine and cyclophosphamide in patients with chronic lymphocytic leukaemia: a randomised, open-label, phase 3 trial" Lancet 376:1164-1174 (Oct. 2010).

(56) References Cited

PUBLICATIONS

Hamre et al. "Expression and modulation of the human immunoglobulin A Fc receptor (CD89) and the FcR gamma chain on myeloid cells in blood and tissue" Scandinavian Journal of Immunology 57: 506-516 (2003).

Heystek et al. "Human immature dendritic cells efficiently bind and take up secretory IgA without the induction of maturation" The Journal of Immunology, vol. 168, Issue 1, pp. 102-107 (Jan. 2002).

Horner et al. "Intimate cell conjugate formation and exchange of membrane lipids precede apoptosis induction in target cells during antibody-dependent, granulocyte-mediated cytotoxicity" The Journal of Immunology, vol. 179, Issue 1, pp. 337-345 (Jul. 2007).

Jones et al. "Rituximab mediates loss of CD19 on B cells in the absence of cell death" Arthritis Rheum vol. 64, No. 10, pp. 3111-3118 (Oct. 2012).

Keating "Rituximab: a review of its use in chronic lymphocytic leukaemia, low-grade or follicular lymphoma and diffuse large B-cell lymphoma" Drugs 70 (11):1445-1476 (2010).

Kiss et al. "Early relapse after rituximab chemoimmunotherapy" Pediatr Blood Cancer 50: pp. 372-375 (2008).

Kocsis et al. "Selective inhibition of the lectin pathway of complement with phage display selected peptides againsl mannose-binding lectin-associated serine protease (MASP)-1 and -2: significant contribution of MASP-1 to lectin pathway activation" The Journal of Immunology, vol. 185, Issue 7, pp. 4169-4178 (Oct. 2010).

Laurenti et al. "New developments in the management of chronic lymphocytic leukemia: role of ofatumumab" Onco Targets Ther. 9:421-429 (Jan. 2016).

Li et al. "Characterization of a rituximab variant with potent antitumor activity against rituximab-resistant B-cell lymphoma" Blood vol. 114, No. 24, pp. 5007-5015 (Dec. 2009).

Lim et al. "Fc gamma receptor IIb on target B cells promotes rituximab internalization and reduces clinical efficacy" Blood (Sep. 2011) vol. 118, No. 9, pp. 2530-2540.

Lim et al. "Anti-CD20 monoclonal antibodies: historical and future perspectives" Haematologica 2010; 95(1), pp. 135-143 (2010).

Lohse et al. "Characterization of a mutated IgA2 antibody of the m(1) allotype against the epidermal growth factor receptor for the recruitment of monocytes and macrophages" The Journal of Biological Chemistry vol. 287, No. 30, pp. 25139-25150, (Jul. 2012).

Mclaughlin et al. "Rituximab chimeric anti-CD20 monoclonal antibody therapy for relapsed indolent lymphoma: half of patients respond to a four-dose treatment program" J Clin Oncol vol. 16, No. 8, pp. 2825-2833 (Aug. 1998).

Meyer et al. "Improved in vivo anti-tumor effects of IgA-Her2 antibodies through half-life extension and serum exposure enhancement by FcRn targeting" MAbs 8:1 pp. 87-98 (Jan. 2016).

Mossner et al. Increasing the efficacy of CD20 antibody therapy through the engineering of a new type II anti-CD20 antibody with enhanced direct and immune effector cell-mediated B-cell cytotoxicity. Blood 115:4393-4402 (Jun. 2010).

Musolino et al. "Immunoglobulin G fragment C receptor polymorphisms and clinical efficacy of trastuzumab-based therapy in patients with HER-2/neu-positive metastatic breast cancer" J Clin Oncol vol. 26, No. 11, pp. 1789-1796 (Apr. 2008).

Niederfellner et al. "Epitope characterization and crystal structure of GA101 provide insights into the molecular basis for type I/II distinction of CD20 antibodies" Blood 118:358-367 (Mar. 2011).

Okroj et al. "Effector mechanisms of anti-CD20 monoclonal antibodies in B cell malignancies" Cancer Treat Rev 39: 632-639 (2013).

Pascal et al., "Anti-CD20 IgA can protect mice against lymphoma development: evaluation of the direct impact of IgA and cytotoxic effector recruitment on CD20 target cells," Haematologica, vol. 97, 2012, pp. 1686-1694.

Klen et al., "Epitope interactions of monoclonal antibodies targeting CD20 and their relationship to functional properties," MAbs. vol. 5, No. 1, 2013, pp. 22-33.

Dechant et al., "Chimeric IgA antibodies against HLA class II effectively trigger lymphoma cell killing," Blood 2002, vol. 100, pp. 4574-4580.

\* cited by examiner

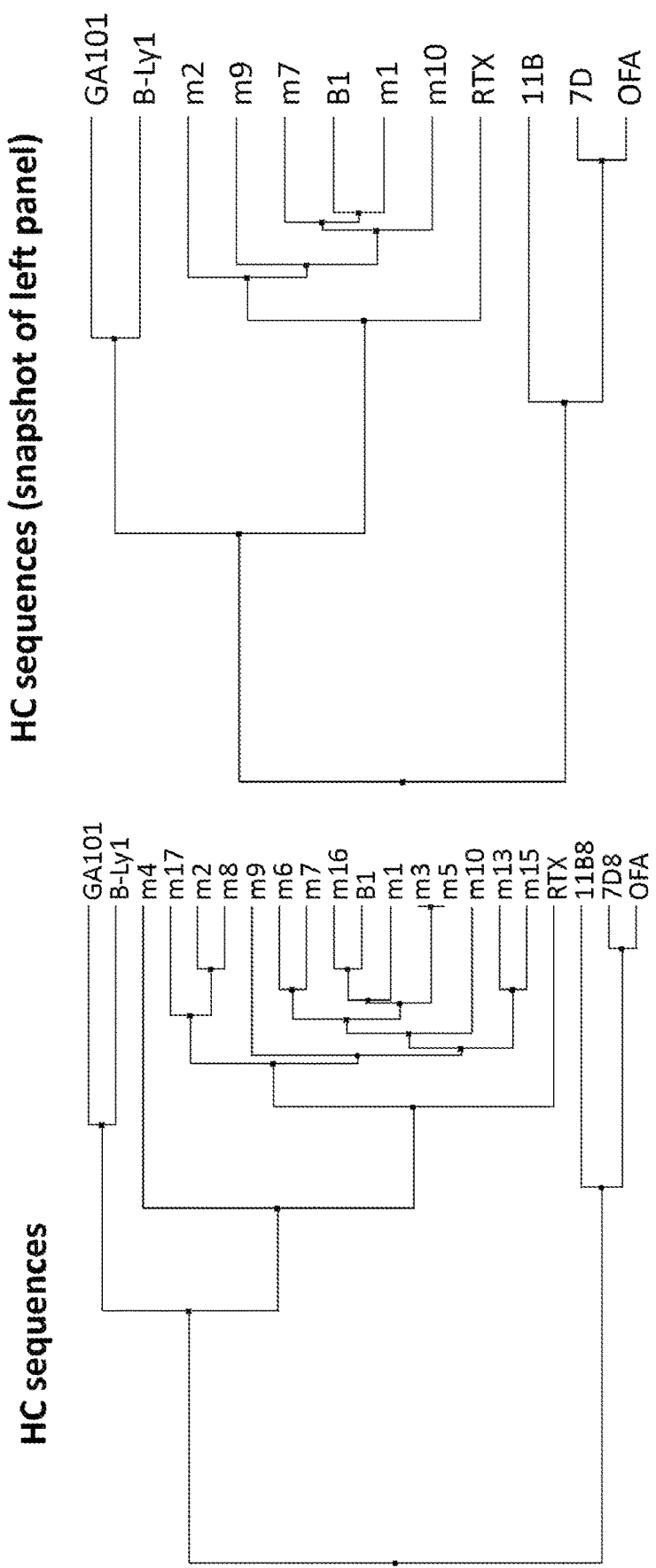
Fig. 1.1

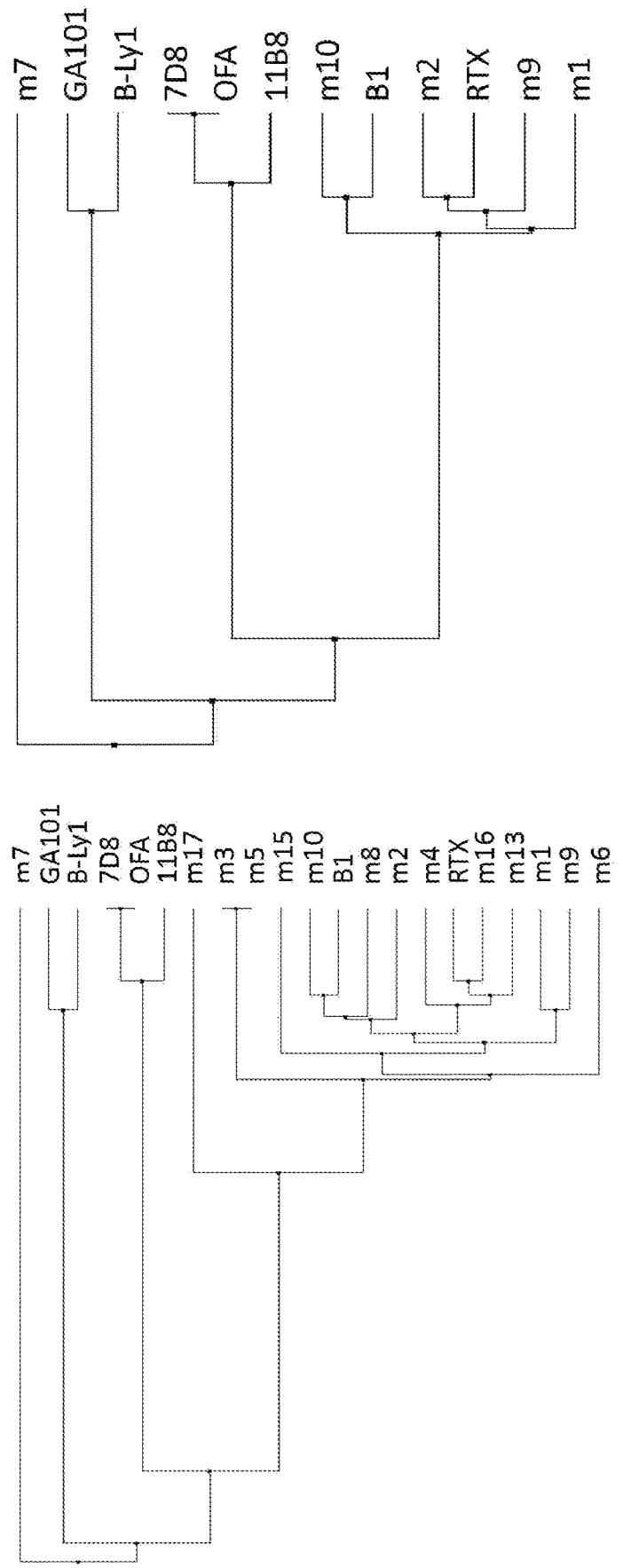
Fig. 1.2

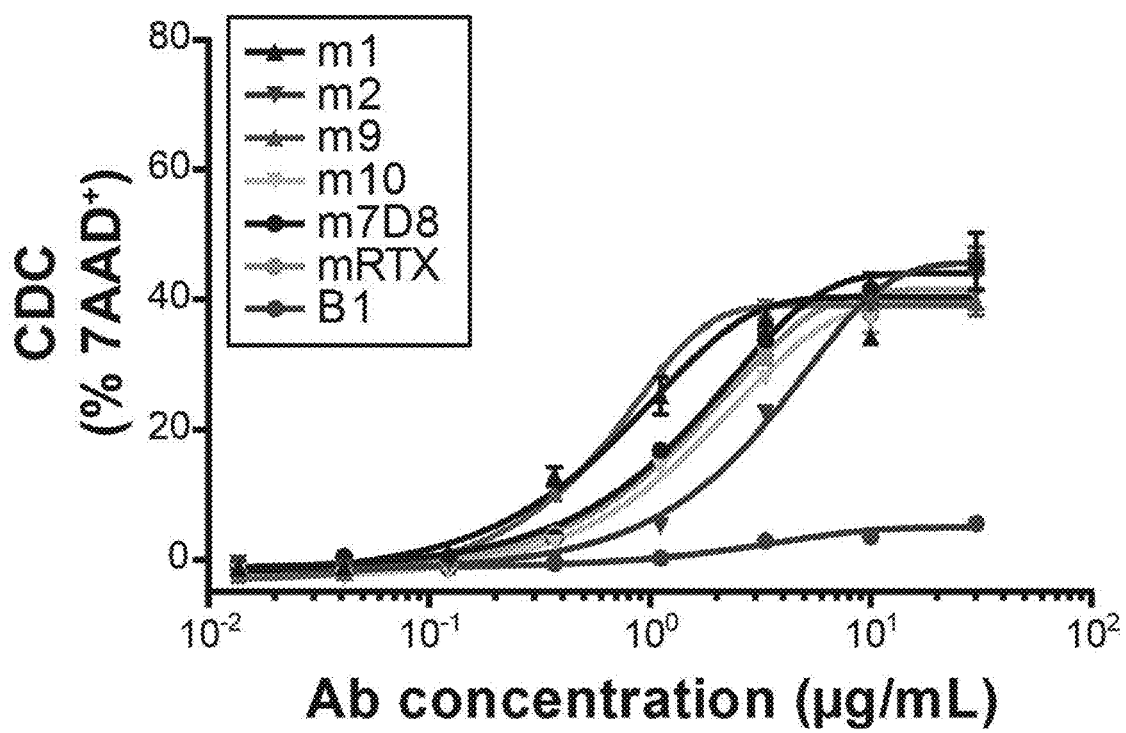

Fig. 4A
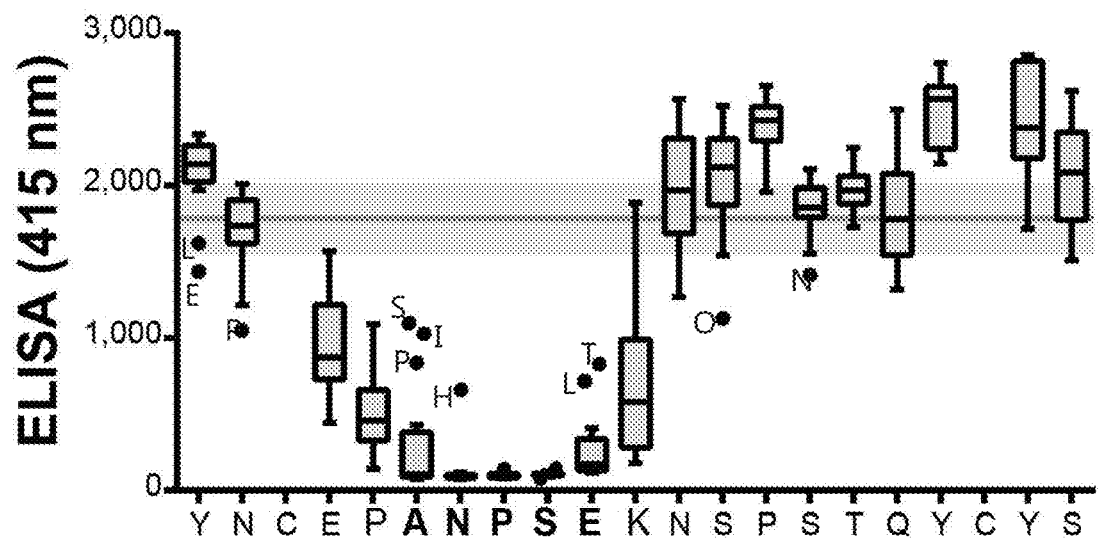
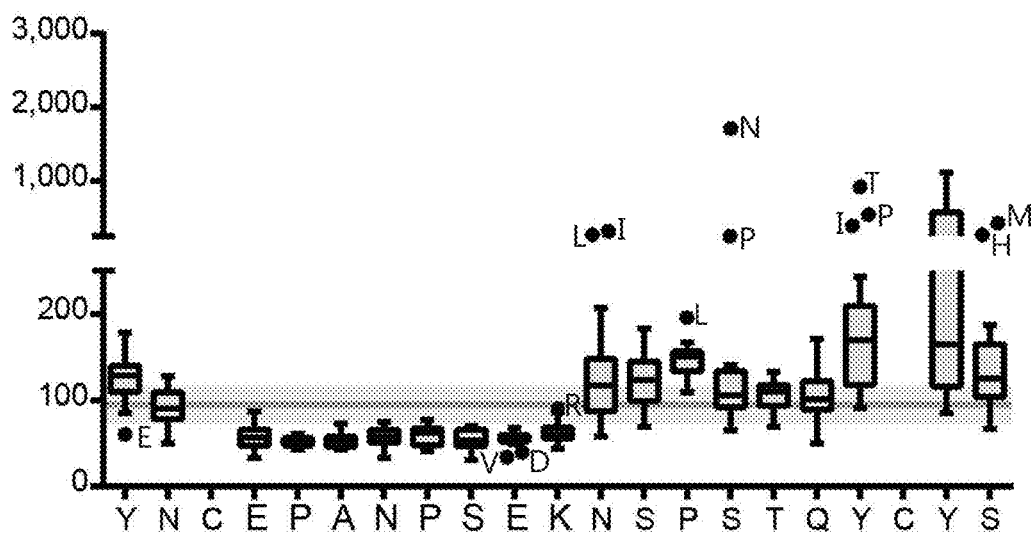

Fig. 4C

| | WT | E168A | A170P | E170S | N171A | N171H | P172A | S173A | E174Y | E174D | K175F | K175R | N176A | S177A |
|---|---|---|---|---|---|---|---|---|---|---|---|---|---|---|
| B1 | 59 | 48 | 38 | 55 | 46 | 58 | 31 | 55 | 51 | 57 | 46 | 53 | 2 | 40 |
| m11B8 | 82 | 83 | 41 | 84 | 100 | 100 | 96 | 98 | 13 | 9 | 94 | 89 | 88 | 79 |
| m7D8 | 77 | 66 | 62 | 60 | 82 | 86 | 69 | 73 | 80 | 67 | 71 | 71 | 67 | 68 |
| mRTX | 77 | 52 | 42 | 60 | 3 | 3 | 25 | 2 | 29 | 52 | 67 | 65 | 65 | 63 |
| m17 | 90 | 78 | 89 | 69 | 5 | 2 | 13 | 47 | 49 | 78 | 82 | 89 | 83 | 81 |
| m7 | 100 | 86 | 83 | 88 | 18 | 2 | 26 | 51 | 100 | 87 | 94 | 95 | 86 | 91 |
| m1 | 98 | 84 | 81 | 85 | 3 | 6 | 42 | 8 | 32 | 79 | 100 | 97 | 95 | 100 |
| m6 | 99 | 92 | 86 | 90 | 17 | 6 | 47 | 91 | 59 | 82 | 88 | 96 | 93 | 96 |
| m5 | 96 | 78 | 74 | 81 | 3 | 12 | 57 | 43 | 57 | 72 | 97 | 91 | 85 | 92 |
| m3 | 97 | 76 | 75 | 80 | 3 | 12 | 58 | 40 | 62 | 73 | 90 | 83 | 76 | 84 |
| m4 | 94 | 77 | 69 | 78 | 10 | 41 | 46 | 10 | 83 | 77 | 80 | 74 | 78 | 83 |
| m10 | 95 | 79 | 90 | 85 | 6 | 19 | 67 | 14 | 59 | 82 | 96 | 96 | 100 | 95 |
| m2 | 94 | 72 | 67 | 72 | 10 | 3 | 78 | 55 | 70 | 75 | 88 | 80 | 78 | 81 |
| m9 | 100 | 100 | 100 | 100 | 78 | 73 | 87 | 100 | 89 | 100 | 100 | 100 | 99 | 95 |
| m11 | 95 | 72 | 85 | 83 | 3 | 70 | 100 | 70 | 61 | 84 | 89 | 91 | 91 | 90 |

Fig. 12B
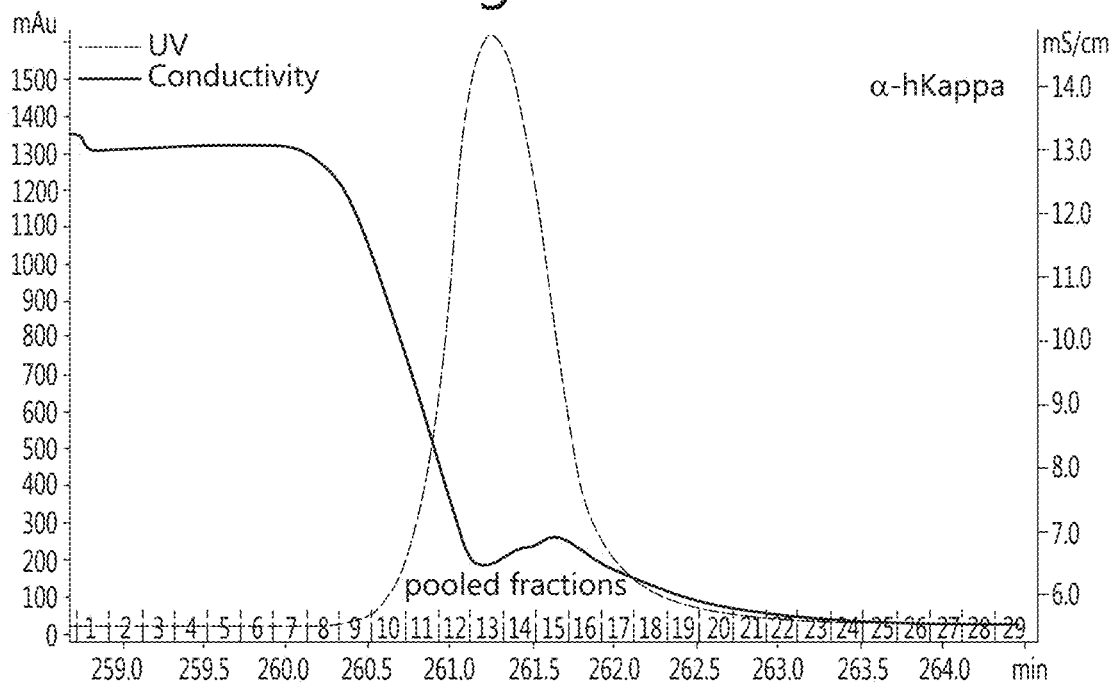
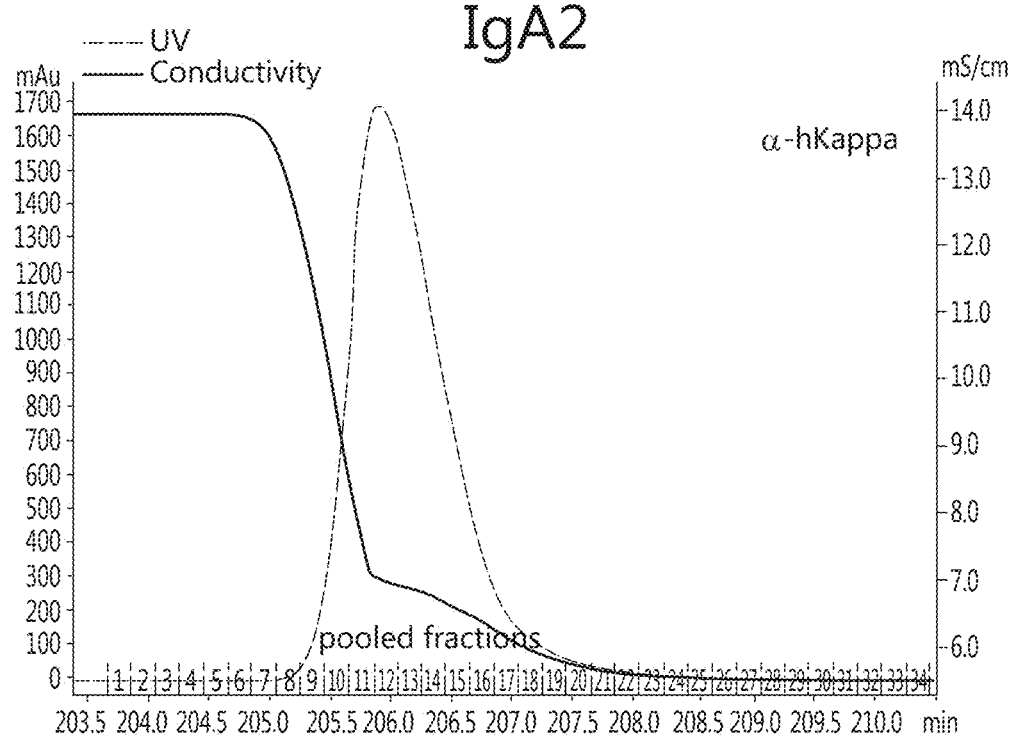

Fig. 12C
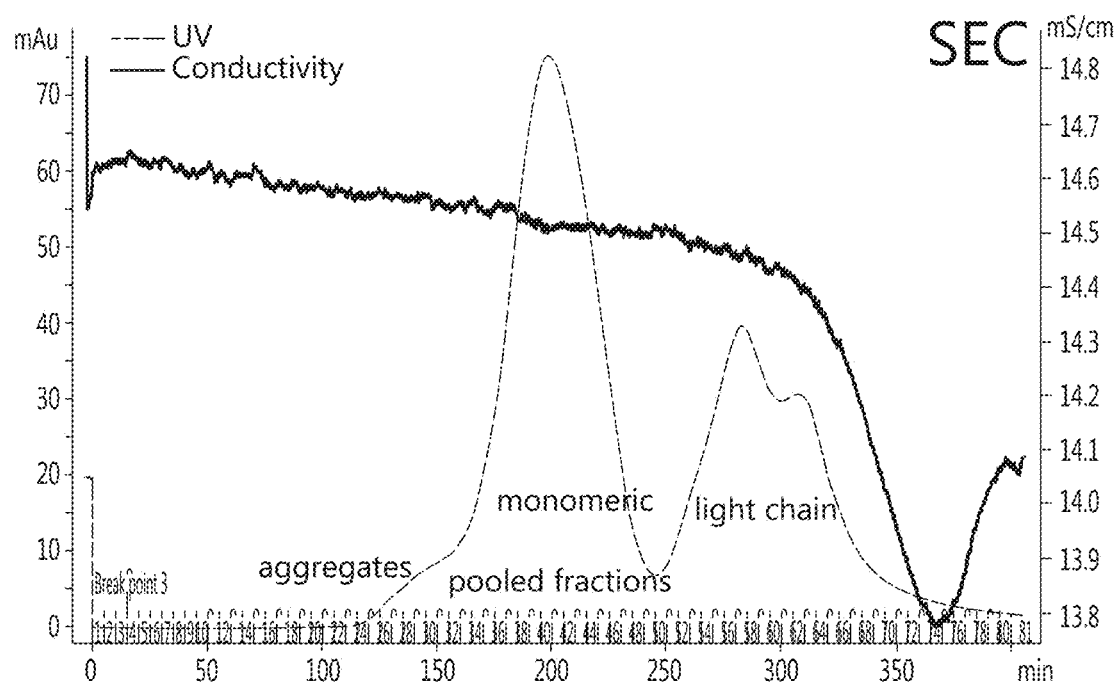
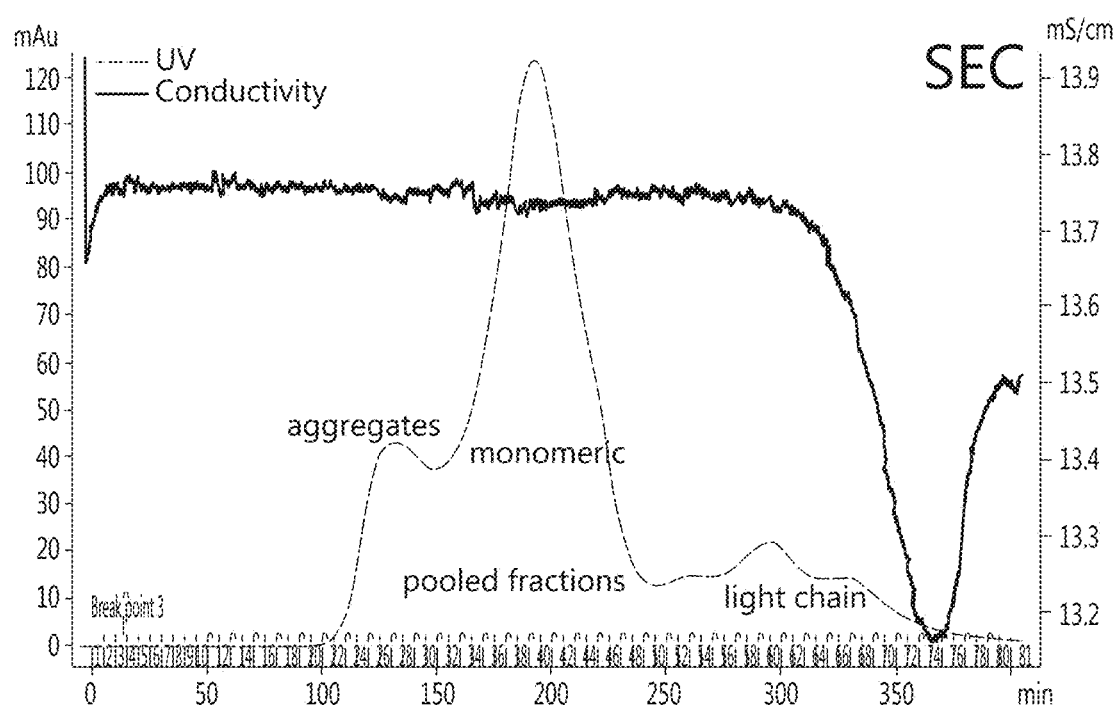

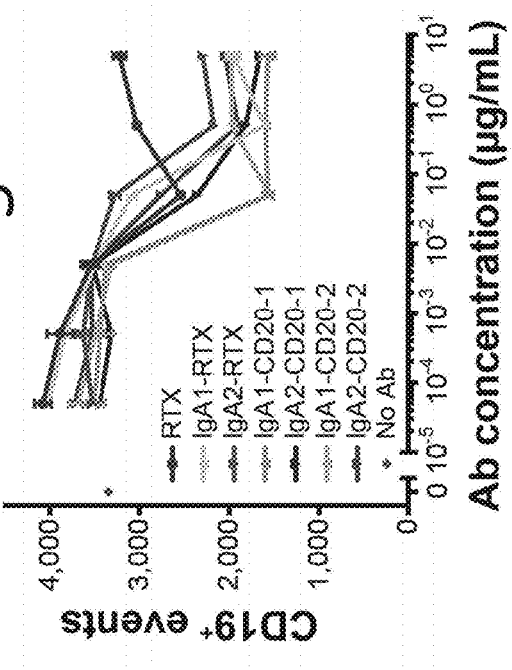
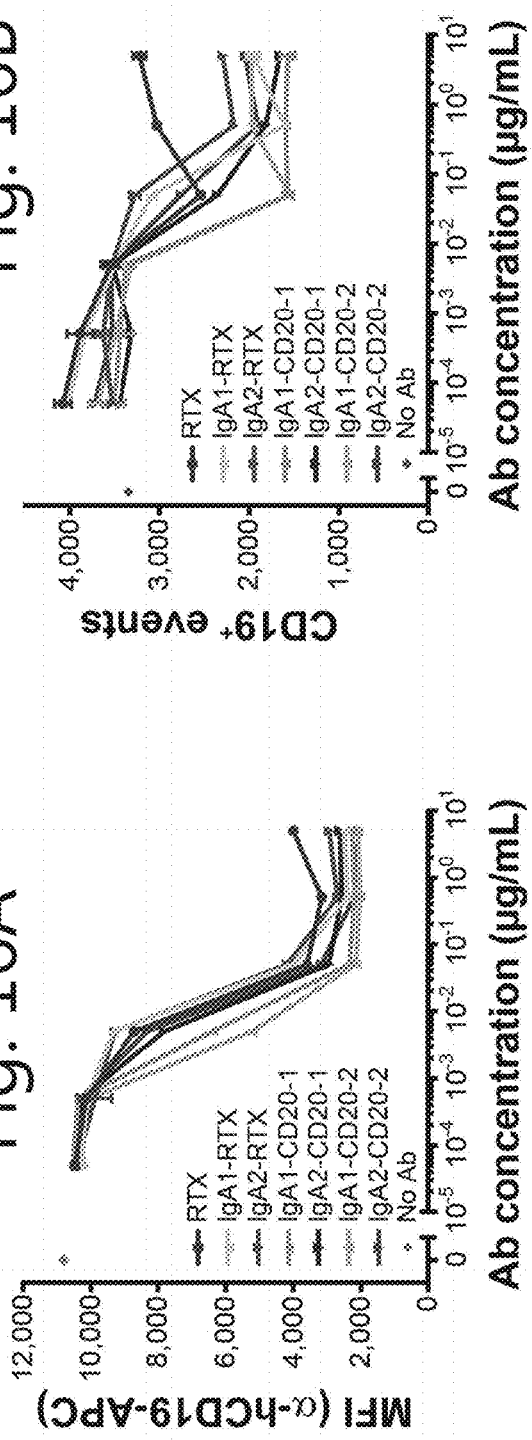
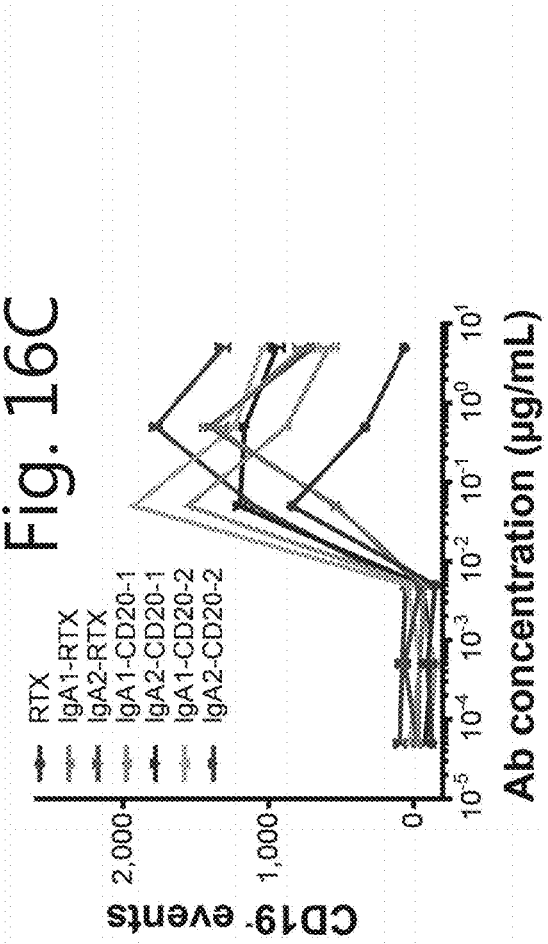

Fig. 18 m1/CD20-1
VH: SEQ ID NO: 1
QAYLQQSGAELVRPGASVKMSCKASGYTFTSYNLHWVKQTPRQGLEWIGAIYPGNGDTSYNQKFKGKATLT
VDKSSSTAYMQLSRLTSEDSAVYFCARSNSYGSTYWYFDVWGTGTTVTVSS
VL: SEQ ID NO: 2
QIVLSQSPAVLFASPGEKVTMTCRARSSVSYMDWYQQKPRSSPKPWIYATSNLASGVPARFSGSGSGTSYS
LTISRVEAEDAATYYCQQWTSNPPTFGSGTKLEIK m2/CD20-2
VH: SEQ ID NO: 7
QAYLQQSGAELVRPGASVKMSCKASGYTFTSYNMHWVKQTPRQGLEWIGGIYPGNGDTSYNQKFKGKATLT
VDKSSSTAYMQLSSLTSEDSAVYFCARYYYGSSYGAMDYWGQGTSVTVSS
VL: SEQ ID NO: 8
QIVLSQSPAILSASPGEKVTMTCRASSSVSYMHWYQQKPGSSPKPWIYATSNLASGVPARFSGSGSGTSYS
LTISRVEAADAATYYCHQWTFNPPTFGGGTKLEIK m7/CD20-7
VH: SEQ ID NO: 9
QAYLQQSGAELVRPGASVKMSCKASGYTFASYNMHWIKQTPRQGLEWIAAIYPGNGDTSYNQKFKGKATLT
VDKSSSTAYMQLSSLTSEDSAVYFCARTYYYGSSPYWSFDVWGTGTTVTVSS
VL: SEQ ID NO: 10
DIQMTQSPASLSASVGETVTVTCGASYNIYGALNWYQRKQGKSPQLLIYGATNLADGMSSRFSGSGSGRQY
SLKISSLHPDDVATYYCQNVLSNPPTFGGGTKLEIK m9/CD20-9
VH: SEQ ID NO: 11
QAYLQQSGAELVRPGASVKMSCKASGYTFPSYNMHWVKQTPRQGLEWIGAIYPGNGDTSYNQKFKGKASQT
VDKSSSTVYMQLSSLTSADSAVYFCARSRLFDSSYGWYFDVWGTGTTVTVSS
VL: SEQ ID NO: 12
QIVLSQSPAILSAYPGEKVTMTCRARSSVSYIDWYQQKAGSSPKPWIYATSNLASGVPARFSGSGSGTSYS
LTISRVEAEDAATYYCQQWTSNPPTFGGGTKLEIK m10/CD20-10
VH: SEQ ID NO: 13
QAYLQQSGADLVRPGASVKMSCKASGFTFPSYNLHWVKQTPRQGLEWIGAIYPGNGDTSYNQKFKGKATLT
VDKSSSTAYMQLSSLTSEDSAVYFCARSAYYGSNVWFFDVWGTGTTVTVSS
VL: SEQ ID NO: 14
QIVLSQSPAILSASPGEKVTMTCRASSSVSYMDWYQQKPGSSPKPWIYATSNLASGVPTRFSGSGSGTSYS
LTISRVEAEDAATYYCQQWISNPPTFGAGTKLDLK

Fig. 24

IgG1 constant region; SEQ ID NO: 3

ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLS
LSPGKStop IgA1 constant region; SEQ ID NO: 4

ASPTSPKVFPLSLCSTQPDGNVVIACLVQGFFPQEPLSVTWSESGQGVTARNFPPSQDASGDLYT
TSSQLTLPATQCLAGKSVTCHVKHYTNPSQDVTVPCPVPSTPPTPSPSTPPTPSPSCCHPRLSLH
RPALEDLLLGSEANLTCTLTGLRDASGVTFTWTPSSGKSAVQGPPDRDLCGCYSVSSVLPGCAEP
WNHGKTFTCTAAYPESKTPLTATLSKSGNTFRPEVHLLPPPSEELALNELVTLTCLARGFSPKDV
LVRWLQGSQELPREKYLTWASRQEPSQGTTTFAVTSILRVAAEDWKKGDTFSCMVGHEALPLAFT
QKTIDRLAGKPTHVNVSVVMAEVDGTCYStop IgA2m1 constant region; SEQ ID NO: 5

ASPTSPKVFPLSLDSTPQDGNVVVACLVQGFFPQEPLSVTWSESGQNVTARNFPPSQDASGDLYT
TSSQLTLPATQCPDGKSVTCHVKHYTNPSQDVTVPCPVPPPPCCHPRLSLHRPALEDLLLGSEA
NLTCTLTGLRDASGATFTWTPSSGKSAVQGPPERDLCGCYSVSSVLPGCAQPWNHGETFTCTAAH
PELKTPLTANITKSGNTFRPEVHLLPPPSEELALNELVTLTCLARGFSPKDVLVRWLQGSQELPR
EKYLTWASRQEPSQGTTTFAVTSILRVAAEDWKKGDTFSCMVGHEALPLAFTQKTIDRLAGKPTH
VNVSVVMAEVDGTCYStop Kappa-LC constant region SEQ ID NO: 6

RTVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGECStop Fig. 25
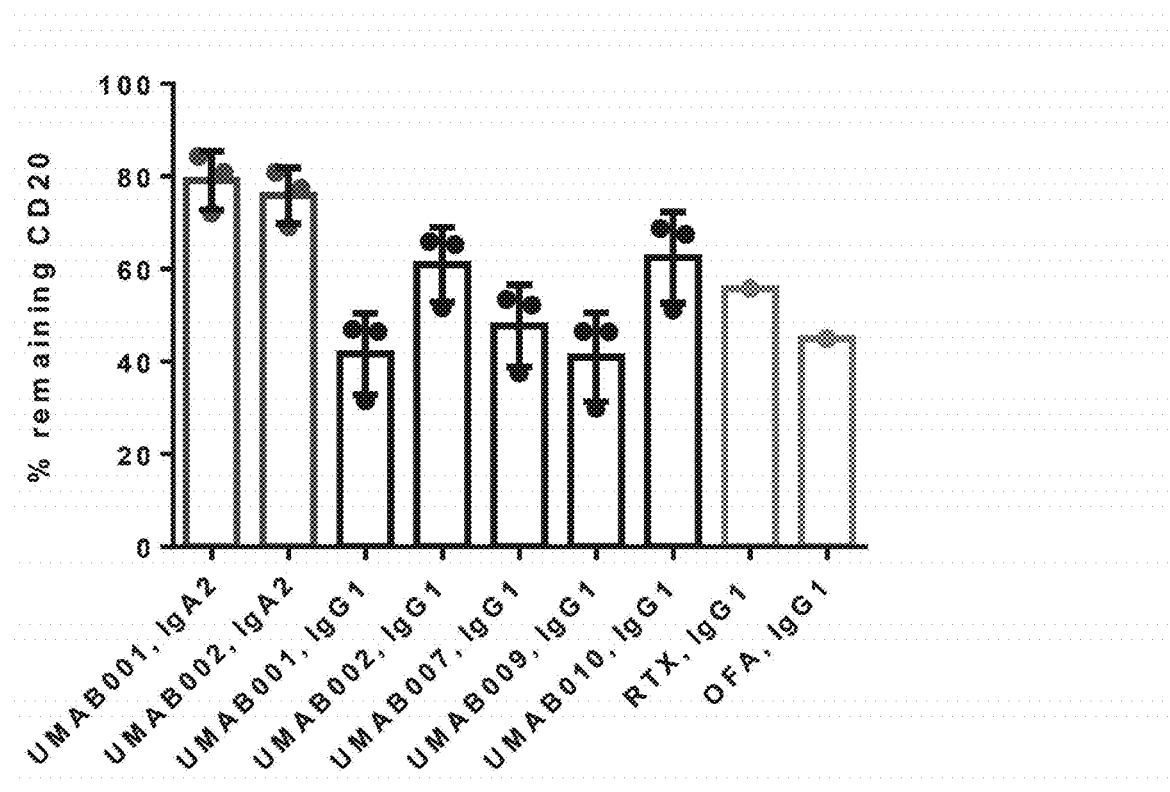
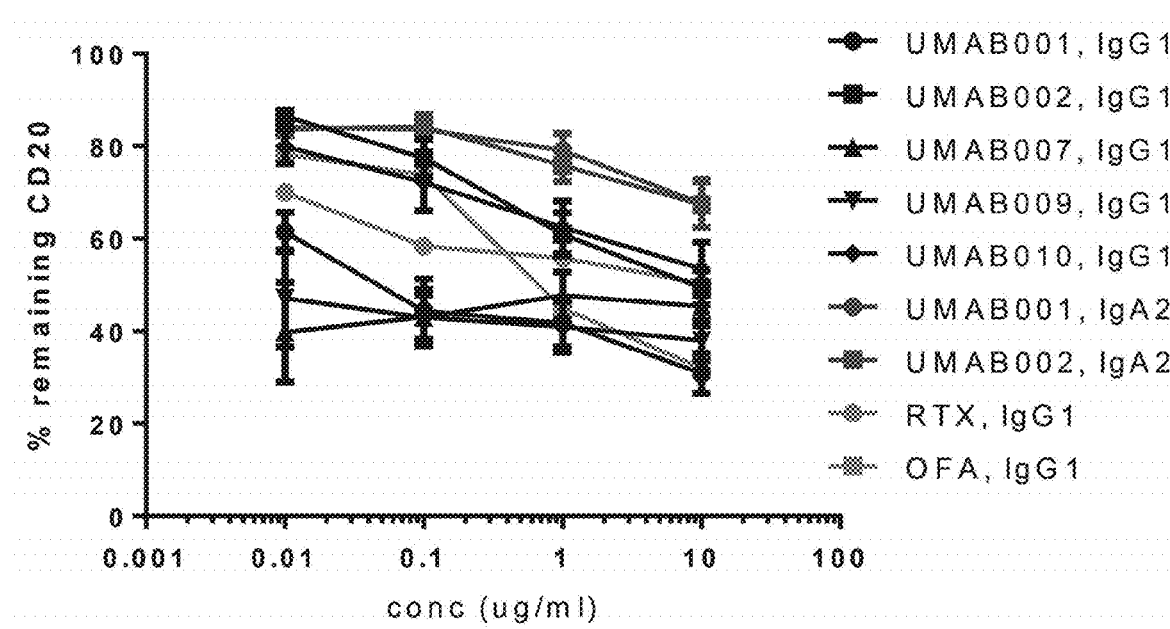

Fig. 26.1
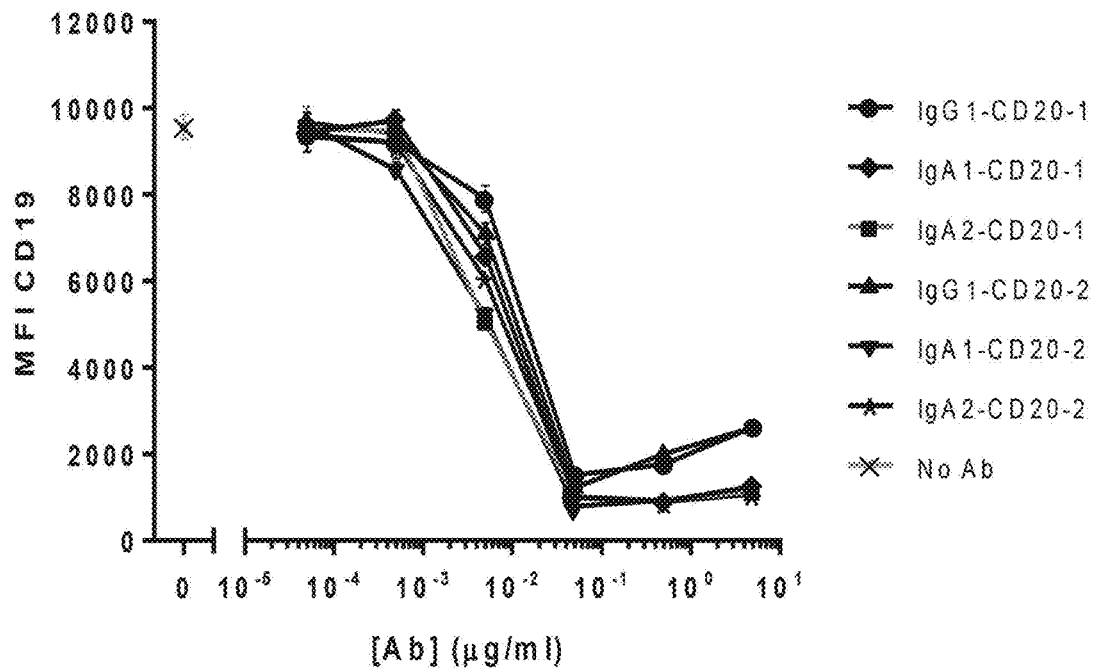
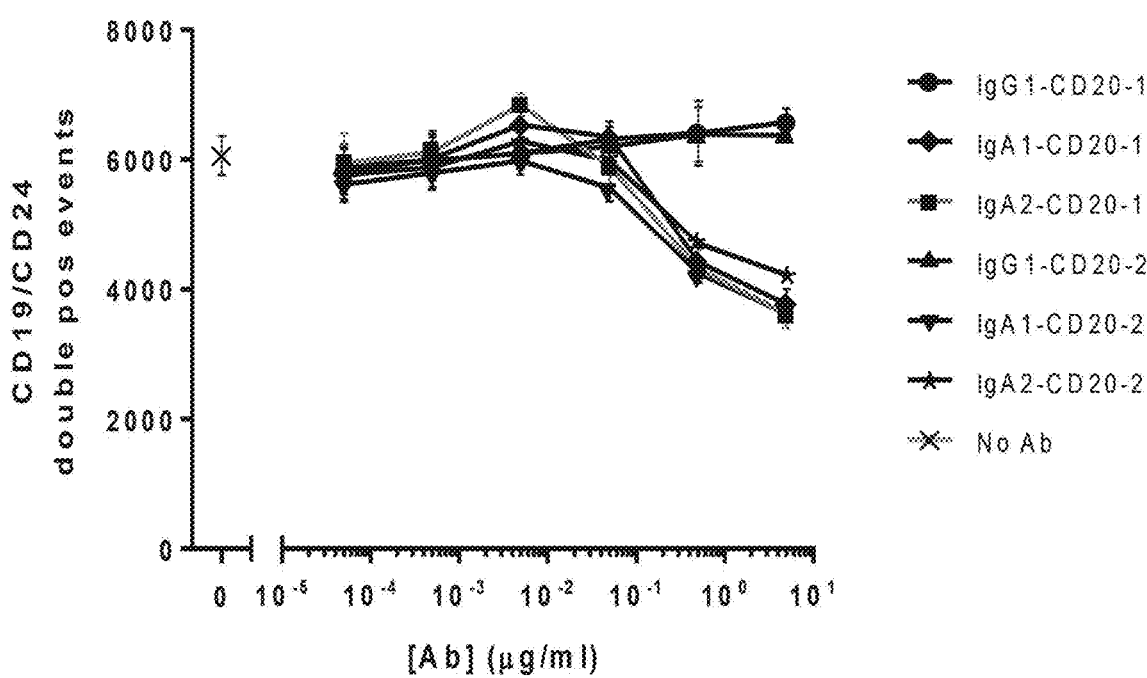

Fig. 26.2
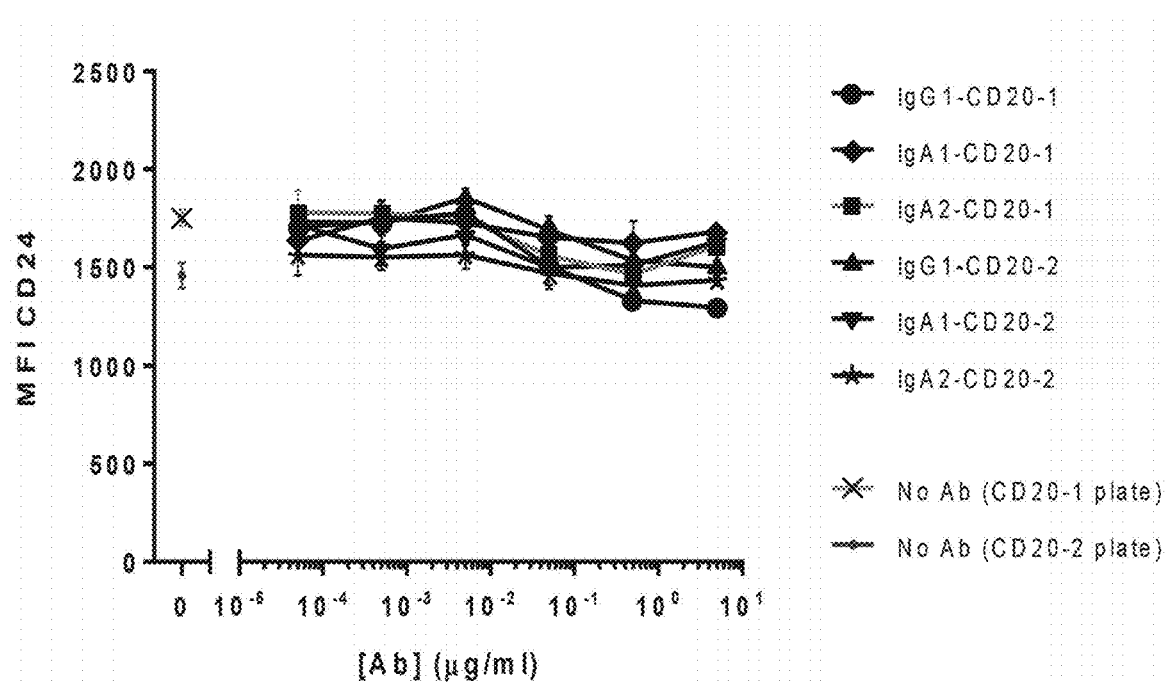
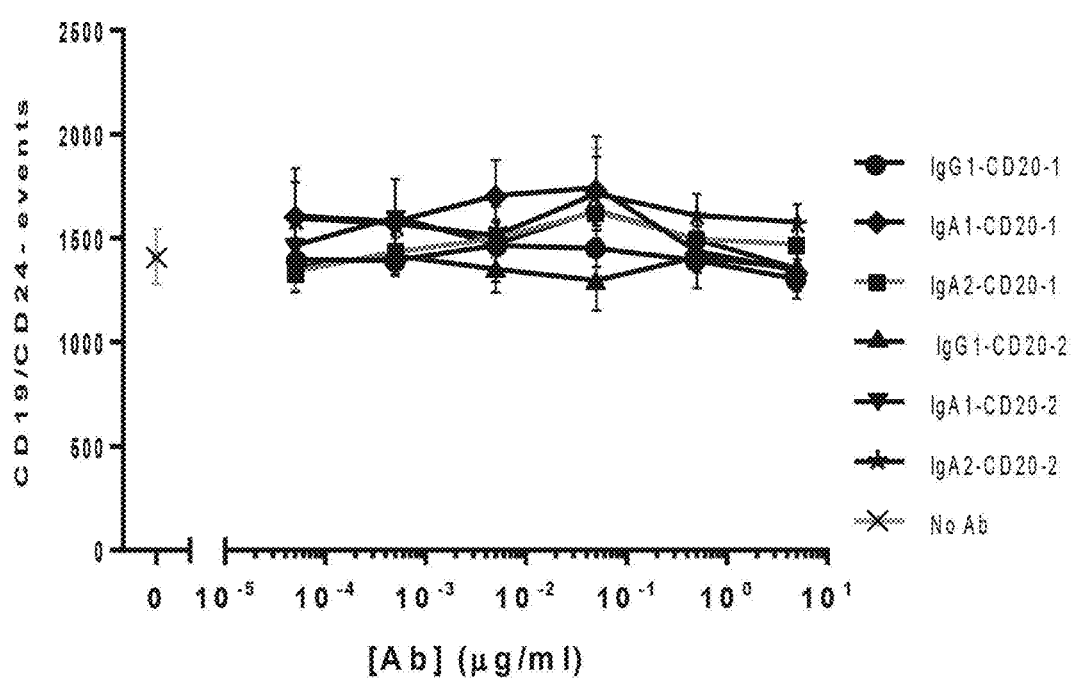

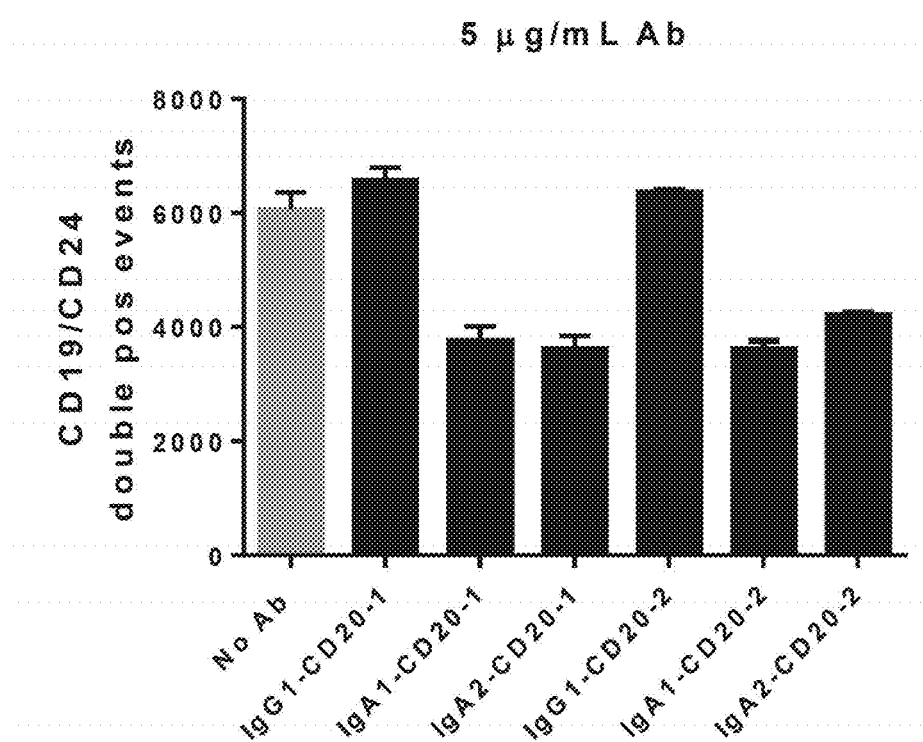
Fig. 26.3

SEQUENCE LISTING

```
<160> NUMBER OF SEQ ID NOS: 33

<210> SEQ ID NO 1
<211> LENGTH: 122
<212> TYPE: PRT
<213> ORGANISM: Artificial Sequence
<220> FEATURE:
<223> OTHER INFORMATION: m1/CD20-1 VH

<400> SEQUENCE: 1

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Leu His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Arg Leu Thr Ser Glu Asp Ser Ala Val Tyr Phe Cys
                85                  90                  95
```

Ala Arg Ser Asn Ser Tyr Gly Ser Thr Tyr Trp Tyr Phe Asp Val Trp
            100                 105                 110

Gly Thr Gly Thr Thr Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: m1/CD20-1 VL

<400> SEQUENCE: 2

Gln Ile Val Leu Ser Gln Ser Pro Ala Val Leu Phe Ala Ser Pro Gly
1               5                   10                  15

Glu Lys Val Thr Met Thr Cys Arg Ala Arg Ser Ser Val Ser Tyr Met
            20                  25                  30

Asp Trp Tyr Gln Gln Lys Pro Arg Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser
        115                 120

<210> SEQ ID NO 3
<211> LENGTH: 330
<212> TYPE: PRT
<213> ORGANISM: Artificial Sequence
<220> FEATURE:
<223> OTHER INFORMATION: IgG1 constant region

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp

```
                145                 150                 155                 160
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 353
<212> TYPE: PRT
<213> ORGANISM: Artificial Sequence
<220> FEATURE:
<223> OTHER INFORMATION: IgA1 constant region

<400> SEQUENCE: 4

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Asp
                165                 170                 175

Arg Asp Leu Cys Gly Cys Tyr Ser Val Ser Ser Val Leu Pro Gly Cys
```

-continued

```
                180                 185                 190
Ala Glu Pro Trp Asn His Gly Lys Thr Phe Thr Cys Thr Ala Ala Tyr
            195                 200                 205

Pro Glu Ser Lys Thr Pro Leu Thr Ala Thr Leu Ser Lys Ser Gly Asn
        210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
            245                 250                 255

Pro Lys Asp Val Leu Val Arg Trp Leu Gln Gly Ser Gln Glu Leu Pro
        260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
        290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr
```

<210> SEQ ID NO 5
<211> LENGTH: 340
<212> TYPE: PRT
<213> ORGANISM: Artificial Sequence
<220> FEATURE:
<223> OTHER INFORMATION: IgA2m1 constant region

<400> SEQUENCE: 5

```
Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190
```

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Met Ala Glu Val Asp
                325                 330                 335

Gly Thr Cys Tyr
            340

<210> SEQ ID NO 6
<211> LENGTH: 107
<212> TYPE: PRT
<213> ORGANISM: Artificial Sequence
<220> FEATURE:
<223> OTHER INFORMATION: Kappa-LC constant region

<400> SEQUENCE: 6

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 7
<211> LENGTH: 121
<212> TYPE: PRT
<213> ORGANISM: Artificial Sequence
<220> FEATURE:
<223> OTHER INFORMATION: m2/CD20-2 VH

<400> SEQUENCE: 7

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile

```
                35                  40                  45

Gly Gly Ile Tyr Pro Gly Asn Gly Asp Thr Ser Tyr Asn Gln Lys Phe
        50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Tyr Tyr Gly Ser Ser Tyr Gly Ala Met Asp Tyr Trp Gly
                100                 105                 110

Gln Gly Thr Ser Val Thr Val Ser Ser
            115                 120

<210> SEQ ID NO 8
<211> LENGTH: 121
<212> TYPE: PRT
<213> ORGANISM: Artificial Sequence
<220> FEATURE:
<223> OTHER INFORMATION: m2/CD20-2 VL

<400> SEQUENCE: 8

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Ala
65                  70                  75                  80

Asp Ala Ala Thr Tyr Tyr Cys His Gln Trp Thr Phe Asn Pro Pro Thr
                85                  90                  95

Phe Gly Gly Gly Thr Lys Leu Glu Ile Lys Arg Ala Asp Ala Ala Pro
                100                 105                 110

Thr Val Ser Ile Phe Pro Pro Ser Ser
            115                 120

<210> SEQ ID NO 9
<211> LENGTH: 123
<212> TYPE: PRT
<213> ORGANISM: Artificial Sequence
<220> FEATURE:
<223> OTHER INFORMATION: m7/CD20-7 VH

<400> SEQUENCE: 9

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Ala Ser Tyr
                20                  25                  30

Asn Met His Trp Ile Lys Gln Thr Pro Arg Gln Gly Leu Glu Trp Ile
            35                  40                  45

Ala Ala Ile Tyr Pro Gly Asn Gly Asp Thr Ser Tyr Asn Gln Lys Phe
        50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95
```

Ala Arg Thr Tyr Tyr Gly Ser Ser Pro Tyr Trp Ser Phe Asp Val
            100                 105                 110

Trp Gly Thr Gly Thr Thr Val Thr Val Ser Ser
        115                 120

<210> SEQ ID NO 10
<211> LENGTH: 122
<212> TYPE: PRT
<213> ORGANISM: Artificial Sequence
<220> FEATURE:
<223> OTHER INFORMATION: m7/CD20-7 VL

<400> SEQUENCE: 10

Asp Ile Gln Met Thr Gln Ser Pro Ala Ser Leu Ser Ala Ser Val Gly
1               5                   10                  15

Glu Thr Val Thr Val Thr Cys Gly Ala Ser Tyr Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Asn Pro Pro
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser
            115                 120

<210> SEQ ID NO 11
<211> LENGTH: 123
<212> TYPE: PRT
<213> ORGANISM: Artificial Sequence
<220> FEATURE:
<223> OTHER INFORMATION: m9/CD20-9 VH

<400> SEQUENCE: 11

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Pro Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Ser Gln Thr Val Asp Lys Ser Ser Thr Val Tyr
65                  70                  75                  80

Met Gln Leu Ser Ser Leu Thr Ser Ala Asp Ser Ala Val Tyr Phe Cys
                85                  90                  95

Ala Arg Ser Arg Leu Phe Asp Ser Ser Tyr Gly Trp Tyr Phe Asp Val
            100                 105                 110

Trp Gly Thr Gly Thr Thr Val Thr Val Ser Ser
        115                 120

<210> SEQ ID NO 12
<211> LENGTH: 121
<212> TYPE: PRT
<213> ORGANISM: Artificial Sequence
<220> FEATURE:
<223> OTHER INFORMATION: m9/CD20-9 VL

<400> SEQUENCE: 12

Gln Ile Val Leu Ser Gln Ser Pro Ala Ile Leu Ser Ala Tyr Pro Gly
1               5                   10                  15

Glu Lys Val Thr Met Thr Cys Arg Ala Arg Ser Ser Val Ser Tyr Ile
            20                  25                  30

Asp Trp Tyr Gln Gln Lys Ala Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser
        115                 120

<210> SEQ ID NO 13
<211> LENGTH: 122
<212> TYPE: PRT
<213> ORGANISM: Artificial Sequence
<220> FEATURE:
<223> OTHER INFORMATION: m10/CD20-10 VH

<400> SEQUENCE: 13

Gln Ala Tyr Leu Gln Gln Ser Gly Ala Asp Leu Val Arg Pro Gly Ala
1               5                   10                  15

Ser Val Lys Met Ser Cys Lys Ala Ser Gly Phe Thr Phe Pro Ser Tyr
            20                  25                  30

Asn Leu His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Ala Tyr Tyr Gly Ser Asn Val Trp Phe Phe Asp Val Trp
            100                 105                 110

Gly Thr Gly Thr Thr Val Thr Val Ser Ser
        115                 120

<210> SEQ ID NO 14
<211> LENGTH: 121
<212> TYPE: PRT
<213> ORGANISM: Artificial Sequence
<220> FEATURE:
<223> OTHER INFORMATION: m10/CD20-10 VL

<400> SEQUENCE: 14

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

```
Asp Trp Tyr Gln Gln Lys Pro Gly Ser Ser Pro Lys Pro Trp Ile Tyr
        35                  40                  45

Ala Thr Ser Asn Leu Ala Ser Gly Val Pro Thr Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ile Ser Asn Pro Pro Thr
                85                  90                  95

Phe Gly Ala Gly Thr Lys Leu Asp Leu Lys Arg Ala Asp Ala Ala Pro
            100                 105                 110

Thr Val Ser Ile Phe Pro Pro Ser Ser
        115                 120
```

<210> SEQ ID NO 15
<211> LENGTH: 9
<212> TYPE: PRT
<213> ORGANISM: Artificial Sequence
<220> FEATURE:
<223> OTHER INFORMATION: overlapping epitope of Type II mAbs OBZ and B1

<400> SEQUENCE: 15

```
Ala Asn Pro Ser Glu Lys Asn Ser Pro
1               5
```

<210> SEQ ID NO 16
<211> LENGTH: 21
<212> TYPE: PRT
<213> ORGANISM: Artificial Sequence
<220> FEATURE:
<223> OTHER INFORMATION: circular epitope for epitope mapping

<400> SEQUENCE: 16

```
Tyr Asn Cys Glu Pro Ala Asn Pro Ser Glu Lys Asn Ser Pro Ser Thr
1               5                   10                  15

Gln Tyr Cys Tyr Ser
            20
```

<210> SEQ ID NO 17
<211> LENGTH: 5
<212> TYPE: PRT
<213> ORGANISM: Artificial Sequence
<220> FEATURE:
<223> OTHER INFORMATION: typical residues of CDR-H2

<400> SEQUENCE: 17

```
Leu Glu Trp Ile Gly
1               5
```

<210> SEQ ID NO 18
<211> LENGTH: 4
<212> TYPE: PRT
<213> ORGANISM: Artificial Sequence
<220> FEATURE:
<223> OTHER INFORMATION: Typical residues of CDR-H3
<220> FEATURE:
<221> NAME/KEY: misc_feature
<222> LOCATION: (3)..(3)
<223> OTHER INFORMATION: Xaa can be any naturally occurring amino acid

<400> SEQUENCE: 18

```
Trp Gly Xaa Gly
1
```

<210> SEQ ID NO 19

```
<211> LENGTH: 4
<212> TYPE: PRT
<213> ORGANISM: Artificial Sequence
<220> FEATURE:
<223> OTHER INFORMATION: typical residues of CDR L3
<220> FEATURE:
<221> NAME/KEY: misc_feature
<222> LOCATION: (3)..(3)
<223> OTHER INFORMATION: Xaa can be any naturally occurring amino acid

<400> SEQUENCE: 19

Phe Gly Xaa Gly
1

<210> SEQ ID NO 20
<211> LENGTH: 15
<212> TYPE: PRT
<213> ORGANISM: Artificial Sequence
<220> FEATURE:
<223> OTHER INFORMATION: linear peptide used for epitope mapping

<400> SEQUENCE: 20

Asn Ser Pro Ser Thr Gln Tyr Gly Pro Ala Asn Pro Ser Glu Lys
1               5                   10                  15

<210> SEQ ID NO 21
<211> LENGTH: 13
<212> TYPE: PRT
<213> ORGANISM: Artificial Sequence
<220> FEATURE:
<223> OTHER INFORMATION: CDR3

<400> SEQUENCE: 21

Ser Asn Ser Tyr Gly Ser Thr Tyr Trp Tyr Phe Asp Val
1               5                   10

<210> SEQ ID NO 22
<211> LENGTH: 12
<212> TYPE: PRT
<213> ORGANISM: Artificial Sequence
<220> FEATURE:
<223> OTHER INFORMATION: CDR3

<400> SEQUENCE: 22

Tyr Tyr Tyr Gly Ser Ser Tyr Gly Ala Met Asp Tyr
1               5                   10

<210> SEQ ID NO 23
<211> LENGTH: 14
<212> TYPE: PRT
<213> ORGANISM: Artificial Sequence
<220> FEATURE:
<223> OTHER INFORMATION: CDR3

<400> SEQUENCE: 23

Thr Tyr Tyr Tyr Gly Ser Ser Pro Tyr Trp Ser Phe Asp Val
1               5                   10

<210> SEQ ID NO 24
<211> LENGTH: 14
<212> TYPE: PRT
<213> ORGANISM: Artificial Sequence
<220> FEATURE:
<223> OTHER INFORMATION: CDR3

<400> SEQUENCE: 24

Ser Arg Leu Phe Asp Ser Ser Tyr Gly Trp Tyr Phe Asp Val
1               5                   10
```

```
<210> SEQ ID NO 25
<211> LENGTH: 13
<212> TYPE: PRT
<213> ORGANISM: Artificial Sequence
<220> FEATURE:
<223> OTHER INFORMATION: CDR3

<400> SEQUENCE: 25

Ser Ala Tyr Tyr Gly Ser Asn Val Trp Phe Phe Asp Val
1               5                   10

<210> SEQ ID NO 26
<211> LENGTH: 5
<212> TYPE: PRT
<213> ORGANISM: Artificial Sequence
<220> FEATURE:
<223> OTHER INFORMATION: VH CDR1

<400> SEQUENCE: 26

Ser Tyr Asn Leu His
1               5

<210> SEQ ID NO 27
<211> LENGTH: 17
<212> TYPE: PRT
<213> ORGANISM: Artificial Sequence
<220> FEATURE:
<223> OTHER INFORMATION: VH CDR2

<400> SEQUENCE: 27

Ala Ile Tyr Pro Gly Asn Gly Asp Thr Ser Tyr Asn Gln Lys Phe Lys
1               5                   10                  15

Gly

<210> SEQ ID NO 28
<211> LENGTH: 5
<212> TYPE: PRT
<213> ORGANISM: Artificial Sequence
<220> FEATURE:
<223> OTHER INFORMATION: VH CDR1

<400> SEQUENCE: 28

Ser Tyr Asn Met His
1               5

<210> SEQ ID NO 29
<211> LENGTH: 17
<212> TYPE: PRT
<213> ORGANISM: Artificial Sequence
<220> FEATURE:
<223> OTHER INFORMATION: VH CDR2

<400> SEQUENCE: 29

Gly Ile Tyr Pro Gly Asn Gly Asp Thr Ser Tyr Asn Gln Lys Phe Lys
1               5                   10                  15

Gly

<210> SEQ ID NO 30
<211> LENGTH: 10
<212> TYPE: PRT
<213> ORGANISM: Artificial Sequence
<220> FEATURE:
<223> OTHER INFORMATION: overlapping epitope of Type II mAbs OBZ and B1

<400> SEQUENCE: 30
```

```
Pro Ala Asn Pro Ser Glu Lys Asn Ser Pro
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ala Arg Ser Ser Val Ser Tyr Met Asp
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Thr Ser Asn Leu Ala Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Trp Thr Ser Asn Pro Pro Thr
1               5
```

CD20 ANTIBODIES

CROSS-REFERENCE TO RELATED APPLICATIONS

This application is a national phase entry under 35 U.S.C. § 371 of International Patent Application PCT/NL2017/050581, filed Sep. 1, 2017, designating the United States of America and published in English as International Patent Publication WO 2018/044172 A1 on Mar. 8, 2018, which claims the benefit under Article 8 of the Patent Cooperation Treaty to European Patent Application Serial No. 16186850.0, filed Sep. 1, 2016.

TECHNICAL FIELD

The disclosure relates to the field of antibodies. In particular, it relates to antibodies that bind CD20. It further relates to the use of CD20 antibodies in medical and detection methods. The disclosure further relates to cells, nucleic acid molecules and methods for the production of the antibodies.

SEQUENCE LISTING

The instant application contains a Sequence Listing which has been submitted electronically in ASCII format and is hereby incorporated by reference in its entirety. Said ASCII copy, created on Jan. 25, 2022, is named 199828-702831_SL.txt and is 28,210 bytes in size.

BACKGROUND

Three CD20 mAbs have been approved for the treatment of various subtypes of Non-Hodgkin's lymphomas and leukemias (NHL). Rituximab (RTX), the first mAb on the market, has significantly improved survival of patients when given in combination with chemotherapy regimens.[1-5] Ofatumumab (OFA) was selected based on its ability to activate the classical complement pathway, leading to membrane disruption and complement-dependent cytotoxicity (CDC). Clinical trials highlighted its emerging potential in combination therapies and maintenance of e.g., chronic lymphocytic leukemia (CLL) patients.[6, 7] Obinutuzumab (OBZ; GA101), a CD20 mAb with enhanced FcγRIII binding and direct programmed cell death (PCD) induction capacity, has been approved for first-line treatment of CLL[8] and RTX refractory follicular NHL.[9]

In vitro, CD20 mAbs can induce antibody-dependent cell-mediated cytotoxicity/phagocytosis (ADCC/ADCP), CDC or PCD. Depending on their mechanism-of-actions (MoA), CD20 mAbs are grouped into Type I and Type II. Both Type I and II mAbs elicit ADCC Type I mAbs, including RTX and OFA, relocate CD20 into lipid rafts and efficiently activate the complement system.[10] Type II mAbs induce PCD via a caspase-independent pathway.[11] The only described Type II mAbs are OBZ,[12] B1,[13] and 11B8.[14] Interestingly, RTX was shown to induce PCD via the same pathway in lymphoma cell lines and primary CLL cells, but to a lower extent than Type II mAbs.[15] Most recently, a CD20 mAb displaying Type I and Type II characteristics in vitro was described.[16]

In literature, three features were suggested to govern Type I/II classification: (a) the epitope, (b) binding kinetics and (c) residues within the elbow-hinge angle determining region of the VH chain framework.

Human CD20 comprises a small (residue 72-80) and larger (residue 140-186) extracellular loop. The epitope of RTX is located on the larger loop with $^{170}$ANPS$^{173}$ representing the core binding region.[17] Mutagenesis experiments confirmed N171 to be an important residue for RTX.[18] For RTX and another panel of Type I mouse CD20 mAbs A170 and P172 were determined to be important.[19, 20] Although Type II mAbs OBZ and B1 have an overlapping epitope ($^{170}$ANPSEKNSP$^{178}$ (SEQ ID NO:15)) with RTX, residues 176-178 contribute most to the binding.[18] In contrast, the epitope of the Type I mAb OFA and Type II mAb 11B8 is comprised by residues on the small and larger loop.[20] As OFA recognizes this unique epitope and efficiently activates complement, it was suggested that the membrane-proximal binding results in a beneficial orientation of the available Fc-fragments allowing better complement deposition. Additionally, Ab kinetics were proposed to correlate with the CDC activity of CD20 mAbs, as the strong complement inducer OFA dissociates significantly more slowly from CD20 than RTX with an intermediate CDC capacity.[14] Further evidence supporting the contribution of a slower off-rate to better CDC induction comes from studies with the CD20 mAb veltuzumab.[21]

Next to antigen binding properties, a structural Ab feature was suggested. During the humanization of BLy-1 (Type I) to OBZ (Type II) a L11V mutation was introduced in the VH chain framework. The reverse mutation in OBZ resulted in loss of PCD induction.[12] Modeling of RTX and OBZ indicated that the L11V mutation results in a wider Ab elbow-hinge angle for OBZ (167°) compared to RTX (140°).[18]

Although various CD20 antibodies are known there is still little known about the properties that determine the mechanism-of-action of CD20 mAbs.

BRIEF SUMMARY

The disclosure shows novel CD20 antibodies. All antibodies display Type I characteristics whereas some of these also display Type II characteristics. It was found that neither the epitope, nor the off-rate are by themselves is enough to predict whether a CD20 antibody exhibits a Type I, a Type II or Type I/II activity.

This disclosure further provides CD20 antibodies with a human IgA constant region. IgA is the second most prominent antibody in blood, after IgG, and the predominant Ab at the mucosa. The monomeric version of IgA is mostly found in serum, whereas polymeric IgA is produced at mucosal sites. The 2 Ab subclasses, IgA1 and IgA2, differ structurally in their hinge regions, which is 13 amino acids longer for IgA1 compared to IgA2. This might enable an improved reach for antigens that are distant, but at the same time makes it more prone to degradation by proteases.[36] Furthermore, the hinge region of IgA1 Abs carries several O-linked glycosylation sites, which are absent in IgA2 Abs. IgA2 exists as 3 allotypes; IgA2(m1) which has 2 additional N-linked glycosylation sites compared with IgA1, and IgA2(m2) and IgA2(n), which have 3 additional N-linked glycosylation sites. Contrary to IgG, IgA is a weak activator of the classical complement pathway as it cannot bind C1q.[37] However, IgA mAbs have been shown to activate the complement system through the lectin pathway, as the carbohydrate recognition domain (CRD) of mannan-binding lectin (MBL) can bind to IgA.[38]

IgA engages immune effector cells by binding to the FcαRI (CD89), which is expressed on cells of the myeloid lineage: neutrophils, monocytes, different macrophage populations and eosinophils.[39] Expression on in vitro generated dendritic cells was shown,[40, 41] but remains controversial. Neutrophils express high levels of FcαRI, while macrophages have lower expression.[42] In ADCC assays with IgA mAbs targeting solid tumor targets, neutrophils have been shown to efficiently eradicate tumor cells.[43-46] In contrast, IgG1 mAbs were less able to engage this effector cell population. Monocyte/macrophage-mediated tumor cell killing was shown to be comparable between IgA and IgG mAbs.[43] Next to the activating FcγRIIIa, macrophages also express the inhibitory FcγRIIb. It has been shown that the presence of FcγRIIb reduces mAb activity.[47] For IgA, no inhibitory receptor has been described yet.

The knowledge on IgA mAb targeting tumor-associated antigens has increased significantly over the last few years. Several bottlenecks faced a few years ago are now overcome, and are currently able to produce and purify sufficient amounts of monomeric IgA mAbs for in vitro and in vivo testing. Mice lack a receptor for IgA, therefore the generation of human FcαRI transgenic now allows in vivo testing.[48] Boross and colleagues eventually showed in an immunocompetent tumor model the great potential of IgA mAbs in a therapeutic setting.[44] The majority of IgA mAbs studied so far are targeting HER2 or EGFR, antigens expressed on solid tumors. Only one study has looked at the potential of monomeric IgA-CD20 mAbs.[49] Complement-mediated tumor cell killing was demonstrated to rely on weak indirect activation of the classical pathway and more pronounced direct activation of the alternative pathway. With a passive immunization strategy in FcαRI transgenic mice, a good protection against tumor development with monomeric IgA2-CD20 mAbs was achieved. However, therapeutic in vivo testing for IgA-CD20 mAbs has not yet been performed. Further, a direct comparison of IgA1 and IgA2 mAbs, in particular, with respect to their complement activation properties is lacking. The disclosure describes unique IgA1- and IgA2-CD20 mAbs.

The disclosure provides an antibody comprising a mouse IgG2; a human IgG1, IgA1 or IgA2 constant region and a variable domain that can bind the epitope "EPANpSEK" (one letter code for Glu Pro Ala Asn Pro Ser Glu Lys (SEQ ID NO:31)) on human CD20 expressed on Ramos cells and which antibody has an increased PCD functionality when compared to Rituximab with a constant region of the same isotype.

The disclosure also provides an antibody that can bind to an extracellular part of human CD20 expressed on Ramos cells comprising a variable domain with a heavy chain variable region and a light chain variable region, wherein the heavy chain variable region comprises a CDR3 region with the sequence SNSYGSTYWYFDV (SEQ ID NO:21).

The disclosure further provides an antibody comprising a mouse IgG2; a human IgG1, IgA1 or IgA2 constant region and a variable domain that can bind the epitope "EPANPsEK" (SEQ ID NO:31) on human CD20 expressed on Ramos cells and which antibody has an increased ADCC functionality when compared to Rituximab with a constant region of the same isotype.

Also provided is an antibody that can bind to an extracellular part of human CD20 expressed on Ramos cells, the antibody comprising a variable domain with a heavy chain variable region and a light chain variable region, wherein the heavy chain variable region comprises a CDR3 region with the sequence YYYGSSYGAMDY (SEQ ID NO:22).

Further provided is an antibody comprising a mouse IgG2; a human IgG1, IgA1 or IgA2 constant region and a variable domain that can bind the epitope "EPANpsEK" (SEQ ID NO:31) on human CD20 expressed on Ramos cells and which antibody has an increased CDC functionality when compared to Rituximab with a constant region of the same isotype.

Also provided is an antibody that can bind to an extracellular part of human CD20 expressed on Ramos cells comprising a variable domain with a heavy chain variable region and a light chain variable region, wherein the heavy chain variable region comprises a CDR3 region with the sequence TYYYGSSPYWSFDV (SEQ ID NO:23).

Also provided is an antibody that can bind to an extracellular part of human CD20 expressed on Ramos cells comprising a variable domain with a heavy chain variable region and a light chain variable region, wherein the heavy chain variable region comprises a CDR3 region with the sequence SRLFDSSYGWYFDV (SEQ ID NO:24).

Further provided is an antibody comprising a mouse IgG2; a human IgG1, IgA1 or IgA2 constant region and a variable domain that can bind the epitope "EPANpSEK" (SEQ ID NO:31) on human CD20 expressed on Ramos cells and which antibody has an increased CDC and/or increased ADCC functionality when compared to Rituximab with a constant region of the same isotype.

Also provided is an antibody that can bind to an extracellular part of human CD20 expressed on Ramos cells comprising a variable domain with a heavy chain variable region and a light chain variable region, wherein the heavy chain variable region comprises a CDR3 region with the sequence SAYYGSNVWFFDV (SEQ ID NO:25).

Further provided are antibodies as described herein for use in the treatment of a disease in an individual.

Also provided are antibodies as described herein for use in the treatment of a disease that involves too many B cells, overactive B cells, and/or dysfunctional B cells.

Also provided are antibodies as described herein for use in the treatment of a CD20 positive neoplasm such as a CD20 positive B-cell lymphoma; hairy cell leukemia; B-cell chronic lymphocytic leukemia, or melanoma.

Also provided are methods for the treatment of an individual that has a disease that involves too many B cells, overactive B cells, and/or dysfunctional B cells comprising administering to the individual in need thereof an antibody as described herein.

Also provided are methods for the treatment of an individual that has a CD20 positive neoplasm such as a CD20 positive B-cell lymphoma; hairy cell leukemia; B-cell chronic lymphocytic leukemia, or melanoma comprising administering to the individual in need thereof an antibody as described herein.

Also provided are methods for the treatment of children with B-cell malignancies and pediatric leukemia patients that have a B-cell disease after stem cell transplantation. In pediatric patients, long-term adverse effects of rituximab are noted: permanent depletion of B cells and inability of naïve B cells to switch to memory B cells, resulting in life-long immunoglobulin depletion. The long persistence of IgG in the body is probably accountable. An IgA antibody described herein has a stronger ADCC function when compared to an IgG antibody comprising the same variable domain. This is apparent when a B-cell-specific marker is analyzed that is not subject to trogocytosis upon incubation of the cell with a CD20 antibody. An IgA antibody described herein has a short half-life when compared to an IgG antibody comprising the same variable domain. The IgA antibodies as described herein cause fewer side effects when compared to an IgG antibody with the same variable domain. In short, the IgA antibodies of the disclosure facilitate an effective hit but are also cleared fast enough to allow a good recovery of the B-cell repertoire. This is particularly helpful in preserving the B-cell repertoire following recovery from the treatment, particularly in the mentioned leukemia patients that have a B-cell disease after stem cell transplantation treated with an antibody of the disclosure and pediatric patients after B-cell depletion with an antibody of the disclosure.

The disclosure further provides a variable domain comprising the amino acid sequence of the heavy and light chain variable regions of SEQ ID NOS:1 and 2, each with 0-5 amino acid insertions, deletions, substitutions, additions or a combination thereof at one or more positions other than positions of the amino acids that constitute the CDR1, CDR2 and CDR3 regions.

The disclosure further provides a variable domain comprising the amino acid sequence of the heavy and light chain variable regions of SEQ ID NOS:7 and 8 each with 0-5 amino acid insertions, deletions, substitutions, additions or a combination thereof at one or more positions other than positions of the amino acids that constitute the CDR1, CDR2 and CDR3 regions.

The disclosure further provides a variable domain comprising the amino acid sequence of the heavy and light chain variable regions of SEQ ID NOS: 9 and 10 each with 0-5 amino acid insertions, deletions, substitutions, additions or a combination thereof at one or more positions other than positions of the amino acids that constitute the CDR1, CDR2 and CDR3 regions.

The disclosure further provides a variable domain comprising the amino acid sequence of the heavy and light chain variable regions of SEQ ID NOS:11 and 12 each with 0-5 amino acid insertions, deletions, substitutions, additions or a combination thereof at one or more positions other than positions of the amino acids that constitute the CDR1, CDR2 and CDR3 regions.

The disclosure further provides a variable domain comprising the amino acid sequence of the heavy and light chain variable regions of SEQ ID NOS:13 and 14 each with 0-5 amino acid insertions, deletions, substitutions, additions or a combination thereof at one or more positions other than positions of the amino acids that constitute the CDR1, CDR2 and CDR3 regions. Further provided is an antibody comprising a variable domain as specified herein.

Further provided is
a nucleic acid molecule that codes for a heavy chain or light chain of an antibody as described herein;
a nucleic acid molecule that codes for the CDR3 of a heavy or light chains of an antibody as described herein;
a nucleic acid molecule that codes for a CDR1, CDR2 and CDR3 of the heavy or light chain of an antibody as described herein; and
a nucleic acid molecule that codes for a variable region of a heavy chain or of a light chain of an antibody as described herein.

Further provided is a cell that comprises nucleic acid that codes for an antibody as described herein.

Further provided are means and methods for the production of an antibody as described herein.

BRIEF DESCRIPTION OF THE DRAWINGS

FIGS. 1.1 and 1.2. Most new CD20 mAbs have unique heavy and light chain sequences. Sequences coding for the variable region of the (A) heavy chain and (B) light chain were aligned and compared with commercially available CD20 mAbs by calculating the average distance using % identity (PID). The right panel is a snapshot of the tree on the left.

(FIG. 2A) PCD: EL4-CD20 cells incubated for 24 hours with 1 µg/mL CD20 mAbs in the absence or presence of cross-linking Ab. PCD determined by 7-AAD$^+$/AnnexinV-PE$^+$ staining (mean+SEM). (FIG. 2B) ADCC: Specific lysis of Daudi cells in a chromium release assay with PBMCs as effector cells (E:T=100:1) at 1 µg/mL CD20 mAb (mean+SEM). (FIG. 2C) CDC by new CD20 mAbs was determined at 10 and 1 µg/mL mAb in 15.5% human serum and detected by 7-AAD staining ((value$_{sample}$–mean$_{medium}$)+SEM). mIgG2a-CD20 mAbs B1, mRTX, and m7D8 in grey were taken along as controls. mIgG2c mAbs in pink and mIgG2b mAbs in blue.

FIGS. 3A, 3B. New mIgG2c-CD20 mAbs display varying CDC properties. Induction of complement-dependent cytotoxicity by (FIG. 3A) all new mIgG2c-CD20 mAbs on Daudi cells and (FIG. 3B) m1, m2 and m7D8 on Ramos and Raji cells. mIgG2a-CD20 mAbs B1 and m7D8 were taken along as controls. Cells were incubated with indicated mAb concentrations and 15.5% human serum. Cytotoxicity was determined by 7-AAD staining ((value$_{sample}$–mean$_{medium}$)+SEM).

FIGS. 4A-4C. Binding site on CD20 is different among new CD20 mAbs. (FIG. 4AA) Epitope mapping using the circular peptide YNCEPANPSEKNSPSTQYCYS (SEQ ID NO:16) resulted in identification of the epitope of m1 (left) but only marginally of m2 (right). Binding of 1 µg/mL mAb to the peptide and mutants with each amino acid replaced with all other available (positional scan; excluding cysteine) was determined by ELISA. Grey line and shaded area represents WT binding±SEM. Results are displayed with Tukey-whiskers. (FIG. 4B) Rough epitope mapping with CD20 WT or CD20 mutant (KDD=T159K/N163D/N166D, AxP=A170S/P172S). HEK293F cells were transfected with plasmids and binding of mAbs (5 µg/mL) to CD20 was measured by FACS. Binding was compared to Type I CD20 mAbs (m7D8 and mRTX) and Type II mAbs (B1 and m11B8). (FIG. 4C) Determination of residues crucial for CD20 mAb binding. Data are represented as % of best binder. Coloring according to binding compared to best binder (dark grey: 0-20%=loss of binding; grey: 21-70%=intermediate binding; light grey: 71-100% full binding).

(FIG. 5C) Comparison of dissociation rate constants under non-competitive and competitive conditions determined by 1:1 Fitting model.

CD20 cells 16 hours prior to mAb or PBS treatment. The anti-tumor response was evaluated 24 hours later by determining the amount of remaining tumor cells in the peritoneal lavage with TruCount tubes. (FIG. 7A) mAb titration of m1, m2 and m7D8 (median±interquartile range). (FIG. 7B) Anti-tumor response by 1 µg mIgG2c mAb, represented as % of PBS (median±interquartile range). 1 µg m7D8 (mIgG2a) as positive control. 2 separate experiments as indicated by dashed line.

(FIG. 9A) ADCC: Specific lysis of Daudi cells in a chromium release assay with PBMCs as effector cells (E:T=50:1) over a wider mAb concentration range (mean±SEM). (FIG. 9B) CDC of new CD20 mAbs determined in 15.5% human serum and detected by 7-AAD staining (($value_{sample}-mean_{medium}$)±SEM). (FIG. 9C) PCD: EL4-CD20 cells incubated for 24 hours with 1 µg/mL CD20 mAbs in the absence or presence of 20 µg/mL cross-linking Ab. PCD was determined by 7-AAD/AnnexinV-PE staining (mean+SEM). B1 (mIgG2a-CD20 mAb) is a positive control for PCD (($value_{sample}-mean_{medium}$)±SEM). In all assays RTX and OFA were included as positive controls, and TRA as isotype control. PCD induction on (FIGS. 9D, 9E) Ramos cells and (FIGS. 9F, 9G) Daudi cells by IgG1-CD20-1 without or with the L11V mutation (10 µg/ml). Induction of cell death was determined by (FIGS. 9D, 9F) 7-AAD/AnnexinVPE staining and (FIGS. 9E, 9G) DiOC6/TO-PRO-3 staining (mean+SEM). 11B8 and OFA were taken along as positive and negative control, respectively. Results are representative of 3 separate assays. *$p<0.05$; $p<0.01$; *$p<0.001$, by one way ANOVA followed by Bonferroni posthoc analysis.

(FIG. 10A) FACS plots showing disappearance of viable B cells upon incubation with mAb (here IgG1-CD20-1) compared to PBS control. (FIG. 10B) B-cell depletion mediated by CD20 mAbs determined over a broader concentration range (mean±SEM). RTX and OFA were included as positive controls, and TRA as isotype control.

FIGS. 12A-12C: Production of IgA-CD20 mAbs. (FIG. 12A) Test transfection of HEK293F cells to determine optimal ratio between HC, LC and pAdvantage coding plasmids. Concentrations of produced IgA-CD20 mAbs were measured by an IgA-specific ELISA. Large scale produced IgA-CD20 mAbs were purified by (FIG. 12B) anti-human kappa affinity chromatography, followed by (FIG. 12C) size-exclusion chromatography to separate the full size antibody from loose light chains and aggregates. Representative graphs are displayed.

(FIGS. 15A, 15B) Time dependency of complement induction by IgA-CD20 mAbs. Complement-mediated lysis of (FIG. 15A) Daudi and (FIG. 15B) Ramos cells incubated for 15, 60, 240, and 360 minutes in the presence of 10 µg/mL mAb. (FIG. 15C) The degree of complement-mediated lysis of Ramos cells after 15 minutes incubation with 10 µg/mL mAb was inhibited by pre-treatment of the complement source with the indicated inhibitors (heat inactivated serum; excess of eculizumab; EDTA+MgCl$_2$). Results are shown as ($value_{sample}-mean_{medium}$)+SEM.

FIGS. 16A-16C: B-cell depletion assay in autologous setting. Whole blood leukocytes were incubated with CD20 mAbs for 3 hours at 37° C. Analysis was performed on FSC/SSC lymphocyte gate from which CD3, CD14, CD56 and CD11b positive cells were excluded. CD19 was used as B-cell marker. (FIG. 16A) Analysis of CD19 expression on CD19+ cells (B cells). (FIG. 16B) Number of CD19+ events found in lymphocyte gate. (FIG. 16C) Number of CD19- cells found in lymphocyte gate after background (no antibody) subtraction.

FIG. 18. Amino acid sequence of various VH and VL chains. CDR sequences are underlined from left to right in the sequence CDR1, CDR2 and CDR3.

Figure 2A:
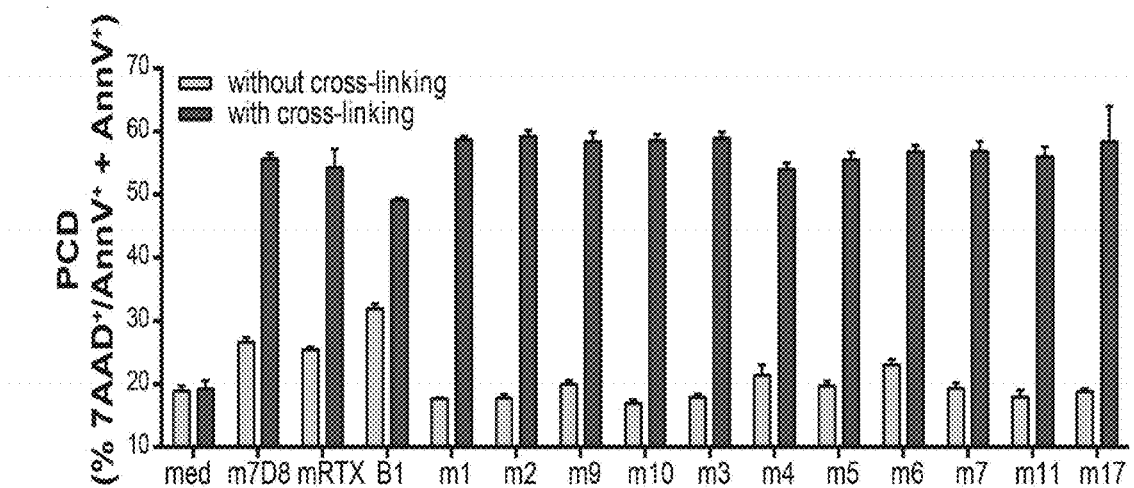
FIGS. 2A-2C. As mouse antibodies, all new CD20 mouse IgG mAbs exhibit Type I characteristics.

The positions of the CDRs in the VH were determined using the following criteria:

CDR-H1
Start—Approx residue 26 (always 4 after a CYS) [Chothia/AbM defintion]. Kabat definition starts 5 residues later. Residues before always CYS-XXX-XXX-XXX. Residues after always a TRP. Typically TRP-VAL, but also, TRP-ILE, TRP-ALA. Length 10 to 12 residues (AbM definition) Chothia definition excludes the last 4 residues.

CDR-H2
Start—always 15 residues after the end of Kabat/AbM definition of CDR-H1. Residues before typically LEU-GLU-TRP-ILE-GLY (SEQ ID NO:17), but a number of variations. Residues after LYS/ARG-LEU/ILE/VAL/PHE/THR/ALA-THR/SER/ILE/ALA. Length Kabat definition 16 to 19 residues.

CDR-H3
Start—always 33 residues after end of CDR-H2 (always 2 after a CYS). Residues before always CYS-XXX-XXX (typically CYS-ALA-ARG). Residues after always TRP-GLY-XXX-GLY (SEQ ID NO:18). Length 3 to 25(!) residues.

The positions of the CDRs in the VL were determined using the following criteria:

CDR-L1
Start—Approx residue 24. Residue before is always a Cys. Residue after is always a Trp. Typically TRP-TYR-GLN, but also, TRP-LEU-GLN, TRP-PHE-GLN, TRP-TYR-LEU. Length 10 to 17 residues.

CDR-L2
Start—always 16 residues after the end of L1. Residues before generally ILE-TYR, but also, VAL-TYR, ILE-LYS, ILE-PHE. Length always 7 residues.

CDR-L3
Start—always 33 residues after end of L2. Residue before is always Cys. Residues after always PHE-GLY-XXX-GLY (SEQ ID NO:19). Length 7 to 11 residues.

Figure 19:
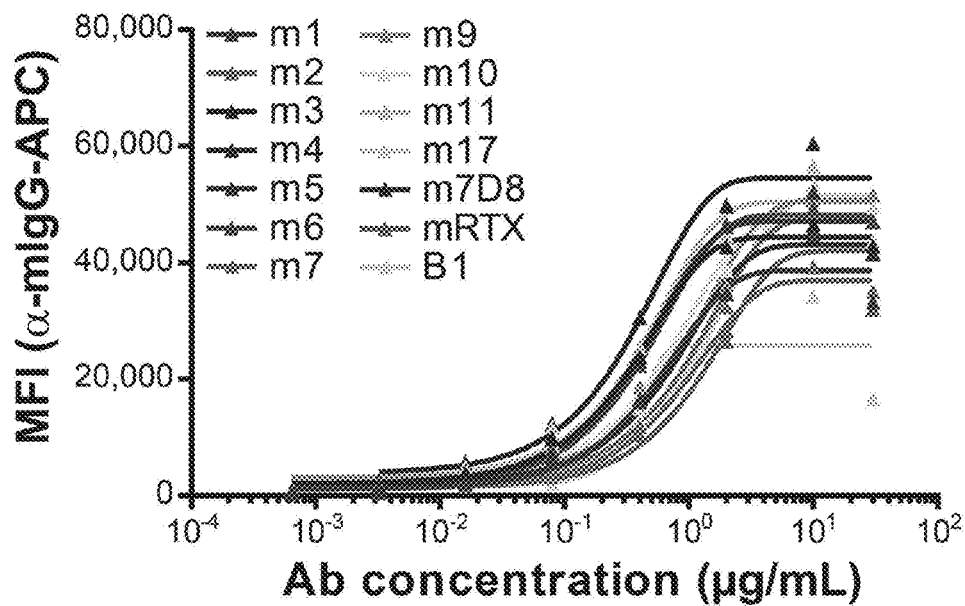

FIG. 19. Binding of mIgG-CD20 mAbs to Daudi cells.

Figure 20:
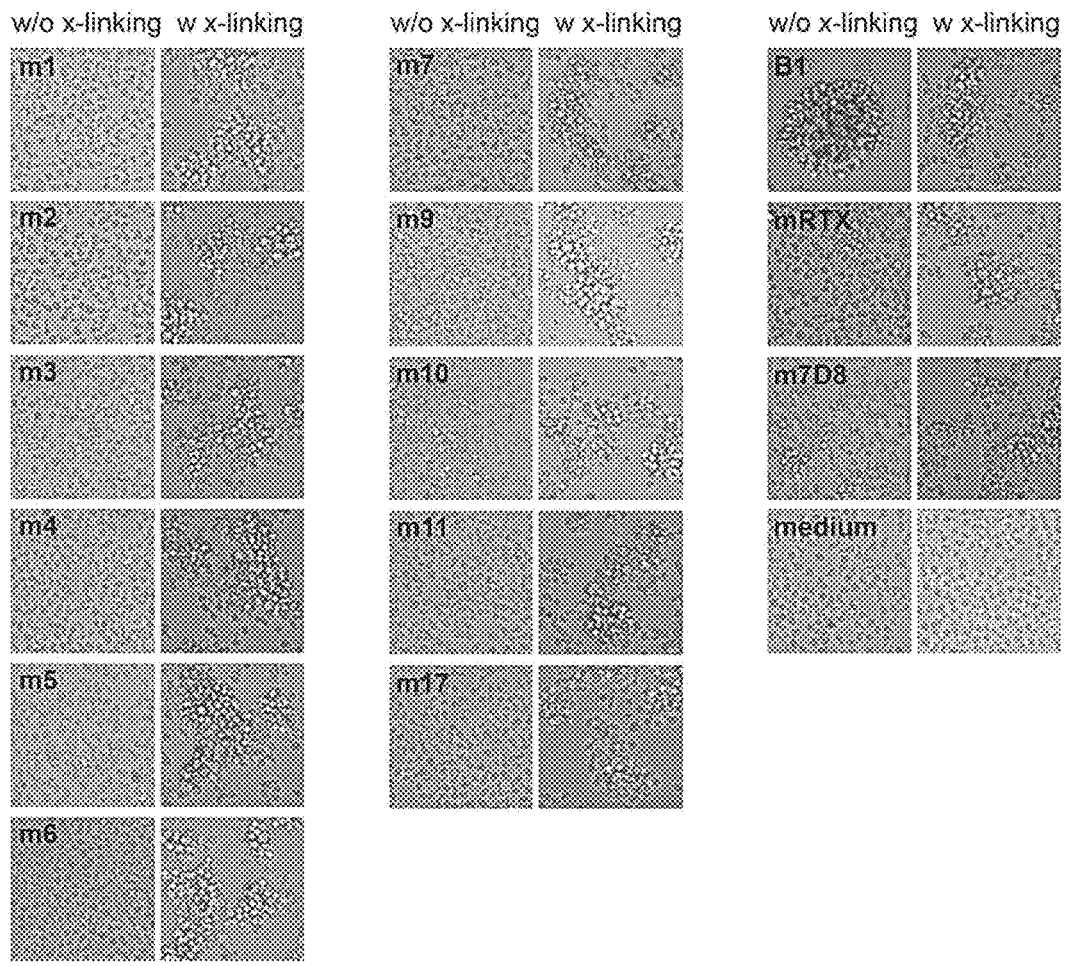

FIG. 20. No induction of HA of EL4-CD20 cells by new CD20 mAbs (1 µg/mL) (20× magnification). Cross-linking Ab (50 µg/mL) was added as positive control conditions. B1 as positive control (Type II).

Figure 21A:
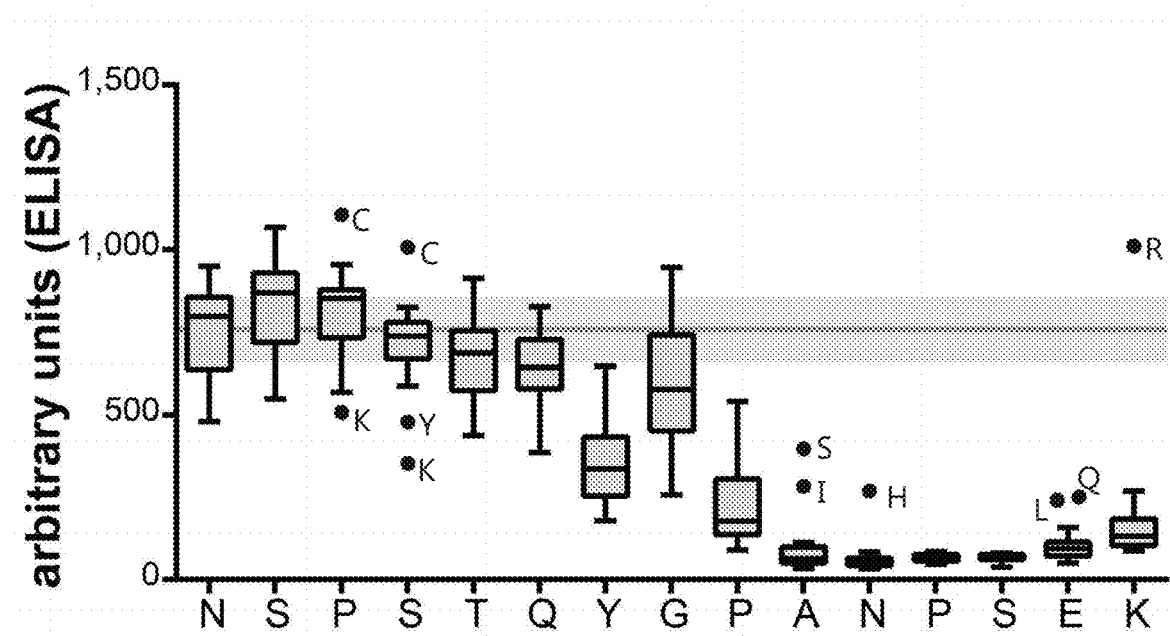
Figure 21B:
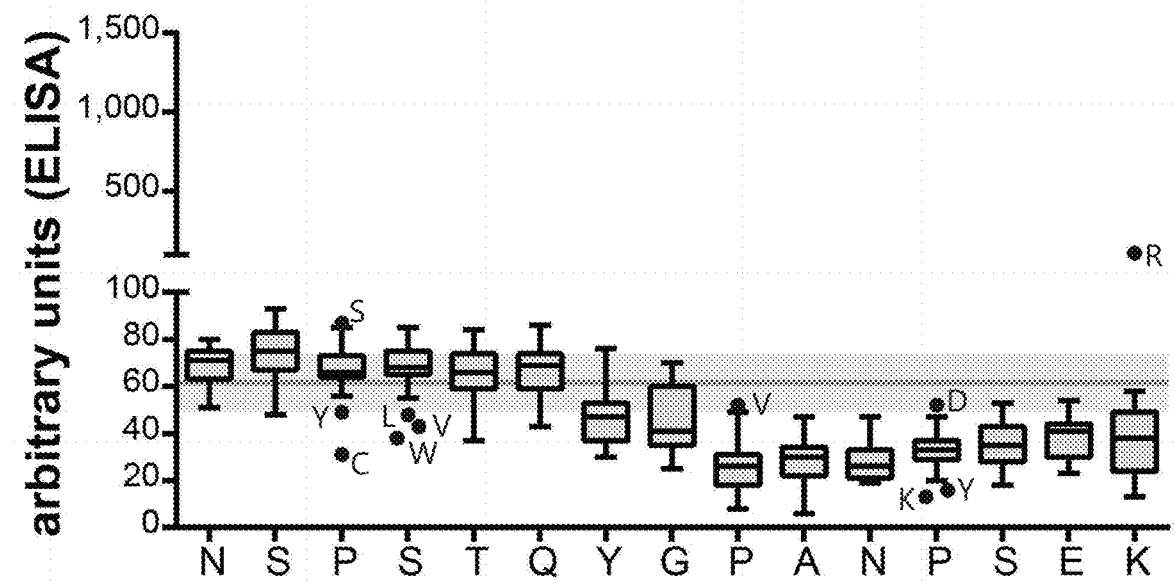

FIGS. 21A, 21B. Epitope mapping using the linear peptide NSPSTQYGPANPSEK (SEQ ID NO:20) resulted in identification of aa contributing to binding of (FIG. 21A) m1 but not (FIG. 21B) m2. Binding of 1 µg/mL mAb to the peptide and corresponding mutants with each aa replaced with all other available (positional scan; excluding cysteine) was determined by ELISA. Grey line and shaded area=WT binding±SEM; Results are displayed with Tukey-whiskers.

FIGS. 22A-22D. (FIGS. 22A, 22B) FACS based dissociation analysis. Daudi cells were stained with 10 µg/mL Alexa647-labeled CD20 mAb. Cells were left in (FIG. 22A) RPMI culture medium (non-competitive) or (FIG. 22B) the presence of a 10-fold excess of unlabeled mAb (100 µg/mL; competitive). At indicated time points the level of cell-bound mAb was determined. (FIG. 22C, FIG. 22D) Real-time binding and dissociation curve to SKBR3-CD20 cells using the Ligand Tracer technology. Association of 10 nM FITC-labeled CD20 mAbs was monitored for 4 hours before following the dissociation for 8 hours in the presence of (FIG. 22C) RPMI culture medium (non-competitive) or (FIG. 22D) 100 nM unlabeled CD20 mAbs of the same clone (competitive).

Figure 23:
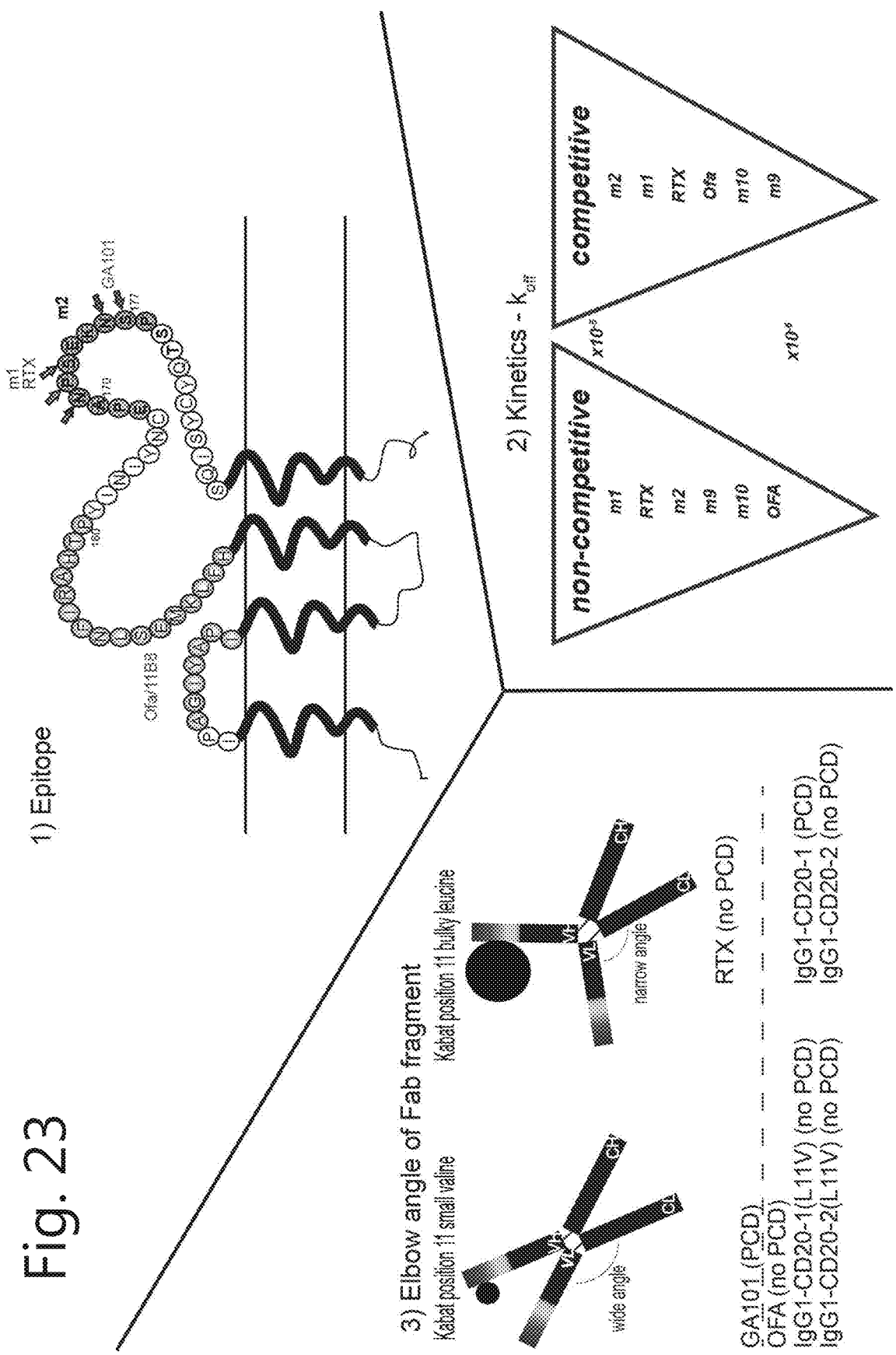

FIG. 23. Summarizing overview of molecular determinants of existing and novel CD20 mAbs. Three distinct molecular determinants were described to determine the MoA of CD20 mAbs: 1) epitope (positions of several CD20 antibodies are indicated); 2) kinetics ($k_{off}$ of the CD20 antibodies were ranked from high ($10^{-5}$) to low ($10^{-6}$), and 3) elbow angle (commercially available CD20 mAbs (OFA, RTX and OBZ) were grouped in wide and narrow angle according to literature. The amino acid at Kabat position 11 was described to influence the angle, and based on this, the new chimeric mAbs were ordered according to the residue).

FIG. 24. Amino acid sequence of suitable IgG1, IgA1 and IgA2 heavy and light chain constant regions.

SEQ ID NO:3 Heavy chain IgG1 constant region CH1-3 and Hinge

SEQ ID NO:4 Heavy chain IgA1 constant region CH1-3 and Hinge

SEQ ID NO:5 Heavy chain IgA2 constant region CH1-3 and Hinge

SEQ ID NO:6 light chain constant region

FIG. 25. Internalization of CD20 from B cells at 1 ug of antibody. The number in the UMAB . . . reference in the figures refer to the variable domains of antibody m . . . with the respective numbers and the constant region as indicated.

FIGS. 26.1, 26.2, and 26.3. Titration range of antibodies in CD20 internalization of B cells.

Figure 27A:
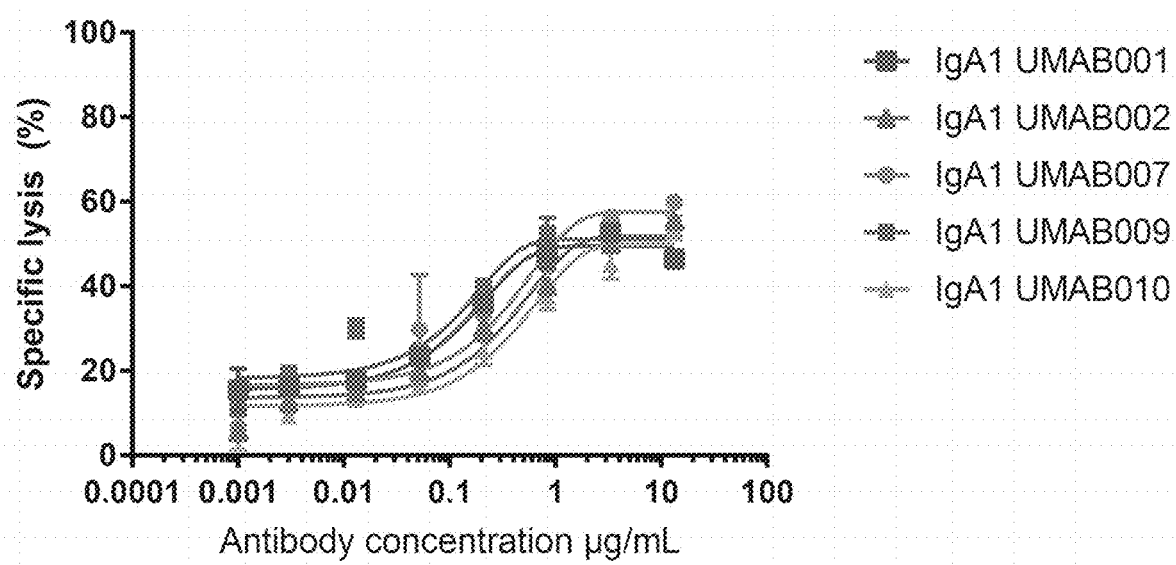
Figure 27B:
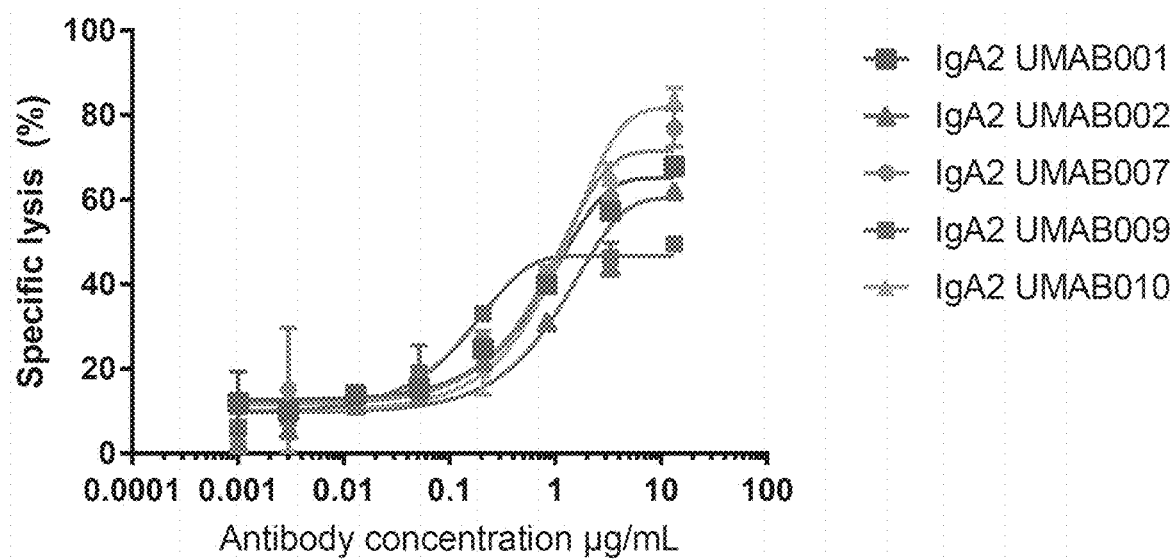

FIGS. 27A, 27B. Analysis of in vitro efficacy of new chimeric IgA-CD20 mAbs. (FIG. 27A) ADCC of IgA1-CD20 antibodies: Specific lysis of Daudi cells in a chromium release assay with PMNs as effector cells (E:T=40:1). (FIG. 27B) ADCC of IgA2-CD20 antibodies: Specific lysis of Daudi cells in a chromium release assay with PMNs as effector cells (E:T=40:1).

Figure 28A:
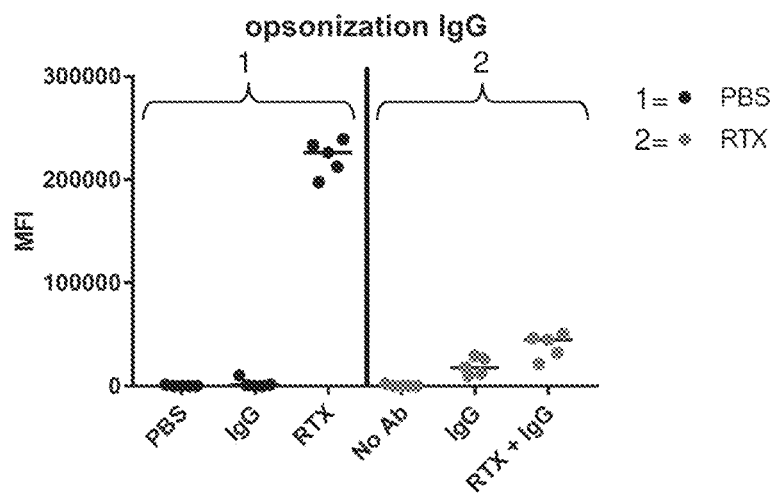
Figure 28B:
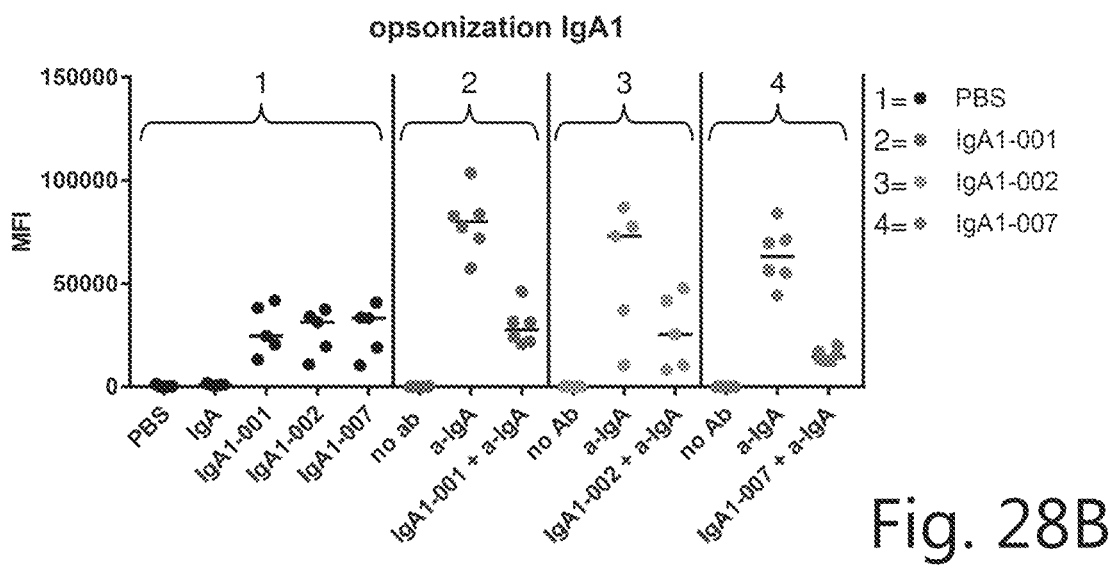
Figure 28C:
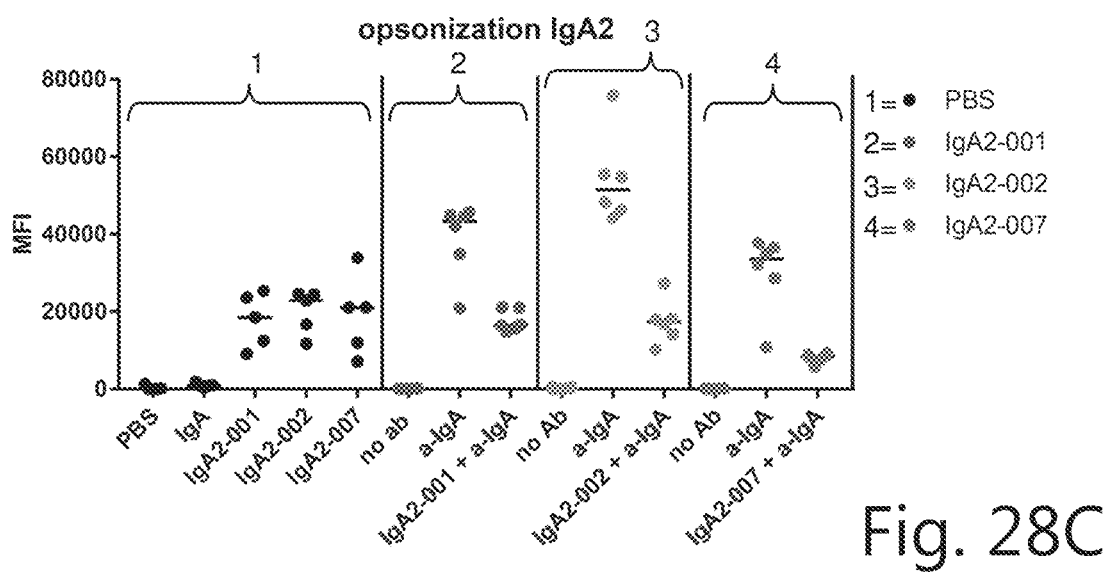

FIGS. 28A-28C. In vivo efficacy of IgA-CD20 mAbs. C57BL/6 mice (6 mice/group) were injected intraperitoneally with 5×10e5 CellTraceViolet labeled EL4-CD20 cells 16 hours prior to mAb (10 µg) or PBS treatment. The anti-tumor response was evaluated 24 hours later by determining the amount of remaining tumor cells in the peritoneal lavage with TruCount tubes (median±interquartile range).

Figure 29:
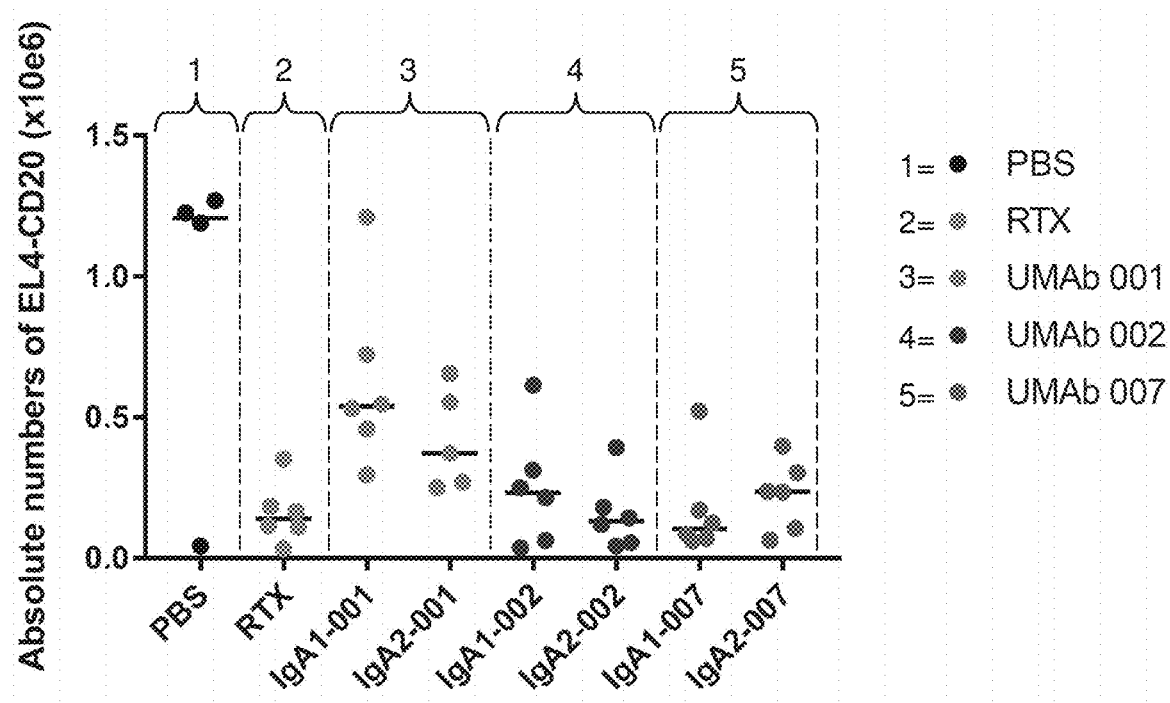

FIG. 29. Loss of CD20 expression occurs after IgG treatment, but not after IgA treatment in vivo. C57BL/6 mice (6 mice/group) were injected intraperitoneally with 5×10e5 CellTraceViolet labeled EL4-CD20 cells 16 hours prior to mAb (10 µg) or PBS treatment. Subsequently, CD20 expression was determined on these cells by flow cytometric analysis.

Figure 30:
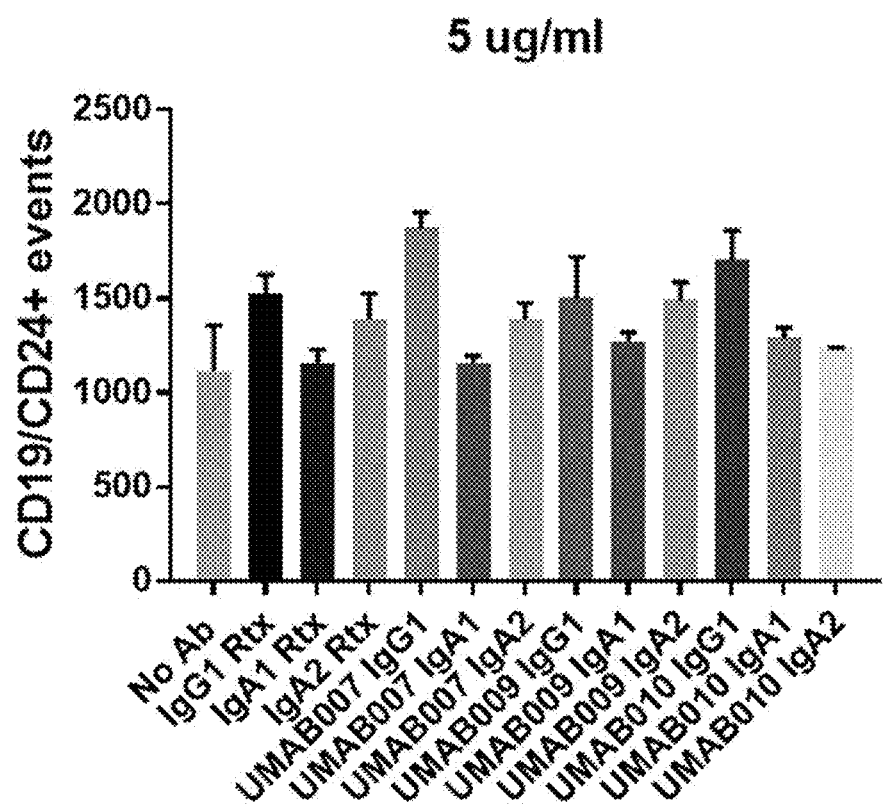

FIG. 30. CD19/CD24+ events with antibodies having a variable domain of the indicated antibody and the indicated constant regions, IgG1, IgA1 or IgA2.

DETAILED DESCRIPTION

The disclosure is concerned with antibodies that bind CD20. The CD20 protein is also known under various other names such as Membrane Spanning 4-Domains A1; MS4A1; Membrane-Spanning 4-Domains Subfamily A Member 1; Leukocyte Surface Antigen Leu-16; CD20 Antigen; Bp35; B-Lymphocyte Cell-Surface Antigen B1; B-Lymphocyte Surface Antigen B1; CD20 Receptor; LEU-16; CVID5; MS4A2; B1; and S7. External Ids for MS4A1 are HGNC: 7315; Entrez Gene: 931; Ensembl: ENSG00000156738; OMIM: 112210 and UniProtKB: P11836.

Some of the names may or may not have also been used to refer to other proteins than CD20. The names and sequence identifiers are given for reference purposes only. An antibody of the disclosure binds to CD20 as expressed on Ramos cells but also to other CD20 molecules as long as the epitope to which the antibody binds is available. Thus splicing variants or mutant CD20 molecules (if any) will also be bound by an antibody of the disclosure as long as the epitope is available. The fact that the antibody binds to CD20 means that the antibody can bind to CD20 and does not imply that the antibody is actually bound to CD20. It also does not mean that the antibody does not bind to other proteins. Such cross-reactivity is at present not known for an antibody of this disclosure, however, it is not expressly excluded that such cross-reactivity may exist.

An antibody (Ab), also known as an immunoglobulin (Ig), is a large, typically Y-shaped protein. An antibody interacts with various components of the immune system. Some of the interactions are mediated by its Fc region (located at the base of the "Y"), which contains site(s) involved in these interactions.

Antibodies are proteins belonging to the immunoglobulin superfamily. They typically have two heavy chains and two light chains. There are several different types of antibody heavy chains that define the five different types of crystallisable fragments (Fc) that may be attached to the antigen-binding fragments. The five different types of Fc regions allow antibodies to be grouped into five isotypes. An Fc region of a particular antibody isotype is able to bind to its specific Fc receptor (FcR) thus allowing the antigen-antibody complex to mediate different roles depending on which FcR it binds. The ability of an IgG antibody to bind to its corresponding FcR is modulated by the presence/absence of interaction sites and the structure of the glycan(s) (if any) present at sites within its Fc region. The ability of antibodies to bind to FcRs helps to direct the appropriate immune response for each different type of foreign object they encounter.

Though the general structure of all antibodies is similar, a region at the tip of the protein is extremely variable, allowing millions of antibodies with slightly different tip structures, or antigen-binding sites, to exist. This region is known as the hypervariable region. The enormous diversity of antigen binding by antibodies is largely defined by the hypervariable region and the variable domain containing the hypervariable region.

An antibody of the disclosure is typically a full-length antibody. The term "full length antibody" is defined as comprising an essentially complete immunoglobulin molecule, which however does not necessarily have all functions of an intact immunoglobulin. For the avoidance of doubt, a full length antibody has two heavy and two light chains. Each chain contains constant (C) and variable (V) regions. A heavy chain of a full length antibody typically comprises a CH1, a CH2, a CH3, a VH region and a hinge region. A light chain of a full length antibody typically comprises a CL region and a VL region.

An antibody binds to antigen via the variable region domains contained in the Fab portion. An antibody variable domain comprises a heavy chain variable region and a light chain variable region. Full length antibodies according to the disclosure encompass heavy and light chains wherein mutations may be present that provide desired characteristics. Full length antibodies should not have deletions of substantial portions of any of the regions. However, IgG molecules wherein one or several amino acid residues are substituted, inserted, deleted or a combination thereof, without essentially altering the antigen binding characteristics of the resulting antibody, are embraced within the term "full length" antibody. For instance, a "full length" antibody can have a substitution, insertion, deletion or a combination thereof, of between 1 and 10 (inclusive) amino acid residues, preferably in non-CDR regions, wherein the deleted amino acids are not essential for the binding specificity of the antibody.

The epitope that is recognized by an antibody of the disclosure, and/or minor contributing amino acids therein were determined by, among others, positional amino acid scan wherein the amino acid was replaced by every other natural amino acid in a peptide containing the epitope and by a mutant screen of the CD20 protein expressed on cells. The contribution of an amino acid to the binding of an antibody to an epitope is preferably determined by comparing the binding to a peptide comprising the epitope as such and the same peptide but with an alanine at the position of the analyzed amino acid. An amino acid is relevant to the binding of the antibody to the protein when a replacement with an alanine in the protein results in a decrease of binding of the antibody to 0-70% relative to the unmodified protein. This is also referred to a reduction of binding. A decrease to 0-20% if the binding relative to the unmodified protein is regarded as loss of binding and a decrease to 21-70% relative to the unmodified protein is regarded as intermediate binding. The thus identified amino acids are considered to be a major contributor or an intermediate contributor to the binding of the antibody to the protein. A binding of 71-100% was regarded as full binding. The amino acid concerned is not regarded to contribute significantly to the binding of the antibody to the protein.

One of the antibodies provided by the disclosure is an antibody (A) comprising a mouse IgG2; a human IgG1, IgA1 or IgA2 constant region and a variable domain that can bind the epitope "EPANpSEK" (SEQ ID NO:31) on human CD20 expressed on Ramos cells and which antibody has an increased PCD functionality when compared to Rituximab with a constant region of the same isotype. The antibody preferably further comprises a comparable or an increased CDC functionality when compared to Rituximab with a constant region of the same isotype. Preferably the ADCC functionality of the antibody is comparable or reduced when compared to Rituximab with a constant region of the same isotype. The epitope on CD20 that is bound by the antibody is "EPANpSEK" (SEQ ID NO:31). A capital letter, small case letter and bold indicates the relevance of the amino acid for binding of the antibody to the peptide. A bold letter indicates that the amino acid is a major contributor to the binding of the antibody; a small case letter indicates that the amino acid has an intermediate contribution to the binding and a capital letter in plain text indicates that the amino acid has a small or not detectable contribution to the binding of the antibody to the peptide. The antibody binds 20% or less to a CD20 protein wherein one or more of the amino acids N or S in "EPANpSEK" (SEQ ID NO:31) have been replaced by an alanine, where the binding is compared to the binding of the antibody an unmodified CD20 protein.

Also provided is an antibody (A1) that can bind to an extracellular part of human CD20 expressed on Ramos cells comprising a variable domain with a heavy chain variable region and a light chain variable region, wherein the heavy chain variable region comprises a CDR3 region with the sequence SNSYGSTYWYFDV (SEQ ID NO:21). The antibody (A1) has an increased PCD functionality when compared to Rituximab with a constant region of the same isotype. The antibody preferably further comprises a comparable or an increased CDC functionality when compared to Rituximab with a constant region of the same isotype. Preferably the ADCC functionality of the antibody is comparable or reduced when compared to Rituximab with a constant region of the same isotype. The heavy chain variable region preferably comprises a CDR1, CDR2 and CDR3 region with the sequence SYNLH (SEQ ID NO:26), AIYPGNGDTSYNQKFKG (SEQ ID NO:27) and SNSYG-STYWYFDV (SEQ ID NO:21), respectively. Preferably the heavy chain variable region comprises the sequence of SEQ ID NO:1, with 0-5 amino acid insertions, deletions, substitutions, additions or a combination thereof at one or more positions other than positions of the amino acids that constitute the CDR1, CDR2 and CDR3 regions, wherein SEQ ID NO:1 has the sequence

```
QAYLQ QSGAE LVRPG ASVKM SCKAS GYTFT SYNLH WVKQT

PRQGL EWIGA IYPGN GDTSY NQKFK GKATL TVDKS SSTAY

MQLSR LTSED SAVYF CARSN SYGST YWYFD VWGTG TTVTV

SS.
```

The light chain variable region of the antibody (A1) preferably comprises the sequence of SEQ ID NO:2, with 0-5 amino acid insertions, deletions, substitutions, additions or a combination thereof at one or more positions other than positions of the amino acids that constitute the CDR1, CDR2 and CDR3 regions, wherein SEQ ID NO:2 has the sequence

```
QIVLS QSPAV LFASP GEKVT MTCRA RSSVS YMDWY QQKPR
SSPKP WIYAT SNLAS GVPAR FSGSG SGTSY SLTIS RVEAE
DAATY YCQQW TSNPP TFGSG TKLEI KRADA APTVS IFPPS
S.
```

The antibody A1 preferably comprises a mouse IgG2; a human IgG1, IgG2, IgG3, IgG4, IgM, IgE, IgA heavy chain constant region or a combination thereof. Preferably it comprises a human IgG1, IgG2, IgA1 or IgA2 heavy chain constant region or a combination thereof. Preferably it comprises a human IgG1 constant region. In a preferred embodiment, the heavy chain constant region is a human IgA1 or human IgA2 heavy chain constant region, preferably a human IgA2; more preferably a human IgA2m, preferably an IgA2m1 or IgA2m2, preferably IgA2m1 heavy chain constant region. In another preferred embodiment, the antibody comprises a murine IgG2 region, preferably a IgG2c constant region.

In a preferred embodiment, the antibody A is an A1 antibody.

The antibody A or A1 preferably comprises a heavy chain and a light chain wherein the heavy chain comprises the sequence of SEQ ID NO:1 and the sequence of SEQ ID NO:3, 4 or 5 with 0-15 amino acid insertions, deletions, substitutions, additions or a combination thereof at one or more positions other than positions of the amino acids that constitute the CDR1, CDR2 and CDR3 regions.

The antibody A or A1 preferably comprises a light chain comprising the sequence of SEQ ID NO:2 and the sequence of SEQ ID NO:6 with 0-15 amino acid insertions, deletions, substitutions, additions or a combination thereof at one or more positions other than positions of the amino acids that constitute the CDR1, CDR2 and CDR3 regions.

The disclosure also provides an antibody (B) comprising a mouse IgG2; a human IgG1, IgA1 or IgA2 constant region and a variable domain that can bind the epitope "EPANPsEK" (SEQ ID NO:31) on human CD20 expressed on Ramos cells and which antibody has an increased ADCC functionality when compared to Rituximab a constant region of the same isotype. The epitope in CD20 that is bound by the antibody is "EPANPsEK" (SEQ ID NO:31). A capital letter, small case letter and bold indicates the relevance of the amino acid for binding of the antibody to the peptide. A bold letter indicates that the amino acid is a major contributor to the binding of the antibody; a small case letter indicates that the amino acid has an intermediate contribution to the binding and a capital letter in plain text indicates that the amino acid has a small or not detectable contribution to the binding of the antibody to the peptide. The antibody binds 20% or less to a CD20 protein wherein the amino acid N in "EPANpsEK" (SEQ ID NO:31) has been replaced by an alanine, whereby the binding is compared to the binding of the antibody an unmodified CD20 protein.

Also provided is an antibody (B1) that can bind to an extracellular part of human CD20 expressed on Ramos cells, the antibody comprising a variable domain with a heavy chain variable region and a light chain variable region, wherein the heavy chain variable region comprises a CDR3 region with the sequence YYYGSSYGAMDY (SEQ ID NO:22). The antibody B1 has an increased ADCC functionality when compared to Rituximab with the same isotype constant region. The heavy chain variable region preferably comprises a CDR1, CDR2 and CDR3 region with the sequence SYNMH (SEQ ID NO:28), GIYPGNGDTSYN-QKFKG (SEQ ID NO:29) and YYYGSSYGAMDY (SEQ ID NO:22), respectively.

Preferably, the heavy chain variable region comprises the sequence of SEQ ID NO:7, with 0-5 amino acid insertions, deletions, substitutions, additions or a combination thereof at one or more positions other than positions of the amino acids that constitute the CDR1, CDR2 and CDR3 regions, wherein SEQ ID NO:7 has the sequence

```
QAYLQ QSGAE LVRPG ASVKM SCKAS GYTFT SYNMH WVKQT
PRQGL EWIGG IYPGN GDTSY NQKFK GKATL TVDKS SSTAY
MQLSS LTSED SAVYF CARYY YGSSY GAMDY WGQGT SVTVS
S.
```

The light chain variable region of the antibody B1 preferably comprises the sequence of SEQ ID NO:8, with 0-5 amino acid insertions, deletions, substitutions, additions or a combination thereof at one or more positions other than positions of the amino acids that constitute the CDR1, CDR2 and CDR3 regions, wherein SEQ ID NO:8 has the sequence

```
QIVLS QSPAI LSASP GEKVT MTCRA SSSVS YMHWY QQKPG
SSPKP WIYAT SNLAS GVPAR FSGSG SGTSY SLTIS RVEAA
DAATY YCHQW TFNPP TFGGG TKLEI KRADA APTVS IFPPS
S.
```

The antibody B1 preferably comprises a mouse IgG2; a human IgG1, IgG2, IgG3, IgG4, IgM, IgE, IgA heavy chain constant region or a combination thereof. Preferably, it comprises a mouse IgG2; a human IgG1, IgG2, IgA1 or IgA2 heavy chain constant region or a combination thereof. Preferably it comprises a human IgG1 constant region. In a preferred embodiment, the heavy chain constant region is a human IgA1 or human IgA2 heavy chain constant region, preferably a human IgA2; more preferably a human IgA2m, preferably an IgA2m1 or IgA2m2, preferably IgA2m1 heavy chain constant region. In another preferred embodiment, the antibody comprises a murine IgG2 region, preferably a IgG2c constant region.

In a preferred embodiment, the antibody B is a B1 antibody.

The antibody B or B1 preferably comprises a heavy chain and a light chain wherein the heavy chain comprises the sequence of SEQ ID NO:7 and the sequence of SEQ ID NO:3, 4 or 5 with 0-15 amino acid insertions, deletions, substitutions, additions or a combination thereof at one or more positions other than positions of the amino acids that constitute the CDR1, CDR2 and CDR3 regions.

The antibody B or B1 preferably comprises a light chain comprising the sequence of SEQ ID NO:8 and the sequence of SEQ ID NO:6.with 0-15 amino acid insertions, deletions, substitutions, additions or a combination thereof at one or more positions other than positions of the amino acids that constitute the CDR1, CDR2 and CDR3 regions.

The disclosure also provides an antibody (C) comprising a mouse IgG2; a human IgG1, IgA1 or IgA2 constant region and a variable domain that can bind the epitope "EPANpsEK" (SEQ ID NO:31) on human CD20 expressed on Ramos cells and which antibody has an increased CDC functionality when compared to Rituximab with a constant region of the same isotype. Preferably it comprises similar ADCC functionality as Rituximab with a constant region of the same isotype. The epitope in CD20 that is bound by the antibody is "EPANpsEK" (SEQ ID NO:31). A capital letter, small case letter and bold indicates the relevance of the amino acid for binding of the antibody to the peptide. A bold letter indicates that the amino acid is a major contributor to the binding of the antibody; a small case letter indicates that the amino acid has an intermediate contribution to the binding and a capital letter in plain text indicates that the amino acid has a small or not detectable contribution to the binding of the antibody to the peptide. The antibody binds 20% or less to a CD20 protein wherein the amino acid N in "EPANpSEK" (SEQ ID NO:31) has been replaced by an alanine, whereby the binding is compared to the binding of the antibody an unmodified CD20 protein.

Also provided is an antibody (C1) that can bind to an extracellular part of human CD20 expressed on Ramos cells comprising a variable domain with a heavy chain variable region and a light chain variable region, wherein the heavy chain variable region comprises a CDR3 region with the sequence TYYYGSSPYWSFDV (SEQ ID NO:23). The antibody has an increased CDC functionality when compared to Rituximab with a constant region of the same isotype. Preferably it comprises a similar ADCC functionality as Rituximab with a constant region of the same isotype. The heavy chain variable region preferably comprises a CDR1, CDR2 and CDR3 region with the sequence SYNMH (SEQ ID NO:28), AIYPGNGDTSYNQKFKG (SEQ ID NO:27) and TYYYGSSPYWSFDV (SEQ ID NO:23), respectively.

Preferably the heavy chain variable region comprises the sequence of SEQ ID NO:9, with 0-5 amino acid insertions, deletions, substitutions, additions or a combination thereof at one or more positions other than positions of the amino acids that constitute the CDR1, CDR2 and CDR3 regions, wherein SEQ ID NO:9 has the sequence

QAYLQ QSGAE LVRPG ASVKM SCKAS GYTFA SYNMH WIKQT

PRQGL EWIAA IYPGN GDTSY NQKFK GKATL TVDKS SSTAY

MQLSS LTSED SAVYF CARTY YYGSS PYWSF DVWGT GTTVT

VSS.

The light chain variable region of the antibody C1 preferably comprises the sequence of SEQ ID NO:10, with 0-5 amino acid insertions, deletions, substitutions, additions or a combination thereof at one or more positions other than positions of the amino acids that constitute the CDR1, CDR2 and CDR3 regions, wherein SEQ ID NO:10 has the sequence

DIQMT QSPAS LSASV GETVT VTCGA SYNIY GALNW YQRKQ

GKSPQ LLIYG ATNLA DGMSS RFSGS GSGRQ YSLKI SSLHP

DDVAT YYCQN VLSNP PTFGG GTKLE IKRAD AAPTV SIFPP

SS.

The antibody C1 preferably comprises a mouse IgG2, a human IgG1 IgG2, IgG3, IgG4, IgM, IgE, IgA heavy chain constant region or a combination thereof. Preferably, it comprises a human IgG1, IgG2, IgA1 or IgA2 heavy chain constant region or a combination thereof. Preferably it comprises a human IgG1 constant region. In a preferred embodiment, the heavy chain constant region is a human IgA1 or human IgA2 heavy chain constant region, preferably a human IgA2; more preferably a human IgA2m, preferably an IgA2m1 or IgA2m2, preferably IgA2m1 heavy chain constant region. In another preferred embodiment, the antibody comprises a murine IgG2 region, preferably a IgG2b constant region.

In a preferred embodiment, the antibody C is a C1 antibody.

The antibody C or C1 preferably comprises a heavy chain and a light chain wherein the heavy chain comprises the sequence of SEQ ID NO:9 and the sequence of SEQ ID NO:3, 4, or 5 with 0-15 amino acid insertions, deletions, substitutions, additions or a combination thereof at one or more positions other than positions of the amino acids that constitute the CDR1, CDR2 and CDR3 regions.

The antibody C or C1 preferably comprises a light chain comprising the sequence of SEQ ID NO:10 and the sequence of SEQ ID NO:6 with 0-15 amino acid insertions, deletions, substitutions, additions or a combination thereof at one or more positions other than positions of the amino acids that constitute the CDR1, CDR2 and CDR3 regions.

Also provided is an antibody D1 that can bind to an extracellular part of human CD20 expressed on Ramos cells comprising a variable domain with a heavy chain variable region and a light chain variable region, wherein the heavy chain variable region comprises a CDR3 region with the sequence SRLFDSSYGWYFDV (SEQ ID NO:24). The antibody has an increased CDC and/or increased ADCC functionality when compared to Rituximab with a constant region of the same isotype. Preferably it comprises an improved ADCC functionality as Rituximab with a constant region of the same isotype. The heavy chain variable region preferably comprises a CDR1, CDR2 and CDR3 region with the sequence SYNMH (SEQ ID NO:28), AIYPGNGDT-SYNQKFKG (SEQ ID NO:27) and SRLFDSSYGWYFDV (SEQ ID NO:24), respectively.

Preferably the heavy chain variable region comprises the sequence of SEQ ID NO:11, with 0-5 amino acid insertions, deletions, substitutions, additions or a combination thereof at one or more positions other than positions of the amino acids that constitute the CDR1, CDR2 and CDR3 regions, wherein SEQ ID NO:11 has the sequence

QAYLQ QSGAE LVRPG ASVKM SCKAS GYTFP SYNMH WVKQT

PRQGL EWIGA IYPGN GDTSY NQKFK GKASQ TVDKS SSTVY

MQLSS LTSAD SAVYF CARSR LFDSS YGWYF DVWGT GTTVT

VSS.

The light chain variable region of the antibody D1 preferably comprises the sequence of SEQ ID NO:12, with 0-5 amino acid insertions, deletions, substitutions, additions or a combination thereof at one or more positions other than positions of the amino acids that constitute the CDR1, CDR2 and CDR3 regions, wherein SEQ ID NO:12 has the sequence

QIVLS QSPAI LSAYP GEKVT MTCRA RSSVS YIDWY QQKAG

SSPKP WIYAT SNLAS GVPAR FSGSG SGTSY SLTIS RVEAE

DAATY YCQQW TSNPP TFGGG TKLEI KRADA APTVS IFPPS

S.

The antibody D1 preferably comprises a mouse IgG2; a human IgG1, IgG2, IgG3, IgG4, IgM, IgE, IgA heavy chain constant region or a combination thereof. Preferably, it comprises a human IgG1, IgG2, IgA1 or IgA2 heavy chain constant region or a combination thereof. Preferably it comprises a human IgG1 constant region. In a preferred embodiment, the heavy chain constant region is a human IgA1 or human IgA2 heavy chain constant region, preferably a human IgA2; more preferably a human IgA2m, preferably an IgA2m1 or IgA2m2, preferably IgA2m1 heavy chain constant region. In another preferred embodiment, the antibody comprises a murine IgG2 region, preferably a IgG2c constant region.

In a preferred embodiment, the antibody D is a D1 antibody.

The antibody D or D1 preferably comprises a heavy chain and a light chain wherein the heavy chain comprises the sequence of SEQ ID NO:11 and the sequence of SEQ ID NO:3, 4, or 5 with 0-15 amino acid insertions, deletions, substitutions, additions or a combination thereof at one or more positions other than positions of the amino acids that constitute the CDR1, CDR2 and CDR3 regions.

The antibody D or D1 preferably comprises a light chain with the sequence of SEQ ID NO:12 and the sequence of SEQ ID NO:6 with 0-15 amino acid insertions, deletions, substitutions, additions or a combination thereof at one or more positions other than positions of the amino acids that constitute the CDR1, CDR2 and CDR3 regions.

The disclosure also provides an antibody (E) comprising a mouse IgG2; a human IgG1, IgA1 or IgA2 constant region and a variable domain that can bind the epitope "EPANpSEK" (SEQ ID NO:31) on human CD20 expressed on Ramos cells and which antibody has an increased CDC and/or increased ADCC functionality when compared to Rituximab with a constant region of the same isotype. The epitope in CD20 that is bound by the antibody is "EPANpSEK" (SEQ ID NO:31). A capital letter, small case letter and bold indicates the relevance of the amino acid for binding of the antibody to the peptide. A bold letter indicates that the amino acid is a major contributor to the binding of the antibody; a small case letter indicates that the amino acid has an intermediate contribution to the binding and a capital letter in plain text indicates that the amino acid has a small or not detectable contribution to the binding of the antibody to the peptide. The antibody binds 20% or less to a CD20 protein wherein one or more of the amino acids N or S in "EPANpSEK" (SEQ ID NO:31) have been replaced by an alanine, where the binding is compared to the binding of the antibody an unmodified CD20 protein.

Also provided is an antibody (E1) that can bind to an extracellular part of human CD20 expressed on Ramos cells comprising a variable domain with a heavy chain variable region and a light chain variable region, wherein the heavy chain variable region comprises a CDR3 region with the sequence SAYYGSNVWFFDV (SEQ ID NO:25). The antibody has an increased CDC and/or increased ADCC functionality when compared to Rituximab with a constant region of the same isotype. The heavy chain variable region preferably comprises a CDR1, CDR2 and CDR3 region with the sequence SYNLH (SEQ ID NO:26), AIYPGNGDTSYNQKFKG (SEQ ID NO:27) and SAYYGSNVWFFDV (SEQ ID NO:25), respectively.

Preferably the heavy chain variable region comprises the sequence of SEQ ID NO:13, with 0-5 amino acid insertions, deletions, substitutions, additions or a combination thereof at one or more positions other than positions of the amino acids that constitute the CDR1, CDR2 and CDR3 regions, where SEQ ID NO:13 has the sequence

```
QAYLQ QSGAD LVRPG ASVKM SCKAS GFTFP SYNLH WVKQT

PRQGL EWIGA IYPGN GDTSY NQKFK GKATL TVDKS SSTAY

MQLSS LTSED SAVYF CARSA YYGSN VWFFD VWGTG TTVTV

SS.
```

The light chain variable region of antibody E1 preferably comprises the sequence of SEQ ID NO:14, with 0-5 amino acid insertions, deletions, substitutions, additions or a combination thereof at one or more positions other than positions of the amino acids that constitute the CDR1, CDR2 and CDR3 regions, wherein SEQ ID NO:14 has the sequence

```
QIVLS QSPAI LSASP GEKVT MTCRA SSSVS YMDWY QQKPG

SSPKP WIYAT SNLAS GVPTR FSGSG SGTSY SLTIS RVEAE

DAATY YCQQW ISNPP TFGAG TKLDL KRADA APTVS IFPPS

S.
```

The antibody E1 preferably comprises a mouse IgG2; a human IgG1, IgG2, IgG3, IgG4, IgM, IgE, IgA heavy chain constant region or a combination thereof. Preferably, it comprises a human IgG1, IgG2, IgA1 or IgA2 heavy chain constant region or a combination thereof. Preferably it comprises a human IgG1 constant region. In a preferred embodiment, the heavy chain constant region is a human IgA1 or human IgA2 heavy chain constant region, preferably a human IgA2; more preferably a human IgA2m, preferably an IgA2m1 or IgA2m2, preferably IgA2m1 heavy chain constant region. In another preferred embodiment, the antibody comprises a murine IgG2 region, preferably an IgG2c constant region.

In a preferred embodiment, the antibody E is an E1 antibody.

The antibody E or E1 preferably comprises a heavy chain and a light chain wherein the heavy chain comprises the sequence of SEQ ID NO:13 and the sequence of SEQ ID NO:3, 4, or 5 with 0-15 amino acid insertions, deletions, substitutions, additions or a combination thereof at one or more positions other than positions of the amino acids that constitute the CDR1, CDR2 and CDR3 regions.

The antibody E or E1 preferably comprises a light chain with the sequence of SEQ ID NO:14 and the sequence of SEQ ID NO:6 with 0-15 amino acid insertions, deletions, substitutions, additions or a combination thereof at one or more positions other than positions of the amino acids that constitute the CDR1, CDR2 and CDR3 regions.

The functionality of an antibody can be compared to Rituximab with a constant region of the same isotype. This is preferably the same constant region. Some amino acid differences may be present in the constant regions, such amino acid differences can, for instance, be introduced by somatic cell hypermutation. Between 0-5 amino acid differences are typically allowed, although more is also possible. For a comparison of functionality it is preferred that the constant regions of antibody and rituximab are the same.

An antibody of the disclosure can have a heavy chain variable region with 0-5 amino acid insertions, deletions, substitutions, additions or a combination thereof at one or more positions with respect to the sequence indicated by the respective SEQ ID NO, wherein the one or more positions are not positions in the CDR1, CDR2 and CDR3 regions. The sequence of the CDRs is thus as indicated in the respective SEQ ID NO. It is preferred that the heavy chain variable region has 0-4 amino acid insertions, deletions, substitutions, additions or a combination thereof at one or more positions with respect to the sequence indicated by the respective SEQ ID NO, wherein the one or more positions are not positions in the CDR1, CDR2 and CDR3 regions. It is preferred that the heavy chain variable region has 0-3, more preferably 0-2, more preferably 0-1 amino acid insertions, deletions, substitutions, additions or a combination thereof at one or more positions with respect to the sequence indicated by the respective SEQ ID NO, wherein the one or more positions are not positions in the CDR1, CDR2 and CDR3 regions. In a preferred embodiment, a heavy chain variable region in the antibody of the disclosure has 0 amino acid insertions, deletions, substitutions, additions or a combination thereof with respect to the sequence of the SEQ ID NO indicated.

An antibody of the disclosure can have a light chain variable region with 0-5 amino acid insertions, deletions, substitutions, additions or a combination thereof at one or more positions with respect to the sequence indicated by the respective SEQ ID NO, wherein the one or more positions are not positions in the CDR1, CDR2 and CDR3 regions. The sequence of the CDRs is thus as indicated in the respective SEQ ID NO. It is preferred that the light chain variable region has 0-4 amino acid insertions, deletions, substitutions, additions or a combination thereof at one or more positions with respect to the sequence indicated by the respective SEQ ID NO, wherein the one or more positions are not positions in the CDR1, CDR2 and CDR3 regions. It is preferred that the light chain variable region has 0-3, more preferably 0-2, more preferably 0-1 amino acid insertions, deletions, substitutions, additions or a combination thereof at one or more positions with respect to the sequence indicate by the respective SEQ ID NO, wherein the one or more positions are not positions in the CDR1, CDR2 and CDR3 regions. In a preferred embodiment, a light chain variable region in the antibody of the disclosure has 0 amino acid insertions, deletions, substitutions, additions or a combination thereof with respect to the sequence of the SEQ ID NO indicated.

A heavy chain of an antibody of the disclosure can have 0-15 amino acid insertions, deletions, substitutions, additions or a combination thereof at one or more positions with respect to the sequence indicate by the respective SEQ ID numbers wherein the one or more positions are not positions in the CDR1, CDR2 and CDR3 regions. The sequence of the CDRs is thus as indicated in the respective SEQ ID NO. It is preferred that the heavy chain has 0-10, amino acid insertions, deletions, substitutions, additions or a combination thereof at one or more positions with respect to the sequence indicate by the respective SEQ ID numbers, wherein the one or more positions are not positions in the CDR1, CDR2 and CDR3 regions. The heavy chain can have 1, 2, 3, 4, 5, 6, 7, 8, 9, 10, 11, 12, 13, 14 and 15, amino acid insertions, deletions, substitutions, additions or a combination thereof at one or more positions with respect to the sequence indicate by the respective SEQ ID numbers, wherein the one or more positions are not positions in the CDR1, CDR2 and CDR3 regions. It is preferred that the heavy chain has 0-3, more preferably 0-2, more preferably 0-1 amino acid insertions, deletions, substitutions, additions or a combination thereof at one or more positions with respect to the sequence indicate by the respective SEQ ID numbers, wherein the one or more positions are not positions in the CDR1, CDR2 and CDR3 regions. In a preferred embodiment, the heavy chain in the antibody of the disclosure has 0 amino acid insertions, deletions, substitutions, additions or a combination thereof with respect to the sequence of the SEQ ID numbers indicated.

A light chain of an antibody of the disclosure can have 0-15 amino acid insertions, deletions, substitutions, additions or a combination thereof at one or more positions with respect to the sequence indicate by the respective SEQ ID numbers wherein the one or more positions are not positions in the CDR1, CDR2 and CDR3 regions. The sequence of the CDRs is thus as indicated in the respective SEQ ID NO. It is preferred that the light chain has 0-10, amino acid insertions, deletions, substitutions, additions or a combination thereof at one or more positions with respect to the sequence indicate by the respective SEQ ID numbers, wherein the one or more positions are not positions in the CDR1, CDR2 and CDR3 regions. The light chain can have 1, 2, 3, 4, 5, 6, 7, 8, 9, 10, 11, 12, 13, 14 and 15, amino acid insertions, deletions, substitutions, additions or a combination thereof at one or more positions with respect to the sequence indicate by the respective SEQ ID numbers, wherein the one or more positions are not positions in the CDR1, CDR2 and CDR3 regions. It is preferred that the light chain has 0-3, more preferably 0-2, more preferably 0-1 amino acid insertions, deletions, substitutions, additions or a combination thereof at one or more positions with respect to the sequence indicate by the respective SEQ ID numbers, wherein the one or more positions are not positions in the CDR1, CDR2 and CDR3 regions. In a preferred embodiment, the light chain in the antibody of the disclosure has 0 amino acid insertions, deletions, substitutions, additions or a combination thereof with respect to the sequence of the SEQ ID numbers indicated.

An antibody A, B, C, D, E, A1, B1, C1, D1, or E1 as described herein can be a bispecific antibody comprising one variable domain that binds an antigen other than the indicated epitope on an extracellular part of CD20 as expressed on Ramos cells. The other antigen is preferably CD19, CD64, CD32, CD16, CD3 and CD47. In a preferred embodiment, an antibody A, B, C, D, E, A1, B1, C1, D1, or E1 comprises two variable domains that each bind the same epitope on an extracellular part of CD20 as expressed on Ramos cells, wherein the epitope is as indicated for the variable domain of antibody A, B, C, D, E, A1, B1, C1, D1, or E1. The antibody A, B, C, D, E, A1, B1, C1, D1, or E1 preferably comprises two identical variable domains. The antibody A, B, C, D, E, A1, B1, C1, D1, or E1 preferably comprises two variable domains that each bind the same epitope and comprise the same VH and the same VL sequence.

The disclosure further provides a CAR-T receptor comprising a variable domain of an antibody A, B, C, D, E, A1, B1, C1, D1, or E1 as described herein. The variable domain comprises a heavy chain variable region and a variable light chain region of the respective antibodies, each with 0-5 amino acid insertions, deletions, substitutions, additions or a combination thereof at one or more positions other than positions of the amino acids that constitute the CDR1, CDR2 and CDR3 regions. The sequence of the respective heavy and light chain variable regions is indicated in FIG. 18.

For instance, a CAR-T receptor preferably comprises a variable domain of antibody A1. In a preferred embodiment, the variable domain comprises the amino acid sequence of the heavy and light chain variable regions of SEQ ID NOS:1 and 2, each with 0-5 amino acid insertions, deletions, substitutions, additions or a combination thereof at one or more positions other than positions of the amino acids that constitute the CDR1, CDR2 and CDR3 regions.

A CAR-T receptor preferably comprises a variable domain of antibody B1. In a preferred embodiment, the variable domain comprises the amino acid sequence of the heavy and light chain variable regions of SEQ ID NOS:7 and 8, each with 0-5 amino acid insertions, deletions, substitutions, additions or a combination thereof at one or more positions other than positions of the amino acids that constitute the CDR1, CDR2 and CDR3 regions.

A CAR-T receptor preferably comprises a variable domain of antibody C1. In a preferred embodiment, the variable domain comprises the amino acid sequence of the heavy and light chain variable regions of SEQ ID NOS:9 and 10, each with 0-5 amino acid insertions, deletions, substitutions, additions or a combination thereof at one or more positions other than positions of the amino acids that constitute the CDR1, CDR2 and CDR3 regions.

A CAR-T receptor preferably comprises a variable domain of antibody D1. In a preferred embodiment, the variable domain comprises the amino acid sequence of the heavy and light chain variable regions of SEQ ID NOS:11 and 12, each with 0-5 amino acid insertions, deletions, substitutions, additions or a combination thereof at one or more positions other than positions of the amino acids that constitute the CDR1, CDR2 and CDR3 regions.

A CAR-T receptor preferably comprises a variable domain of antibody E1. In a preferred embodiment, the variable domain comprises the amino acid sequence of the heavy and light chain variable regions of SEQ ID NOS:13 and 14, each with 0-5 amino acid insertions, deletions, substitutions, additions or a combination thereof at one or more positions other than positions of the amino acids that constitute the CDR1, CDR2 and CDR3 regions.

Also provided is a T-cell comprising a CAR-T cell receptor of the disclosure for use in adoptive cell transfer. The use is preferably for the treatment of an individual that has a CD20 positive neoplasm such as a CD20 positive B-cell lymphoma; hairy cell leukemia; B-cell chronic lymphocytic leukemia, or melanoma comprising administering to the individual in need thereof an antibody as described herein. It is also useful in the treatment of children with B-cell malignancies and pediatric leukemia patients that have a B-cell disease after stem cell transplantation.

A reason for changing an amino acid at a certain position can be immunogenicity. Other reasons include but are not limited to improving production or homogeneity of the antibody. Antibodies of the present disclosure have variable heavy and variable light chain regions derived from a murine background. Antibodies with such variable domains can be used in humans. Presently it is preferred to de-immunize such variable domains. De-immunization typically involves the modification of the murine sequence into a more human sequence whenever possible. Typically such modifications are directed toward removing one or more T-cell epitopes or one more B-cell epitopes from the variable domain. In a preferred embodiment, the disclosure provides an antibody A, B, C, D, E, A1, B1, C1, D1, or E1 wherein one or more (human) T-cell epitopes have been removed by replacement of at least one amino acid of the epitope with a different amino acid. Often it is sufficient to substitute the so-called "anchor" amino acid. Suitable replacement amino acids can be obtained from somatic cell hypermutants of the particular VH or VL. Replacement with an amino acid that is naturally present at that position in a human antibody is preferred. In a preferred embodiment, the disclosure provides an antibody A, B, C, D, E, A1, B1, C1, D1, or E1 wherein one or more (human) B-cell epitopes have been removed by replacement of at least one amino acid of the epitope with a different amino acid. Often it is sufficient to substitute only one amino acid of the epitope. Suitable replacement amino acids can be obtained from somatic cell hypermutants of the particular VH or VL. Replacement with an amino acid that is naturally present at that position in a human antibody is preferred. Preferably a variable domain of the disclosure is modified with respect to one or more exterior residues. Such residues are readily encountered by the immune system and are preferably selectively replaced with human residues to provide a hybrid molecule that comprises either a weakly immunogenic or substantially non-immunogenic surface. Suitable replacement amino acids can be obtained from somatic cell hypermutants of the particular VH or VL. Replacement with an amino acid that is naturally present at that position in a human antibody is preferred. The disclosure thus further provides an antibody A, B, C, D, E, A1, B1, C1, D1, or E1 that comprises a humanized heavy chain variable region, a humanized light chain variable region or a combination thereof.

The disclosure further provides an antibody A, B, C, D, E, A1, B1, C1, D1, or E1 for use in the treatment of a disease in an individual. Also provided is an antibody A, B, C, D, E, A1, B1, C1, D1, or E1 for use in the treatment of a disease that involves too many B cells, overactive B cells, and/or dysfunctional B cells. Further provided is antibody A, B, C, D, E, A1, B1, C1, D1, or E1 for use in the treatment of a CD20 positive neoplasm such as a CD20 positive B-cell lymphoma; hairy cell leukemia; B-cell chronic lymphocytic leukemia, and melanoma.

Also provided is the use of an antibody A, B, C, D, E, A1, B1, C1, D1, or E1 for the manufacture of a medicament for the treatment of a disease that involves too many B cells, overactive B cells, and/or dysfunctional B cells. Also provided is the use of an antibody A, B, C, D, E, A1, B1, C1, D1, or E1 for the manufacture of a medicament for the treatment of a CD20 positive neoplasm such as a CD20 positive B-cell lymphoma; hairy cell leukemia; B-cell chronic lymphocytic leukemia, and melanoma.

Also provided is a method for the treatment of an individual that has a disease that involves too many B cells, overactive B cells, and/or dysfunctional B cells comprising administering to the individual in need thereof an antibody A, B, C, D, E, A1, B1, C1, D1, or E1.

Further provided is a method for the treatment of an individual that has a CD20 positive neoplasm such as a CD20 positive B-cell lymphoma; hairy cell leukemia; B-cell chronic lymphocytic leukemia, or melanoma comprising administering to the individual in need thereof an antibody A, B, C, D, E, A1, B1, C1, D1, or E1.

The disclosure also provides a nucleic acid molecule that codes for a heavy chain, a light chain and/or a variable region thereof. Such a nucleic acid molecule is typically but not exclusively a ribonucleic acid (RNA) or a deoxyribonucleic acid (DNA). Alternative nucleic acids are available for a person skilled in the art, such as, for instance, peptide nucleic acids (PNA). Examples of nucleic acid molecules provided by the disclosure are:

- a nucleic acid molecule that codes for a heavy chain or light chain of an antibody as described herein;
- a nucleic acid molecule that codes for the CDR3 of a heavy or light chains of an antibody as described herein;
- a nucleic acid molecule that codes for the CDR1, CDR2 and CDR3 of a heavy or light chain of an antibody as described herein; and a nucleic acid molecule that codes for the variable region of a heavy chain or of a light chain of an antibody as described herein.

a nucleic acid molecule that codes for a heavy chain variable region comprising a CDR3 region with the sequence SNSYGSTYWYFDV.

a nucleic acid molecule that codes for a heavy chain variable region comprising CDR1, CDR2 and CDR3 region with the sequence SYNLH, (SEQ ID NO:26) AIYPGNGDTSYNQKFKG (SEQ ID NO:27) and SNSYGSTYWYFDV (SEQ ID NO:21), respectively.

a nucleic acid molecule that codes for a heavy chain variable region with the sequence of SEQ ID NO:1, with 0-5 amino acid insertions, deletions, substitutions, additions or a combination thereof at one or more positions other than positions of the amino acids that constitute the CDR1, CDR2 and CDR3 regions, wherein SEQ ID NO:1 has the sequence

QAYLQ QSGAE LVRPG ASVKM SCKAS GYTFT SYNLH WVKQT

PRQGL EWIGA IYPGN GDTSY NQKFK GKATL TVDKS SSTAY

MQLSR LTSED SAVYF CARSN SYGST YWYFD VWGTG TTVTV

SS.

a nucleic acid molecule that codes for a light chain variable region with the sequence of SEQ ID NO:2, with 0-5 amino acid insertions, deletions, substitutions, additions or a combination thereof at one or more positions other than positions of the amino acids that constitute the CDR1, CDR2 and CDR3 regions, wherein SEQ ID NO:2 has the sequence

QIVLS QSPAV LFASP GEKVT MTCRA RSSVS YMDWY QQKPR

SSPKP WIYAT SNLAS GVPAR FSGSG SGTSY SLTIS RVEAE

DAATY YCQQW TSNPP TFGSG TKLEI KRADA APTVS IFPPS

S.

a nucleic acid molecule that codes for a heavy chain that comprises the sequence of SEQ ID NO:1 and the sequence of SEQ ID NO:3, SEQ ID NO:4, or SEQ ID NO:5 with 0-15 amino acid insertions, deletions, substitutions, additions or a combination thereof at one or more positions other than positions of the amino acids that constitute the CDR1, CDR2 and CDR3 regions.

a nucleic acid molecule that codes for a light chain that comprises the sequence of SEQ ID NO:2 and the sequence of SEQ ID NO:6 with 0-15 amino acid insertions, deletions, substitutions, additions or a combination thereof at one or more positions other than positions of the amino acids that constitute the CDR1, CDR2 and CDR3 regions.

a nucleic acid molecule that codes for a heavy chain variable region with a CDR3 region with the sequence YYYGSSYGAMDY (SEQ ID NO:22).

a nucleic acid molecule that codes for a heavy chain variable region that comprises a CDR1, CDR2 and CDR3 region with the sequence SYNMH (SEQ ID NO:28), GIYPGNGDTSYNQKFKG (SEQ ID NO:29) and YYYGSSYGAMDY (SEQ ID NO:22), respectively.

a nucleic acid molecule that codes for a heavy chain variable region comprises the sequence of SEQ ID NO:7, with 0-5 amino acid insertions, deletions, substitutions, additions or a combination thereof at one or more positions other than positions of the amino acids that constitute the CDR1, CDR2 and CDR3 regions, wherein SEQ ID NO:7 has the sequence

QAYLQ QSGAE LVRPG ASVKM SCKAS GYTFT SYNMH WVKQT

PRQGL EWIGG IYPGN GDTSY NQKFK GKATL TVDKS SSTAY

MQLSS LTSED SAVYF CARYY YGSSY GAMDY WGQGT SVTVS

S.

a nucleic acid molecule that codes for a light chain variable region that comprises the sequence of SEQ ID NO:8, with 0-5 amino acid insertions, deletions, substitutions, additions or a combination thereof at one or more positions other than positions of the amino acids that constitute the CDR1, CDR2 and CDR3 regions, wherein SEQ ID NO:8 has the sequence

QIVLS QSPAI LSASP GEKVT MTCRA SSSVS YMHWY QQKPG

SSPKP WIYAT SNLAS GVPAR FSGSG SGTSY SLTIS RVEAA

DAATY YCHQW TFNPP TFGGG TKLEI KRADA APTVS IFPPS

S.

a nucleic acid molecule that codes for a heavy chain that comprises the sequence of SEQ ID NO:7 and the sequence of SEQ ID NO:3, SEQ ID NO:4, or SEQ ID NO:5 with 0-15 amino acid insertions, deletions, substitutions, additions or a combination thereof at one or more positions other than positions of the amino acids that constitute the CDR1, CDR2 and CDR3 regions.

a nucleic acid molecule that codes for a light chain comprising the sequence of SEQ ID NO:8 and the sequence of SEQ ID NO:6 with 0-15 amino acid insertions, deletions, substitutions, additions or a combination thereof at one or more positions other than positions of the amino acids that constitute the CDR1, CDR2 and CDR3 regions.

a nucleic acid molecule that codes for a heavy chain variable region that comprises a CDR3 region with the sequence TYYYGSSPYWSFDV (SEQ ID NO:23).

a nucleic acid molecule that codes for a heavy chain variable region that comprises a CDR1, CDR2 and CDR3 region with the sequence SYNMH (SEQ ID NO:28), AIYPGNGDTSYNQKFKG (SEQ ID NO:27) and TYYYGSSPYWSFDV (SEQ ID NO:23), respectively.

a nucleic acid molecule that codes for a heavy chain variable region comprises the sequence of SEQ ID NO:9, with 0-5 amino acid insertions, deletions, substitutions, additions or a combination thereof at one or more positions other than positions of the amino acids that constitute the CDR1, CDR2 and CDR3 regions, wherein SEQ ID NO:9 has the sequence

QAYLQ QSGAE LVRPG ASVKM SCKAS GYTFA SYNMH WIKQT

PRQGL EWIAA IYPGN GDTSY NQKFK GKATL TVDKS SSTAY

MQLSS LTSED SAVYF CARTY YYGSS PYWSF DVWGT GTTVT

VSS.

a nucleic acid molecule that codes for a light chain variable region that comprises the sequence of SEQ ID NO:10, with 0-5 amino acid insertions, deletions, substitutions, additions or a combination thereof at one or more positions other than positions of the amino acids that constitute the CDR1, CDR2 and CDR3 regions, wherein SEQ ID NO:10 has the sequence

DIQMT QSPAS LSASV GETVT VTCGA SYNIY GALNW YQRKQ

GKSPQ LLIYG ATNLA DGMSS RFSGS GSGRQ YSLKI SSLHP

DDVAT YYCQN VLSNP PTFGG GTKLE IKRAD AAPTV SIFPP

SS.

- a nucleic acid molecule that codes for a heavy chain that comprises the sequence of SEQ ID NO:9 and the sequence of SEQ ID NO:3, 4, or 5 with 0-15 amino acid insertions, deletions, substitutions, additions or a combination thereof at one or more positions other than positions of the amino acids that constitute the CDR1, CDR2 and CDR3 regions.
- a nucleic acid molecule that codes for a light chain comprising the sequence of SEQ ID NO:10 and the sequence of SEQ ID NO:6 with 0-15 amino acid insertions, deletions, substitutions, additions or a combination thereof at one or more positions other than positions of the amino acids that constitute the CDR1, CDR2 and CDR3 regions.
- a nucleic acid molecule that codes for heavy chain variable region that comprises a CDR3 region with the sequence SRLFDSSYGWYFDV (SEQ ID NO:24).
- a nucleic acid molecule that codes for a heavy chain variable region that comprises a CDR1, CDR2 and CDR3 region with the sequence SYNMH (SEQ ID NO:28), AIYPGNGDTSYNQKFKG (SEQ ID NO:27) and SRLFDSSYGWYFDV (SEQ ID NO:24), respectively.
- a nucleic acid molecule that codes for a heavy chain variable region that comprises the sequence of SEQ ID NO:11, with 0-5 amino acid insertions, deletions, substitutions, additions or a combination thereof at one or more positions other than positions of the amino acids that constitute the CDR1, CDR2 and CDR3 regions, wherein SEQ ID NO:11 has the sequence

QAYLQ QSGAE LVRPG ASVKM SCKAS GYTFP SYNMH WVKQT

PRQGL EWIGA IYPGN GDTSY NQKFK GKASQ TVDKS SSTVY

MQLSS LTSAD SAVYF CARSR LFDSS YGWYF DVWGT GTTVT

VSS.

- a nucleic acid molecule that codes for a light chain variable region that comprises the sequence of SEQ ID NO:12, with 0-5 amino acid insertions, deletions, substitutions, additions or a combination thereof at one or more positions other than positions of the amino acids that constitute the CDR1, CDR2 and CDR3 regions, wherein SEQ ID NO:12 has the sequence

QIVLS QSPAI LSAYP GEKVT MTCRA RSSVS YIDWY QQKAG

SSPKP WIYAT SNLAS GVPAR FSGSG SGTSY SLTIS RVEAE

DAATY YCQQW TSNPP TFGGG TKLEI KRADA APTVS IFPPS

S.

- a nucleic acid molecule that codes for a heavy chain that comprises the sequence of SEQ ID NO:11 and the sequence of SEQ ID NO:3, 4, or 5 with 0-15 amino acid insertions, deletions, substitutions, additions or a combination thereof at one or more positions other than positions of the amino acids that constitute the CDR1, CDR2 and CDR3 regions.
- a nucleic acid molecule that codes for a light chain with the sequence of SEQ ID NO:12 and the sequence of SEQ ID NO:6 with 0-15 amino acid insertions, deletions, substitutions, additions or a combination thereof at one or more positions other than positions of the amino acids that constitute the CDR1, CDR2 and CDR3 regions.
- a nucleic acid molecule that codes for a heavy chain variable region that comprises a CDR3 region with the sequence SAYYGSNVWFFDV (SEQ ID NO:25).
- a nucleic acid molecule that codes for a heavy chain variable region that comprises a CDR1, CDR2 and CDR3 region with the sequence SYNLH (SEQ ID NO:26), AIYPGNGDTSYNQKFKG (SEQ ID NO:27) and SAYYGSNVWFFDV (SEQ ID NO:25), respectively.
- a nucleic acid molecule that codes for a heavy chain variable region that comprises the sequence of SEQ ID NO:13, with 0-5 amino acid insertions, deletions, substitutions, additions or a combination thereof at one or more positions other than positions of the amino acids that constitute the CDR1, CDR2 and CDR3 regions, wherein SEQ ID NO:13 has the sequence

QAYLQ QSGAD LVRPG ASVKM SCKAS GFTFP SYNLH WVKQT

PRQGL EWIGA IYPGN GDTSY NQKFK GKATL TVDKS SSTAY

MQLSS LTSED SAVYF CARSA YYGSN VWFFD VWGTG TTVTV

SS.

- a nucleic acid molecule that codes for a light chain variable region that comprises the sequence of SEQ ID NO:14, with 0-5 amino acid insertions, deletions, substitutions, additions or a combination thereof at one or more positions other than positions of the amino acids that constitute the CDR1, CDR2 and CDR3 regions, wherein SEQ ID NO:14 has the sequence

QIVLS QSPAI LSASP GEKVT MTCRA SSSVS YMDWY QQKPG

SSPKP WIYAT SNLAS GVPTR FSGSG SGTSY SLTIS RVEAE

DAATY YCQQW ISNPP TFGAG TKLDL KRADA APTVS IFPPS

S.

- a nucleic acid molecule that codes for a heavy chain that comprises the sequence of SEQ ID NO:13 and the sequence of SEQ ID NO:3, 4, or 5 with 0-15 amino acid insertions, deletions, substitutions, additions or a combination thereof at one or more positions other than positions of the amino acids that constitute the CDR1, CDR2 and CDR3 regions.
- a nucleic acid molecule that codes for a light chain with the sequence of SEQ ID NO:14 and the sequence of SEQ ID NO:6 with 0-15 amino acid insertions, deletions, substitutions, additions or a combination thereof at one or more positions other than positions of the amino acids that constitute the CDR1, CDR2 and CDR3 regions.

A nucleic acid molecule as described herein is preferably used for the production of an antibody A, B, C, D, E, A1, B1, C1, D1 or E1 as described herein by a cell comprising the nucleic acid molecule. A nucleic acid molecule comprising two or more of the indicated sequences comprises such sequence in the order and linkage suitable for the production of an antibody A, B, C, D, E, A1, B1, C1, D1 or E1 as described herein by a cell comprising the nucleic acid molecule. The nucleic acid molecule preferably further comprises one or more sequences for the expression of an antibody as described. Non-limiting examples of such sequences are a promoter, a termination sequence, an enhancer, an intron etc. Such sequences are not necessarily present on the nucleic acid molecule as such sequences can be provided in cis by the integration site of the nucleic acid molecule in, for instance, a chromosome of a cell, or a vector comprising the nucleic acid molecule. Suitable integration sites in a cellular chromosome can easily be determined and targeted, for instance, by means of homologous recombination.

Further provided is a cell that comprises one or more nucleic acid molecules as described herein.

Further provided are means and methods for the production of an antibody as described herein using a nucleic acid molecule of the disclosure or a cell comprising a nucleic acid molecule of the disclosure.

A nucleic acid according to the disclosure, is, for instance, comprised in a cell. When the nucleic acid is expressed in the cell the translation product of the nucleic acid molecule can be incorporated into an antibody of the disclosure. The disclosure thus also provides a cell comprising a nucleic acid molecule according to the disclosure. The disclosure further provides a cell comprising a nucleic acid molecule of the disclosure and that is capable of producing an antibody of the disclosure. Further provided is a method for producing an antibody of the disclosure comprising culturing a cell comprising expressing one or more nucleic acid molecules that code for an antibody of the disclosure and harvesting the antibody from the culture medium, the cell or a combination thereof. The cell is preferably an animal cell, more preferably a mammalian cell. The cell is preferably a cell that is normally used for the production of an antibody for use in humans. Non-limiting examples of such cells are CHO, NSO and PER.C6 cells. Cells may specifically designed to suit certain purposes, for instance, most cell lines used for the production of antibodies have been adapted for growth in suspension, in high densities and other properties. For the purpose of the disclosure a suitable cell is any cell capable of comprising and preferably of producing an antibody according to the disclosure.

PCD function of an antibody as claimed is preferably measured in a method based on annexin V positivity in flow cytometry (as described, for instance, in Example 3).

ADCC function of an antibody as claimed is preferably measured in a method based on B cell depletion in blood drawn from healthy volunteers measured in flow cytometry by the decrease of CD24 positive cells, negative for myeloid markers, or a classical chromium release assay (as described, for instance, in Example 1).

CDC of an antibody as claimed is preferably measured in a method based on 7AAD positivity in flow cytometry (see, for instance, Example 1).

EXAMPLES

Example 1. Novel CD20 Antibodies and Molecular Determinants that Govern Functional Properties of these Antibodies Materials and Methods
Antibodies CD20 mAbs were generated by cellular immunization and standard fusion of spleen cells to obtain hybridomas. Isotypes were determined by FACS (rat-anti-mIgG2a-biotin (cross-reactive with mIgG2c; BD), goat-anti-mIgG2b-Fcγ-RPE (SouthernBiotech), goat-anti-mIgG3-PerCP (Jackson)). mAbs were purified after growth in serum free medium by affinity chromatography using HiTRap rProteinA FF columns (GE Healthcare). Bound protein was eluted with 0.1 M sodium acetate pH 2.5 (Sigma Aldrich) and directly neutralized with 1 M Tris-HCl pH 8.8. Chimeric IgG1 (IgG1) mAbs were generated by cloning the variable regions (synthesized by Shinegene) into Lonza expression vectors (pEE14.4-kappaLC, pEE14.4-IgG1. The L11V mutation was introduced by site-directed mutagenesis. All IgG1 mAbs were produced by transient transfection of HEK293F cells[22] and purified by ProteinA affinity chromatography. All mAbs were dialyzed to PBS (Sigma-Aldrich) and the concentration was determined using the following formula: OD value at 280 nm/correction factor (mIgG 1.36; chIgG 1.35).

RTX (chIgG1; Pharmacy UMC Utrecht), OFA (human (h)IgG1; Pharmacy UMC Utrecht), mouse (m)IgG2a-CD20-7D8 (m7D8) and mIgG2a-CD20-11B8 (m11B8) (kindly provided by Genmab BV, Utrecht, The Netherlands), B1 (mIgG2a, kindly provided by Mark Cragg, Southhampton, UK) and mIgG2a-RTX (mRTX) (Invivogen) were dialyzed to PBS if needed. Abs were labeled with FITC (Thermo Scientific) or Alexa647 (Molecular Probes) following the manufacturer's instructions.

Cell Lines

SKBR3 cells (ATCC) were retrovirally transduced with human CD20 to generate SKBR3-CD20 cells. A subclone stably expressing CD20 was established by limiting dilution. EL4-CD20 cells were generated as previously described.[23] Daudi, Ramos, Raji (ATCC), and the above mentioned cells were cultured in culture medium containing RPMI-1640+ HEPES+glutamine (Invitrogen) supplemented with 10% fetal calf serum (FCS), 100 U/mL penicillin and 100 μg/mL streptomycin (Life Technologies) at 37° C./5% $CO_2$. FreeStyle~ HEK293F cells (Invitrogen) were cultured in FreeStyle™ 293 expression medium (Invitrogen) at 37° C./8% $CO_2$ on an orbital shaker.

Determination of Consensus Amino Acid Sequence of Variable Regions

From frozen dry cell pellets, RNA was isolated and purified using a RNeasy mini kit (Qiagen). Purified RNA (2 μg) was used as templates for cDNA synthesis with a RevertAid H Minus First Strand cDNA synthesis kit (Fermentas). Next, variable light (VL) and variable heavy (VH) regions were amplified in PCR reactions (see Supplementary Materials and Methods). Gel-purified PCR products were cloned into the pCRII blunt TOPO vector (Life Technologies) and transformed into DH5α E. coli. Plasmid DNA was isolated from several clones using a QIAprep spin miniprep kit (Qiagen). Subsequently, consensus DNA sequences of VL and VH regions from each mIgG-CD20 mAb were determined by DNA sequencing (Macrogen) of several plasmid clones containing insert. Based on the sequence information of several clones of each mAb, the consensus V-region sequences were determined and subsequently the amino acid sequences were deduced.

Homotypic Aggregation and Cell Viability Assay $0.4 \times 10^5$ EL4-CD20 cells together with 1 μg/mL Ab in culture medium were plated out in a 96-well plate, and incubated for 24 hours at 37° C./5% $CO_2$. In the crosslinking conditions the following Abs were added 30 minutes later: 20 μg/mL rabbit-F(ab')$_2$-anti-hIgG (Jackson) or 50 μg/mL rabbit-F(ab')$_2$-anti-mIgG (Jackson). Homotypic aggregation was assessed semi-quantitatively using an EVOS microscope (20× magnification). Cell viability was determined by AnnexinV-PE and 7-AAD (Pharmingen) staining, following the manufacturer's instructions.

Human PBMC ADCC

ADCC assays with $^{51}$Cr-labeled target cells were performed as previously described.[22, 24] Briefly, PBMC isolated from healthy individuals (MiniDonorDienst UMC Utrecht) by Ficoll separation (GE Healthcare) were combined with $^{51}$Cr-labeled Daudi cells (effector-to-target ratio=100:1) and CD20 mAb in dilution. After 4 hours incubation at 37° C./5% $CO_2$, the supernatant was harvested and counted in a liquid scintillation counter (MicroBeta; Perkin Elmer). Lysis was calculated using the following formula: % lysis= ((counts of sample−minimum release)/(maximum release−minimum release))×100. Daudi cells with PBMC in culture medium or in medium supplemented with 2.5% Triton X-100 (Roche Diagnostics) were used to determine minimum and maximum release, respectively.

CDC Assay $10^5$ cells (Daudi, Ramos, Raji) were plated out in a 96-well plate and pre-incubated for 30 minutes at room temperature with Ab diluted in culture medium. Human serum (pooled from 8 healthy donors) as complement source (final concentration 15.5%) was added and the preparation kept for 15 minutes at 37° C./5% $CO_2$. The degree of complement-mediated lysis was assessed by staining with 7-AAD (Pharming). Cells were measured on a FACS Canto II (BD).

CD20 Peptide Library Design and Screen

The design of the CD20 peptide library was described elsewhere.[20] Briefly, both linear and cyclic peptides, with loops of different sizes, covering the 2 extracellular loops were directly synthesized onto polypropylene plates.[25, 26] Linear and discontinuous epitopes were reconstructed and for each peptide and a full amino acid scan was included (see Supplementary Materials and Methods).

Recognition of peptides by the CD20 mAb was assessed in a PepScan-based ELISA as previously described.[20] Briefly, 1 μg/mL mAb was added to plates with covalently linked peptides and incubated overnight at 4° C. After extensive washing, bound mAb was detected with a HRP-linked rabbit-anti-mIgG (DakoCytomation) for 1 hour at 25° C. Unbound detection Ab was washed away. Plates were developed using ABTS substrate and color development quantified using a CCD camera and an image-processing system.

Mutant Screen

HEK293F cells were transfected with vectors coding for wild-type or mutated CD20 using 293fectin (Invitrogen) following the manufacturer's instructions. One day post-transfection, cells were harvested, washed in FACS buffer and stained for 30 minutes with 5 μg/mL CD20 mAbs on ice. mAb binding was detected with a goat-anti-hIgG-APC or goat-anti-mIgG-APC Ab (Jackson). Cells were measured on a FACS Canto II (BD).

Ligand Tracer

Kinetics analysis of interactions between the mAbs and CD20 was performed by using the LigandTracer green Technology (Ridgeview Instruments AB). $10^6$ SKBR3-CD20 cells were seeded on one side of a 10 cm culture dish (Greiner) as target cell area and association of 10 nM FITC-labeled CD20 mAb was measured. For non-competitive or competitive dissociation, labeled mAb solution was replaced by RPMI culture medium or 100 nM unlabeled mAb of the same clone, respectively. Analysis was performed using an OneToOne fitting model in TraceDrawer (Ridgeview Instruments AB).

EL4-CD20 Lymphoma Model

C57BL/6 mice were purchased from Janvier (France) or bred in the facilities. 4-6 mice/group were injected intraperitoneally (i.p.) with $5\times10^5$ CellTraceViolet (10 μM, Invitrogen)-labeled EL4-CD20 cells. After 16 hours, mice were treated with mAb or PBS (100 μL) injected i.p. A peritoneal lavage with PBS containing 5 mM EDTA was performed after 24 hours and the amount of remaining tumor cells was determined using TruCount tubes (BD). All experiments were approved by the Animal Ethical Committee of the UMC Utrecht.

Supplementary Materials and Methods

Amplification of VH and VL Regions

The PCR reaction contained 25 ng cDNA, 1× AccuPrime mix (Life Technologies), 25 pmol 5' and 3' primers (Biolegio) annealing to the cDNA encoding the signal peptide and to the constant region of the antibody, respectively, and AccuPrime™ Pfx DNA Polymerase (Life Technologies) according to manufacturer's instructions. Amplification consisted of initialization at 95° C. for 2 minutes, followed by 34 cycles of denaturation at 95° C. for 30 seconds, annealing at 55 or 60° C. for 30 seconds, and extension at 68° C. for 2.5 minutes, finally the 34 cycles were followed by an extension step at 68° C. for 7 minutes. PCR tubes were maintained at 4° C. until further processing.

Binding Assay $10^5$ Daudi cells were plated out in a 96-well plate and incubated with mIgG CD20 mAbs (in PBS) for 45 minutes on ice. After washing, bound CD20 mAbs were detected with goat-F(ab')2-anti-mIgG(H+L)-APC (Southern Biotech) and subsequently measured on a FACS Canto II (BD).

Detailed Description of Peptide Library Used in Epitope Mapping Experiment

Single-domain and double-domain peptides covering the 2 extracellular CD20 loops were used to reconstruct linear and discontinuous epitopes. For each peptide a full positional aa scan (i.e., each position is replaced by all other aa) was included. The second part of the library consisted of cyclic peptides by introducing cysteine-based loops using the Pepscan technology (www.pepscan.nl). The following peptides were included: (a) all overlapping linear 34-mers covering the large loop, including a full alanine-scan of each 34-mer peptide; (b) 34 overlapping peptides from the large loop and 1 peptide from the small loop were combined in a matrix of 35×35 with each other in order to map discontinuous epitopes that are spread over two different parts; (c) all overlapping linear 15-mers covering complete CD20; (d) a full positional aa scan (excluding cysteine) of YNCEPANPSEKNSPSTQYCYS (SEQ ID NO:16); (e) one double-looped small loop covering peptide; (f) single-looped peptides of varying size covering the large loop to capture conformational epitopes that depend on a particular loop size and (g) all overlapping single-looped 15-mers covering the complete extracellular sequence of the CD20 molecule.

FACS-Based Dissociation $10^5$ Daudi cells were incubated with 10 μg/mL Alexa647-labeled mAb for 1 hour at 37° C. and then pelleted and resuspended in either 100 μg/mL unlabeled mAb or complete RPMI culture medium. Cells were left at 37° C./5% $CO_2$ and measured on a FACS Canto II at indicated time points to determine the level of cell-bound mAbs over time. The remaining mean fluorescence intensity (MFI) at each time point was expressed as a percentage of the initial MFI.

Results

New CD20 mAbs Exhibit Type I Characteristics

A panel of novel CD20 mAbs was generated and characterized in detail. After fusion of spleen B-cells of 6 immunized mice, 17 stable hybridoma clones producing mIgG2c-, mIgG2b- and mIgG3-CD20 mAbs (Table 1) were obtained. For 14 out of 17 CD20 mAbs, unique VH and VL chain sequence pairs with differing degrees of relatedness (FIGS. 1.1 and 1.2) were retrieved. Comparison of the new mIgG-CD20 mAbs with available Type I/II CD20 mAbs revealed that the CDR3 of the VH chain is the least conserved (27-63% identity for new mIgG-CD20 mAbs compared to RTX). For further studies, 11 CD20 mAbs were purified. Their binding was comparable to Type I CD20 mAbs m7D8 (derived from same panel as OFA with comparable properties[14] but expressed as mIgG2a mAb) and mRTX (FIG. 19).

Next, their MoA was determined. Neither PCD (FIG. 2A) nor homotypic aggregation (FIG. 20), both strongly elicited by Type II mAbs, were induced by the new CD20 mAbs in the absence of a cross-linking Ab.

Figure 2B:
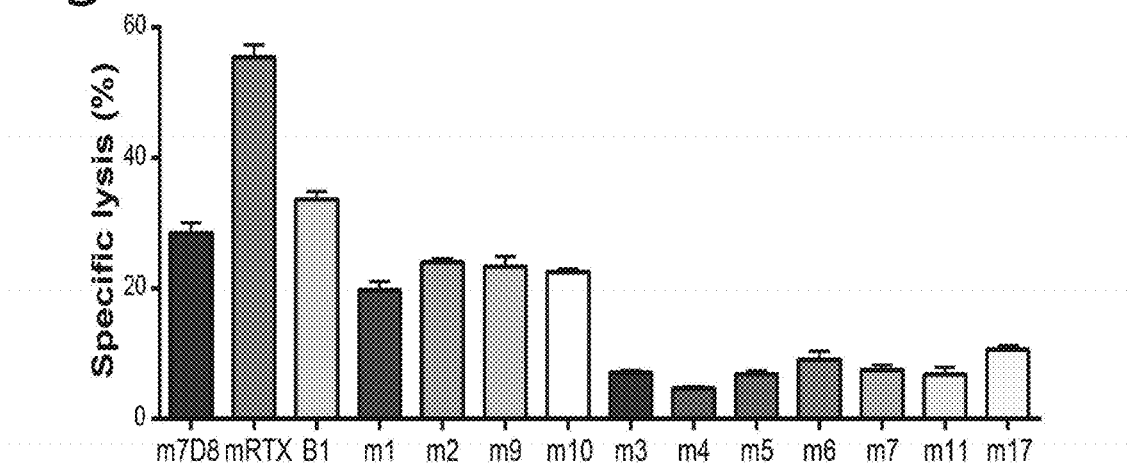
Figure 2C:
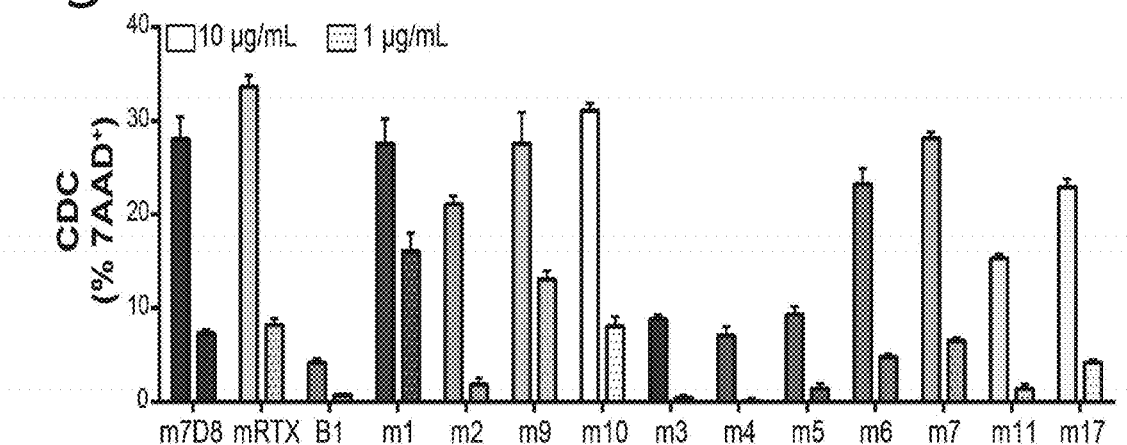

As a shared feature of Type mAbs, specific cell lysis in an ADCC assay using Daudi cells as targets and PMBC as effectors (FIG. 2B) was determined. A comparable degree of lysis was obtained with all mIgG2c-CD20 mAbs. In contrast, mIgG2b mAbs were less effective. Remarkably, CDC activity, the MoA only elicited by Type I mAbs, differed considerably amongst the CD20 mAbs (FIG. 2C).

Variation of CDC Capacity of New mIgG2c-CD20 mAbs

Figure 3B:
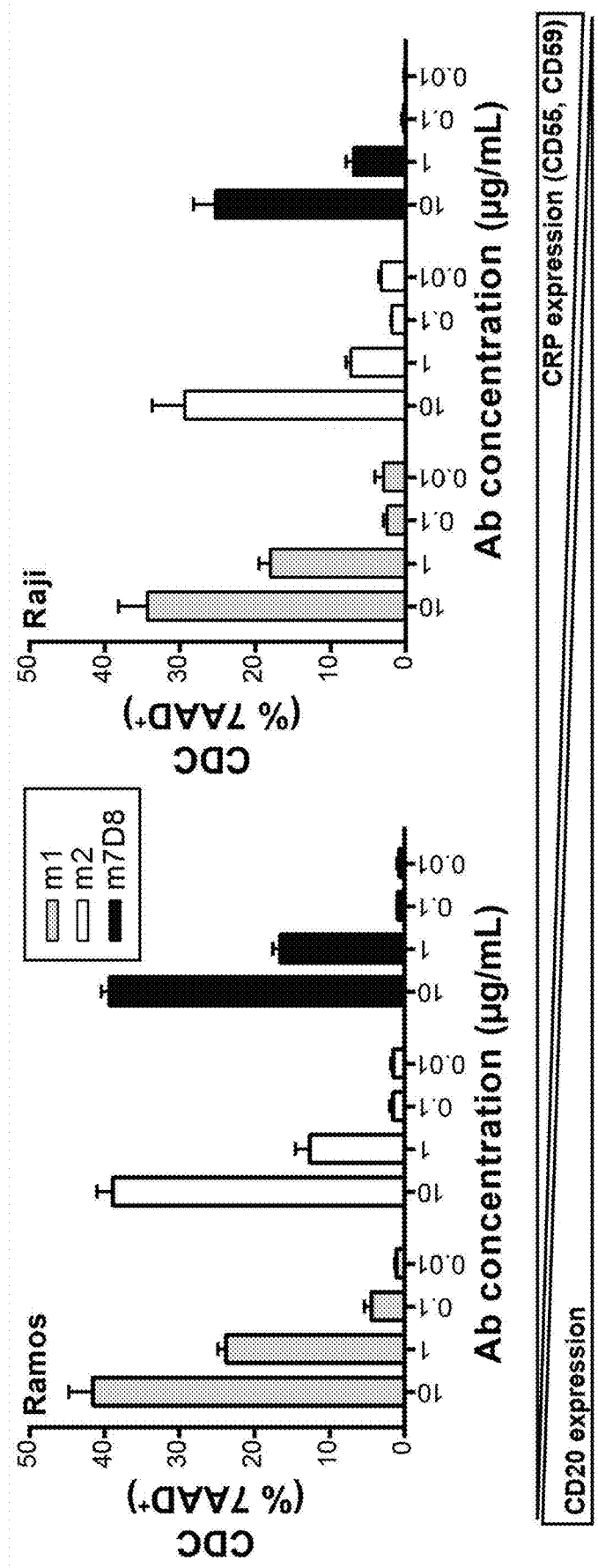

For further comparisons, focus was placed on the mIgG2c mAbs as they exhibited higher levels of effector functions. CDC was analyzed over a wider concentration range on Daudi cells, a cell line sensitive for complement-mediated lysis due to high CD20 and low complement-regulatory protein (CRP) expression (FIG. 3A). m1 and m9 showed the highest CDC activity, in particular, between 0.1-3 µg/mL mAb. m10 displayed intermediate CDC potency, and m2 was the least potent. The better CDC induction by m1 compared to m2 was also detected in assays with Ramos and Raji cells, which have decreasing CD20 and increasing CRP expression (FIG. 3B).

New CD20 mAbs with Overlapping, but Distinct Epitopes

To study a possible correlation between functional properties and the epitope, m1 and m2, both mIgG2c-CD20 mAbs but highest/lowest in CDC, were subjected to a detailed epitope mapping analysis applying the PepScan-technology. Critical residues of m1 were identified to be $^{168}$EPANPSEK$^{175}$ by using linear (FIG. 21A) and circular (FIG. 4A, left) peptides with a positional amino acid scan covering the larger extracellular loop. In contrast, the signal for binding of m2 to the linear (FIG. 21B) and circular (FIG. 4A, right) peptide was rather low. However, a signal decrease below the wild-type (WT) binding signal only occurred within the $^{168}$EPANPSEK$^{175}$ sequence motif. This suggests that the epitope of both mAbs is located on the larger loop in the same region, however their binding characteristics are different. The data suggest that m1 binds to a linear epitope, whereas m2 might bind to a conformational epitope.

Figure 4B:
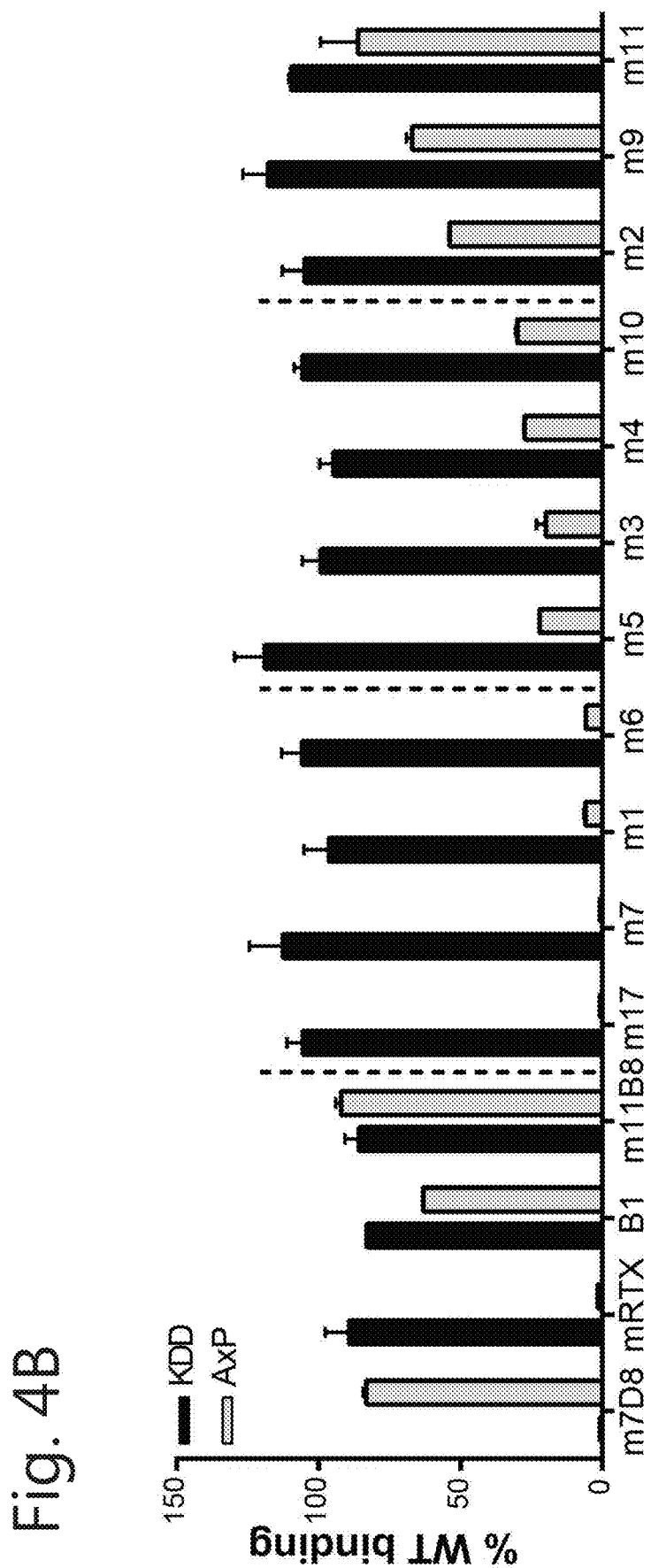

After identifying the epitope of two new CD20 mAbs based on peptide scanning, defining the recognition sites on properly folded CD20 for the complete mAb panel was of interest next. Therefore, a rough epitope mapping experiment with two CD20 mutants was first performed, with amino acids mutated in either the small (T159K/N163D/N166D) or larger (A170S/P172S) loop of CD20 (FIG. 4B). None of the new CD20 mAbs showed an impaired binding upon mutations in the binding region of m7D8 (T159K/N163D/N166D). Mutations in the RTX epitope region (A170S/P172S) resulted in diminished binding of all new CD20 mAbs to a different extent (0-20% of WT binding: RTX, m1, m6, m7, m17; 20-30% of WT binding: m3, m4, m5, m10; 50-80% of WT binding: m2, m9, m11).

To determine crucial amino acids required for binding within the larger extracellular loop, a single mutant library spanning the $^{168}$PANPSEKNSP$^{178}$ sequence (FIG. 4C) was used. All 11 evaluated CD20 mAbs with unique sequence pairs showed distinct binding patterns. None of the 11 new CD20 mAbs showed loss of binding upon mutations of N176 or E174, two residues found to impact binding of the Type II mAbs B1 and m11B8, respectively. The binding of m9 remained untouched by any mutant. All other new CD20 mAbs showed an impaired binding to the CD20 molecule upon mutation of N171, as seen for mRTX. The two single mutants A170P and P172A made it possible to identify the contributing amino acids within the A170S/P172S double-mutant. The A170P mutation did not affect mAb binding. In contrast, the P172A mutant influenced binding of all new CD20 mAbs, except for m2, m9 and m11. Residue 5173 was identified to be important for the binding of mRTX, m1, m4 and m10. Overall, the epitope of most new CD20 mAbs can be narrowed down to $^{170}$ANPSE$^{174}$, however different amino acids are required for binding.

CD20 mAbs Show Variation in Binding Stability

Figure 5A:
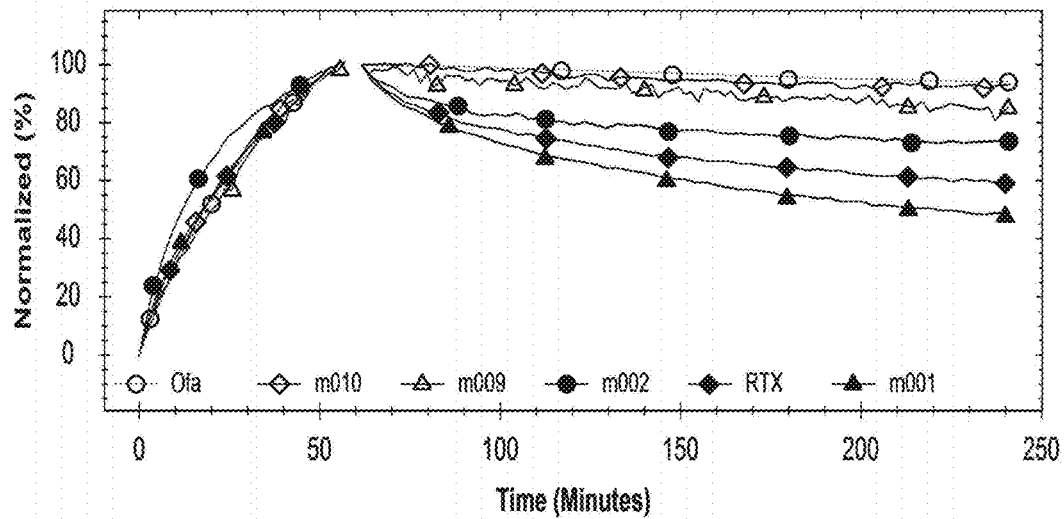
FIGS. 5A-5C. New CD20 mAbs with distinct kinetics. Real-time binding and dissociation curve to SKBR3-CD20 cells using Ligand Tracer Green. Association of 10 nM FITC-labeled CD20 mAbs was monitored for 1 hour before following the dissociation for 3 hours in the presence of (FIG. 5A) RPMI culture medium (non-competitive) or (FIG. 5B) 100 nM unlabeled CD20 mAbs (competitive).
Figure 5B:
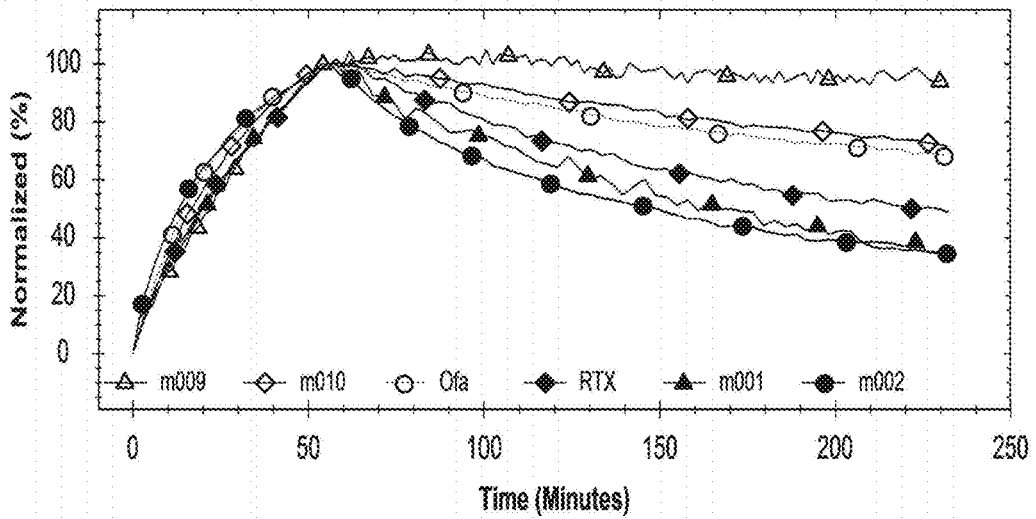
Figure 5C:
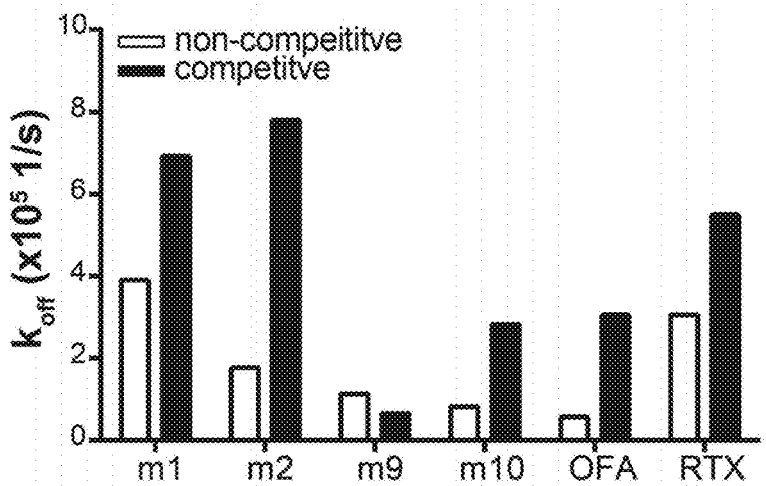
Figure 22A:
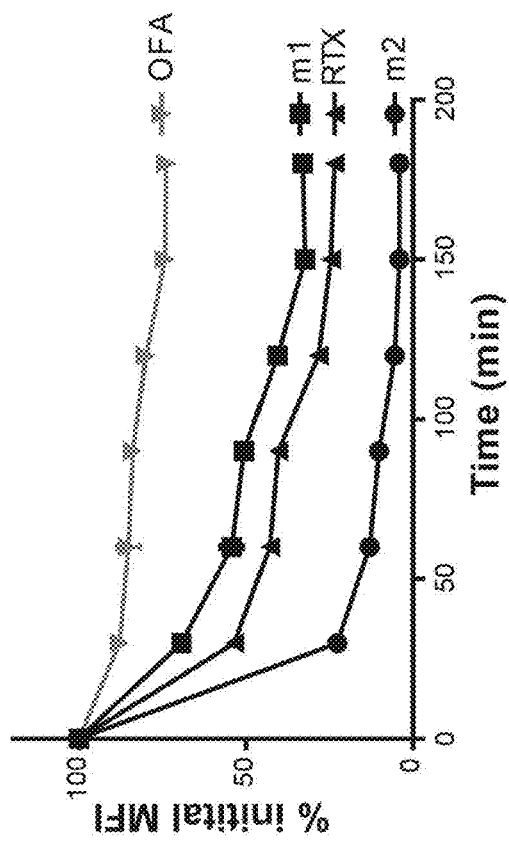
Figure 22B:
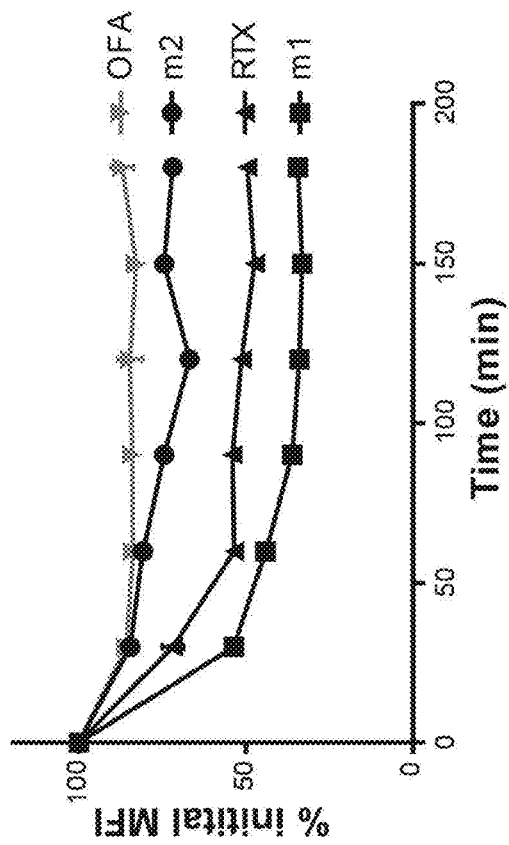
Figure 22C:
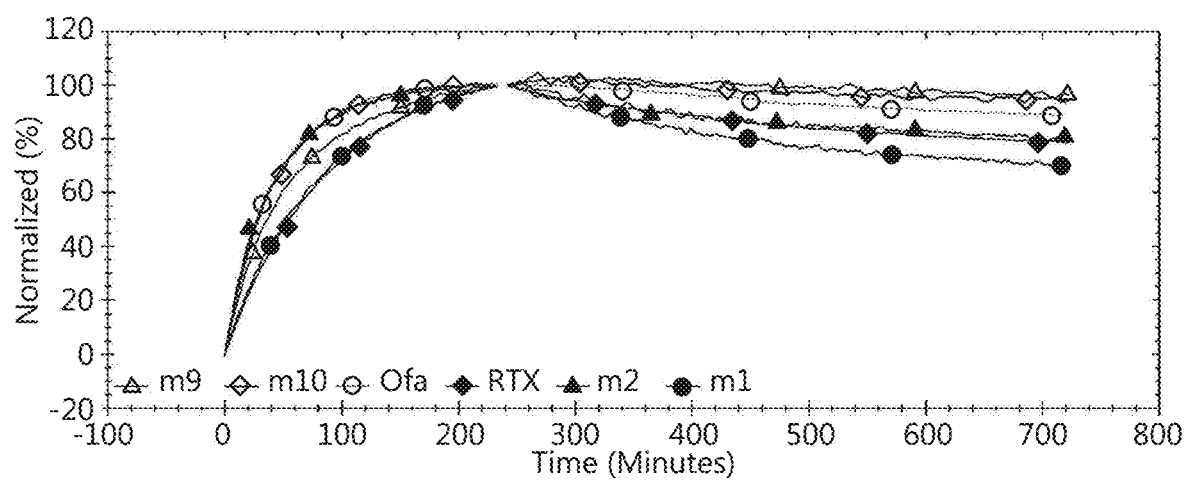
Figure 22D:
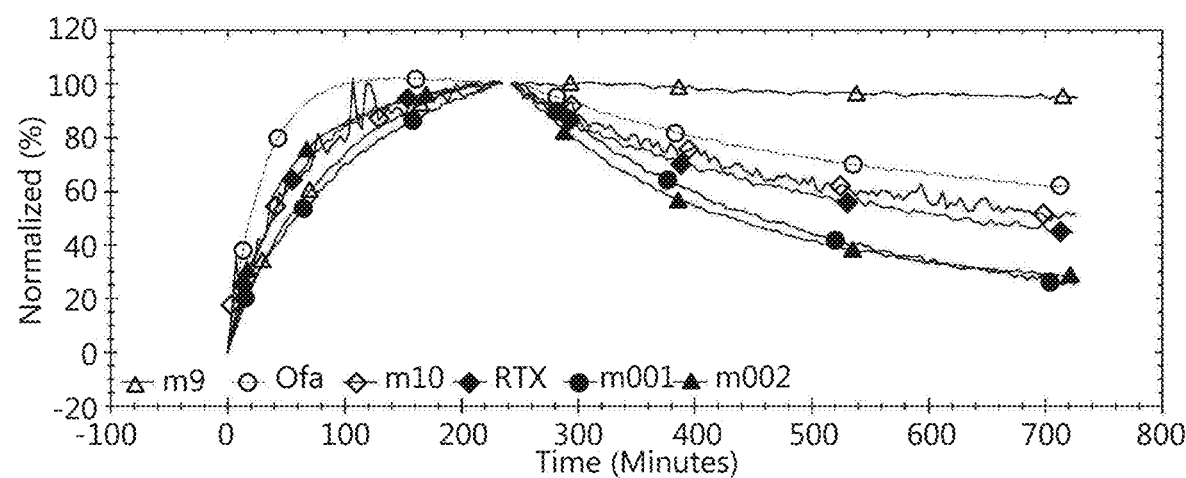

A slow Ab off-rate might favor the formation of Ab-C1q complexes, the first component of the classical complement pathway. FACS-based dissociation assays hinted at unique dissociation behaviors of m1 and m2 (FIGS. 22A, 22B), suggesting a faster off/on-rate for m2. To characterize interaction kinetics and affinity of mAbs, the LigandTracer technology was used to record real-time binding and dissociation of Abs to cellular receptors. Kinetics analysis was performed for all 4 mIgG2c-CD20 mAbs under non-competitive (FIG. 5A, left) and competitive (FIG. 5A, right) conditions and detected differences in their binding behavior. All mAbs had a similar apparent affinity in the low to sub-nanomolar range (Table 3). Binding rate constants were comparable for all mAbs. The major difference in kinetics was observed in the dissociation phase. OFA, m9 and m10 dissociated very slowly, while m1, m2 and RTX had a more pronounced biphasic release pattern, meaning that one fraction of the mAbs is dissociating rapidly while another fraction is more stable bound (determined by Interaction-Map analysis; data not shown). Also, except for m9, dissociation under competitive conditions is faster than under non-competitive conditions (FIG. 5C), indicating that dissociated mAbs rebind to the cell under non-competitive conditions. This occurs, for example, when other receptors are in close proximity or when Ab binding is stabilized by multiple binding, such as in Ab-(CD20)$_2$ or CD20-Ab-C1q complexes. m2 has the largest fraction of fast releasing Abs and dissociation is strongest affected by competition. The formation of more stable complexes due to multiple interactions is substantiated by the observation that competition has a stronger impact on the release of labeled mAb when incubation times are prolonged (FIG. 22C, 22D).

Chimerization can Impact Functional Properties

Figure 6:
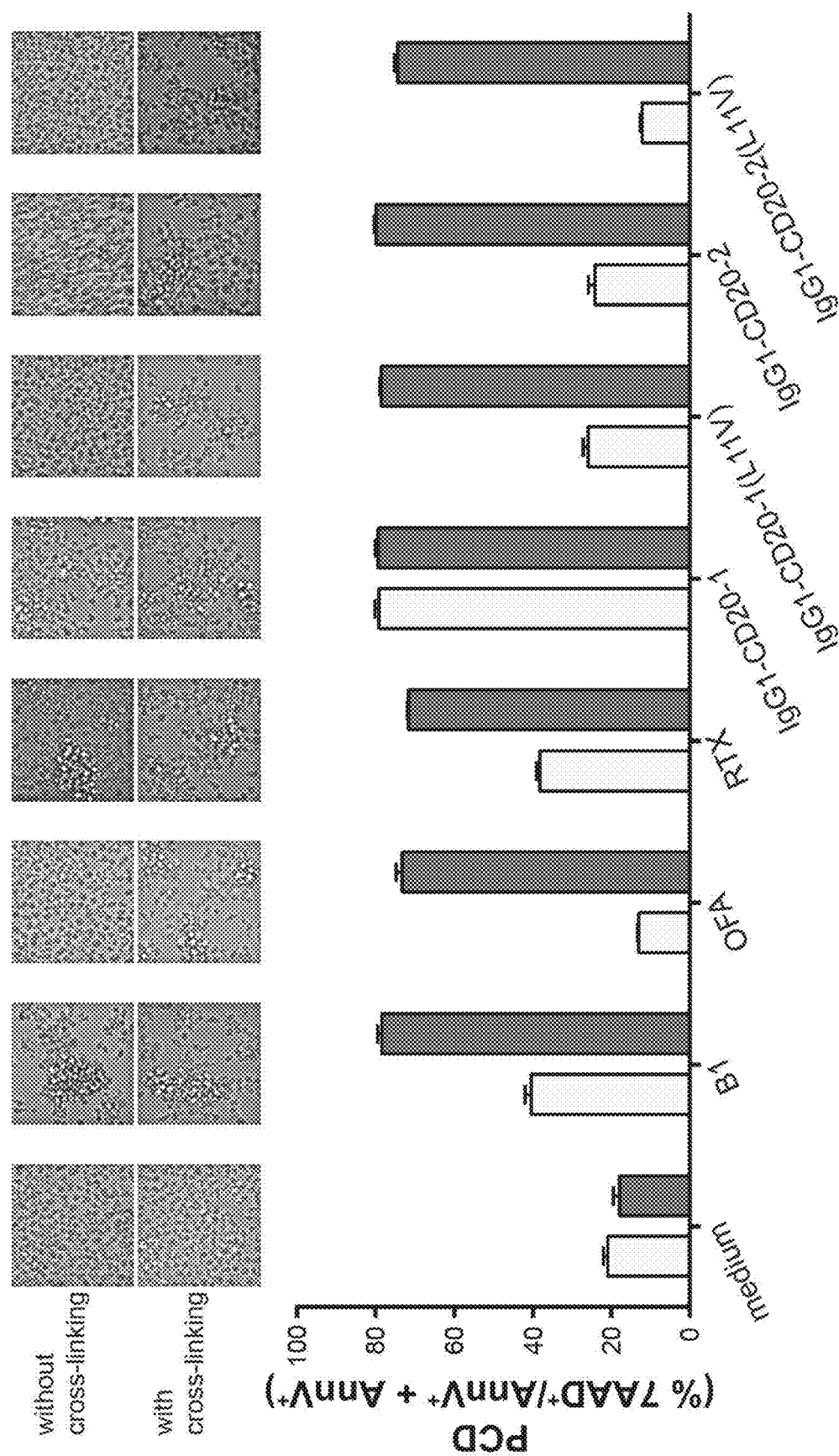
FIG. 6. Chimerization can alter PCD activity. Induction of homotypic aggregation (pictures) and PCD by IgG1-CD20-1 and IgG1-CD20-2 mAbs (1 µg/mL) with or without the L11V mutation in the absence (light grey bar) or presence (dark grey bar) of cross-linking Ab (for IgG1, a-human IgG: 20 µg/mL; for B1, a-mouse IgG: 50 µg/mL). B1 and OFA as positive and negative control, respectively. Induction of cell death was determined by 7-AAD and AnnexinV-PE staining (mean+SEM).

During the humanization of B-Ly1 to OBZ, a leucine to valine mutation at Kabat position 11 in the VH chain was introduced. The insertion of a V11L mutation into the OBZ sequence resulted in the loss of its PCD capacity and widened its elbow angle. To evaluate whether this residue generally alters the MoA of CD20 mAbs, the reverse mutation (L11V) was introduced into the chimerized versions of m1 (IgG1-CD20-1) and m2 (IgG1-CD20-2), respectively. Binding, ADCC and CDC were comparable at a saturating concentration (data not shown). Surprisingly, in a PCD assay with EL4-CD20 cells (FIG. 6) IgG1-CD20-1 induced PCD, a property lost upon insertion of the V11L mutation. In contrast, for IgG1-CD20-2 neither the parental nor the mutated versions induced PCD. This indicates that the MoA can change upon chimerization and that the elbow angle determining region plays a crucial role in it.

New CD20 mAbs Exhibit Variation in Anti-Tumor Response In Vivo

Figure 7A:
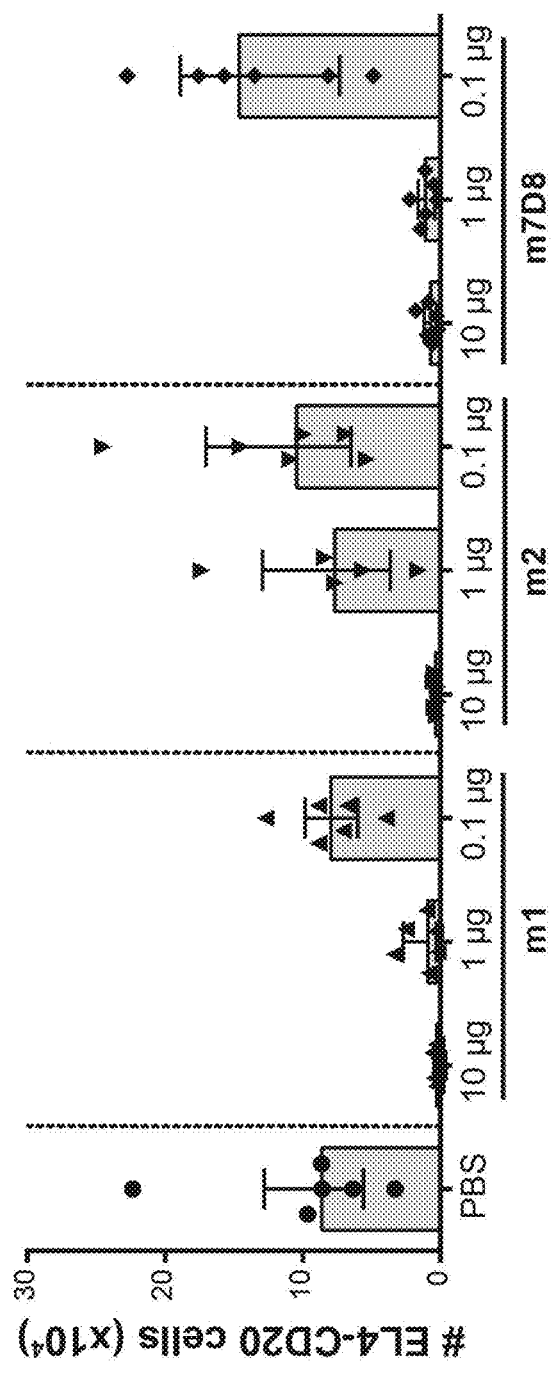
FIGS. 7A, 7B. Differences in in vivo efficacy of mIgG2c-CD20 mAbs. C57BL/6 mice (4-6 mice/group) were injected intraperitoneally with 5×105 CellTraceViolet labeled EL4-
Figure 7B:
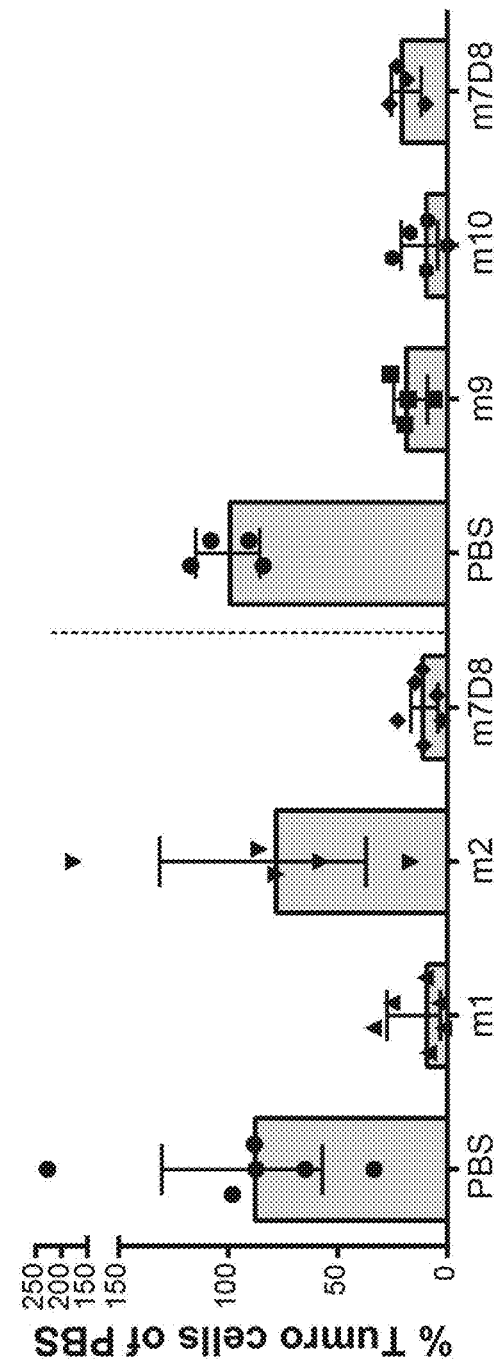

As mIgG2c-CD20 mAbs were the most potent in vitro, their in vivo potency in a short low tumor burden model was studied, previously established in the lab.[27] In this model CDC was shown to be the dominant effector mechanism for tumor cell eradication. Since m1 and m2 displayed the biggest differences in vitro, these two mAbs were used first to determine the effective Ab concentration (FIG. 7A). A clear concentration-dependent anti-tumor response was observed, and at 1 μg mAb a complete clearance of the tumor cells was achieved with m1 but not m2. Testing the efficacy of the remaining mIgG2c mAbs at 1 m9 and m10 show that they performed comparable to m1 (FIG. 7B).

Discussion

For the treatment of B-cell malignancies, RTX (chIgG1), OFA (hIgG1) and OBZ (glycoengineered hIgG1 Fc-region for enhanced ADCC) targeting CD20 are FDA approved. In vitro they induce tumor cell killing mediated by either ADCC and CDC (Type I; RTX and OFA) or ADCC and PCD (Type II; OBZ). It is likely that certain patient groups with e.g., less beneficial FcγR polymorphisms or different types of B-cell malignancies might benefit from treatments with highly complement active or apoptosis inducing mAbs. In order to develop more effective CD20 therapeutic mAbs, further understanding of the underlying characteristics dictating the MoA of CD20 mAbs is important. Generating Type-specific CD20 mAbs remains a challenge, not only due to the low innate immunogenicity of the CD20 molecule itself, but also due to the lack of understanding, which Ab properties are relevant for function. New CD20 mAbs were raised using an efficient in-house developed immunization method and purified 11 mAbs for further characterization. Studying functional properties revealed all new CD20 mAbs to exhibit Type I characteristics as they induce CDC, but not PCD. In the panel, mIgG2b was the most frequent isotype, followed by mIgG2c and mIgG3. This is indicative for more matured Abs, since mIgG2c and mIgG2b Abs are further advanced in the class switching order of the heavy chain in C57BL/6 mice (5' cμ-cδ-cγ3-cγ1-cγ2b-cγ2c-cε-cα3').[28] The diversity in the variable regions indicated that affinity-matured CD20 mAbs were raised.

To investigate underlying properties for the MoA of the new mAbs, the epitope was determined, binding kinetics and structural properties based on a mutation at Kabat position 11. For the epitope, the C-terminal part of the larger loop of CD20 was found to be relevant for B1 and OBZ binding, suggesting that this epitope is important for the Abs' Type II features.[18, 29] However, the similar location of the epitope of OBZ and B1 is most likely an incomplete explanation as B-Ly1, the parental Ab of OBZ,[30] does not display the complete Type II characteristics before humanization.[31] Additionally, the epitope of Type II mAb 11B8 is not overlapping, but comprised of amino acids located on the small and large extracellular loop, similar to 7D8 and OFA. 10 out of 11 of the mAbs bound in the same region as RTX. The data suggest that residue S173 is relevant in determining the type of epitope. Binding of m1 (linear epitope) is abrogated upon mutation of residue S173. In contrast, m2 binding (conformational epitope), is much less affected. This varying recognition results in an alteration of the binding behavior and in depth analysis suggests that it has an impact on the capacity of the mAb to create secondary interactions. Also the recently suggested V11L mutation in GA101, reversing the mAbs Type II characteristics, is not a universal explanation. Sequence comparison confirmed that Type I CD20 mAbs, but also B1 and 11B8, all carry a leucine at this position. Interestingly, the chimerized mAbs derived from m1 exhibited PCD capacity. Subsequent introduction of valine at Kabat position 11 abrogated all PCD activity. This points at an involvement of the elbow-hinge angle, however it is inconclusive as to which residues are important, as the amino acid sequences of the VH framework of m1 and m2 are identical. Kabat position 11 with B1 might be involved, as next to the elbow-hinge angle, the lack of binding to N171 was implicated as a second requirement.[12]

Concerning the binding kinetics, previous findings on the contribution of the off-rate of CD20 mAbs to CDC were contradictory. Mitigating the off-rate of RTX with a non-complement activating reagent increased its CDC activity.[14] Also veltuzumab, a humanized IgG1 mAb with CDRs identical to RTX except for 1 residue, displays a slower off-rate than RTX and higher CDC capacity.[32] However, no CDC enhancement was induced by RTX mutants with a slower off-rate.[33] With the panel of mIgG2c-CD20 mAbs, which varied in their ability to elicit CDC, no correlation was found between good CDC and slow dissociation as determined in LigandTracer experiments. Generally, functional characteristics could not be clearly correlated to the observed differences in the interaction kinetics or affinity and/or the epitope. Recently, it was suggested that the superior CDC activity of hIgG1 mAbs is due to Fc-Fc interactions after antigen-binding, resulting in the formation of hexamers, which eventually facilitate C1q-binding.[34] Introduction of mutations strengthening the Fc-interactions in weak complement-activating Abs resulted in enhanced CDC activity.[35]

The binding kinetics analysis revealed, however, divergent dissociation patterns and suggests that the CD20 mAbs differ in their ability to bind other molecules, leading to stabilization of Ab binding; whereas most OFA and m10 rapidly form a stable interaction, for m1, m2, and RTX a more heterogeneous pattern was observed. The release of m2 was clearly affected by self-competition. These data point to multi-site binding of the mAbs, which differs among the panel. The fraction of mAbs, which releases more quickly reduces upon increasing the incubation time. These findings raise the question of the time dependency and type of complex formation and its effect on lipid raft formation by Type I mAbs, and eventually the influence on CDC induction.

In vitro, the new mIgG2c-CD20 mAbs could be grouped in strong (m1 and m9), intermediate (m10) and weaker (m2) complement inducers. In vivo, m1, m9 and m10 performed comparable, whereas m2 was less effective. This suggests that differences detected in in vitro CDC assays were not noticeable with the used model. This is likely a model dependent effect, and different when other in vivo models are used. Characteristics that govern the functional properties of CD20 mAbs are indicated in FIG. 23.

Example 2

Material and Methods
Antibodies
Rituximab (RTX, chimeric (ch)IgG1), Ofatumumab (OFA, human (h)IgG1), and Trastuzumab (TRA, humanized IgG1) were obtained from the Pharmacy of the UMC Utrecht.

The generation of the new chimeric IgG1 mAbs IgG1-CD20-1 and IgG1-CD20-2 was described in Chapter 7. IgG1-CD20-7, IgG1-CD20-9, and IgG1-CD20-10 were made by U-Protein (Utrecht), who produced the mAbs in HEK293T cells. All mAbs were dialyzed to 1× PBS (Sigma-Aldrich) and the concentration was determined using the following formula:

$$\frac{OD \text{ value at } 280 \text{ nm}}{\text{correction factor } (chIgG\ 1.35)}.$$

Cell Lines

Daudi cells (ATCC) were cultured in RPMI culture medium containing RPMI-1640+HEPES+glutamine (Invitrogen) supplemented with 10% fetal calf serum (FCS) and 100 U/mL penicillin and 100 μg/mL streptomycin (1× P/S; Life Technologies) at 37° C./5% $CO_2$. EL4-CD20 cells were generated as previously describer[23] and cultured in RPMI culture medium.

Binding Assay $10^5$ Daudi cells were plated out in a 96-well plate and incubated with IgG1-CD20 mAbs (in PBS) for 45 minutes on ice. After washing, bound CD20 mAbs were detected with goat-F(ab')$_2$-anti-hIgG-RPE (Southern Biotech) and subsequently measured on a FACS Canto II (BD).

Human PBMC ADCC

ADCC assays with $^{51}$Cr-labeled target cells were performed as previously described.[22] PBMCs were isolated from healthy individuals (MiniDonorDienst UMC Utrecht) by Ficoll separation (GE Healthcare; Sigma-Aldrich). $^{51}$Cr-labeled Daudi cells were combined with PBMCs (effector-to-target ratio=50:1) and CD20 mAb in dilution. After 4 hours incubation at 37° C./5% $CO_2$, the supernatant was harvested and counted in a liquid scintillation counter (MicroBeta; Perkin Elmer). Lysis was calculated using the following formula:

$$\% \text{ lysis} = \frac{counts_{sample} - counts_{minimal\ release}}{counts_{maximum\ release} - counts_{minimal\ release}} \times 100.$$

Daudi cells with effector cells in RPMI culture medium or in medium supplemented with 2.5% Triton X-100 (Roche Diagnostics) were used to determine minimal and maximum release, respectively.

CDC Assay $10^5$ cells Daudi cells were plated out in a 96-well plate and pre-incubated for 30 minutes at room temperature with mAbs diluted in RPMI culture medium. Human serum (pooled from 8 healthy donors) as complement source (final concentration 15.5%) was added and the preparation kept for the 15 minutes at 37° C./5% $CO_2$. The degree of complement-mediated lysis was assessed by staining dead cells with 7-AAD (BD Pharmingen). Cells were measured on a FACS Canto II (BD).

Cell Viability Assay $4\times10^4$ EL4-CD20 cells together with 1 μg/mL Ab in RPMI culture medium were plated out in a 96-well plate, and incubated for 24 hours at 37° C./5% $CO_2$. In the cross-linking condition 20 μg/mL rabbit-F(ab')$_2$-anti-hIgG (Jackson ImmunoResearch) was added 30 minutes after start of incubation. Cell viability was determined by AnnexinV-PE and 7-AAD (BD Pharmingen) staining, following the manufacturer's instructions.

B-Cell Depletion Assay

Blood from healthy donors was collected in Hirudin blood tubes and stored on ice until use. mAbs were diluted in RPMI-1640+HEPES+glutamine (Invitrogen) and unprocessed blood was added. After incubation of the plates for 60 minutes at 37° C./5% $CO_2$ samples were kept on ice for all further steps. Leukocytes and CD19$^+$ cells were stained by adding mouse-anti-hCD45-PO (Life Technologies) and mouse-anti-hCD19-APC (Biolegend) for 30 minutes. Subsequent lysis of erythrocytes with 1× BD Pharm Lyse Lysing buffer (BD) supplemented with 5 mM EDTA pH 8 (Sigma-Aldrich), 7-AAD (BD Pharmingen) and Cyto/Cal Multifluor Plus Violet Flow Cytometer Alignment Beads (Thermo Scientific) was followed by measurement on a FACS Canto II (BD).

EL4-CD20 Lymphoma Model

C57BL/6 mice were purchased from Janvier (Le Genest Saint Isle, France). 6 mice/group were injected intraperitoneally (i.p.) with $5\times10^5$ CellTraceViolet (10 μM, Invitrogen)-labeled EL4-CD20 cells. After 16 hours, mice were treated with 10 μg mAb or PBS (100 μL) injected i.p. A peritoneal lavage with 1×PBS containing 5 mM EDTA was performed after 24 hours. The amount of remaining tumor cells was determined using TruCount tubes (BD). All experiments were approved by the Animal Ethical Committee of the UMC Utrecht.

Results

From the panel of previously characterized mIgG CD20 mAbs, 5 promising candidates for chimerization were selected. Four of these were mIgG2c mAbs (m1, m2, m9, and m10; see Example 1) which exhibited a diverse functional pattern in vitro. Among the mIgG2b mAbs, m7 displayed the highest complement-dependent cytotoxicity. After cloning the variable regions into human IgG1 constant region and human kappa light chain (LC) expression vectors, the mAbs in either HEK293F or HEK293T cells were produced. Subsequently, purified chIgG1 mAbs were subjected to a preliminary in vitro characterization.

Figure 8:
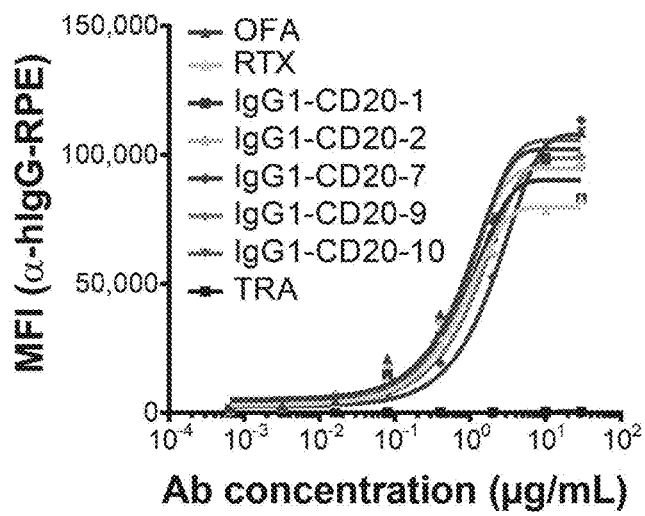
FIG. 8. New chimeric IgG1-CD20 mAbs bind to CD20-expressing Daudi cells. Binding was determined by FACS after incubation of Daudi cells with a dilution series of mAb. RTX and OFA were included as positive controls, and Trastuzumab as isotype control.

First, the antigen-binding capacity of all chimerized CD20 mAbs were tested. They specifically bound to CD20 positive Daudi cells (FIG. 8). Their binding pattern was comparable to the commercially available CD20 mAbs RTX (chIgG1) and OFA (hIgG1).

Figure 9A:
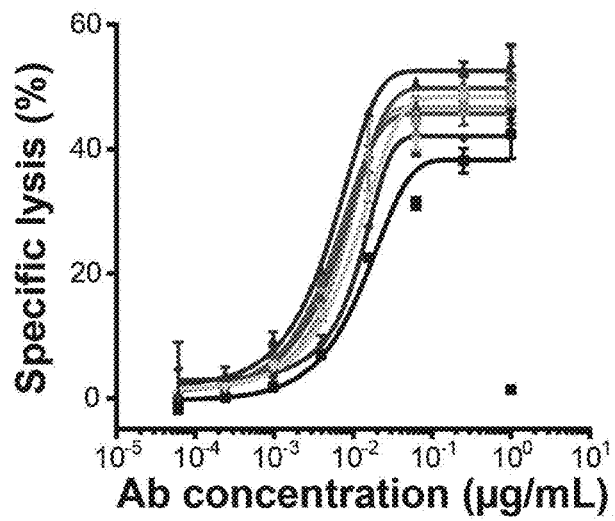
FIGS. 9A-9G. Analysis of in vitro efficacy of new chimeric IgG1-CD20 mAbs.

Next, their potential to eradicate tumor cells in two different assays was assessed. First, tumor cell killing was measured in a classical chromium-release ADCC assay, by incubating $^{51}$Cr-labeled Daudi cells with mAb and PBMCs (effector to target ratio=50:1) (FIG. 9A). With the chimeric IgG1-CD20 mAbs clearer differences in their ADCC capacity could be seen, compared to their mouse versions (Example 1). The percentage of maximal lysis at 1 μg/mL mAb ranged between 38% (IgG1-CD20-1) and 49% (IgG1-CD20-10). Though maximal lysis was slightly higher for the commercial mAbs RTX and OFA, at lower concentrations, IgG1-CD20-2, IgG1-CD20-9, and IgG1-CD20-10 performed better than RTX.

Figure 9B:
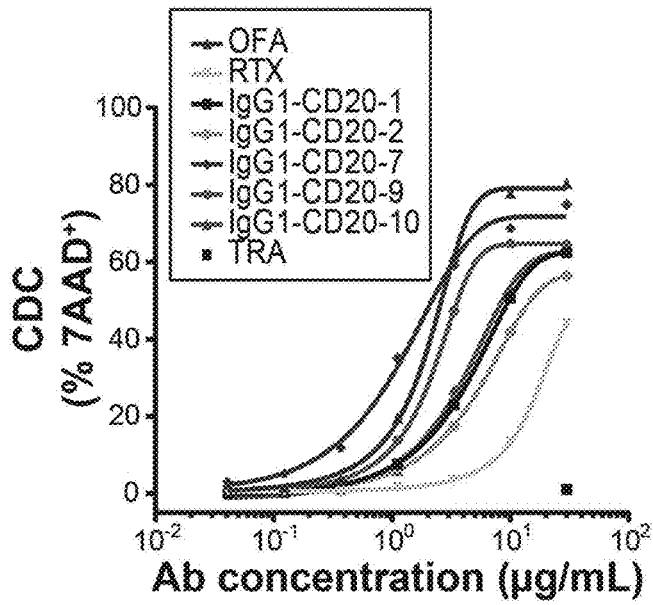

Tumor cell killing by activation of the complement system is the second effector mechanism commonly induced by IgG1-CD20 mAbs. The chIgG1-CD20 mAbs showed a concentration dependent tumor cell lysis (FIG. 9B). All mAbs induced a higher degree of CDC compared to RTX. IgG1-CD20-2 remained the least potent one. IgG1-CD20-1 and IgG1-CD20-10 performed similar, and IgG1-CD20-7 even better than OFA at lower concentrations.

The last mechanism of action described to be induced by CD20 mAbs, is tumor cell death by programmed cell death (PCD). This property is strongly induced by so called Type II CD20 mAbs like Obinutuzumab (OBZ)[12] and B1

Figure 9C:
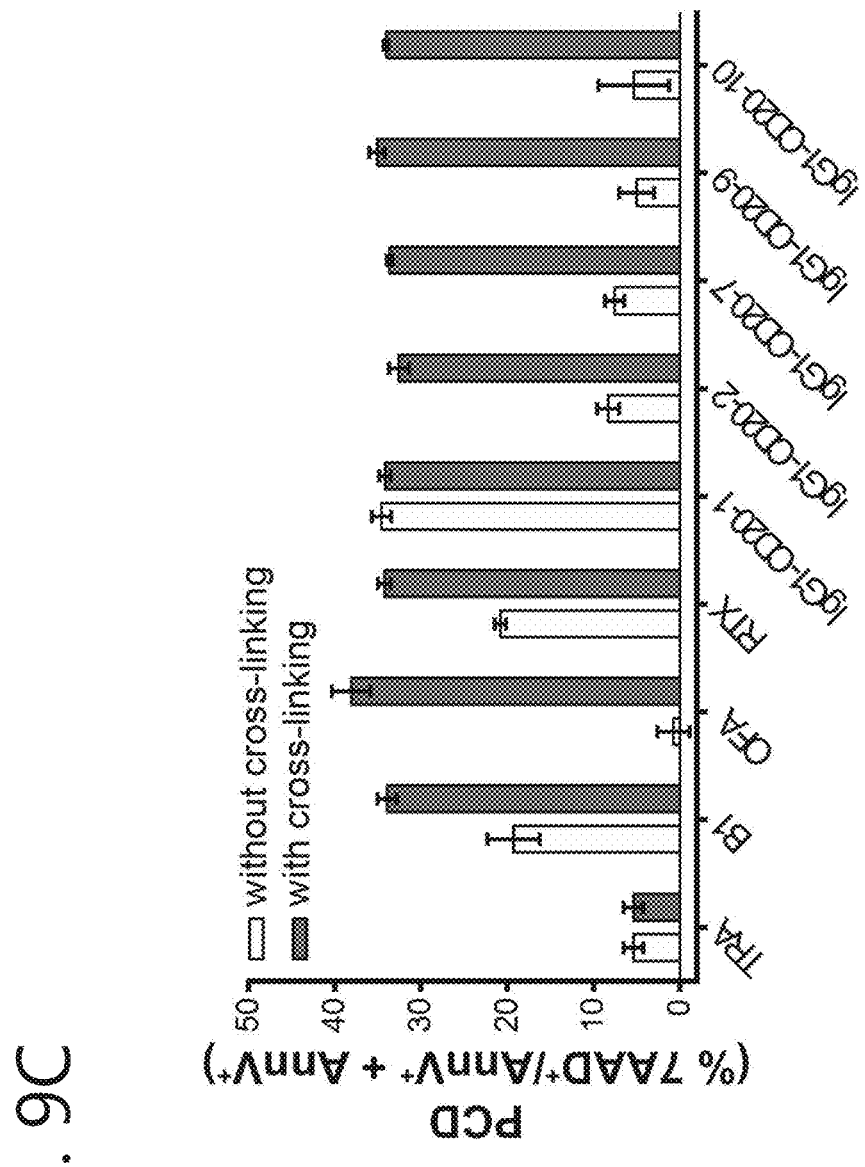
Figure 9E:
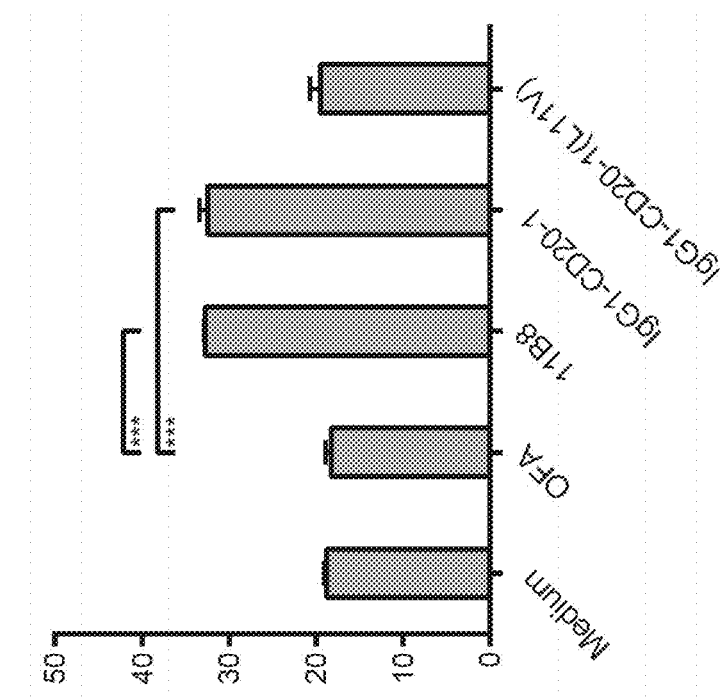
Figure 9D:
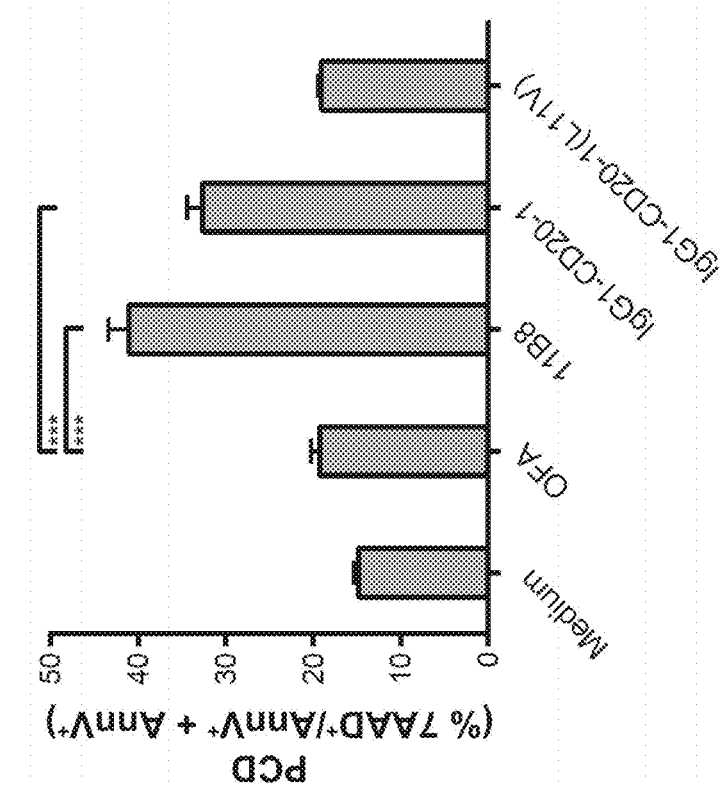
Figure 9G:
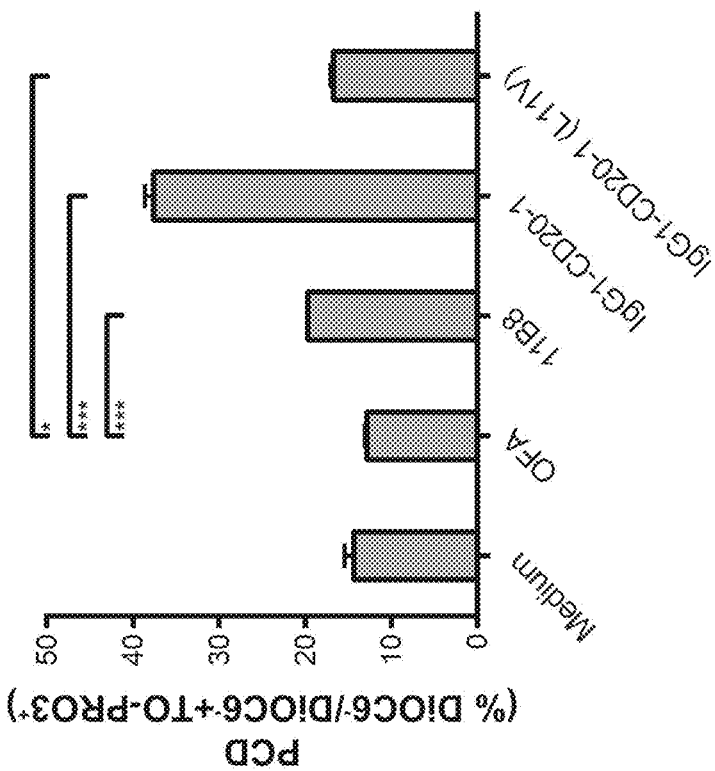
Figure 9F:
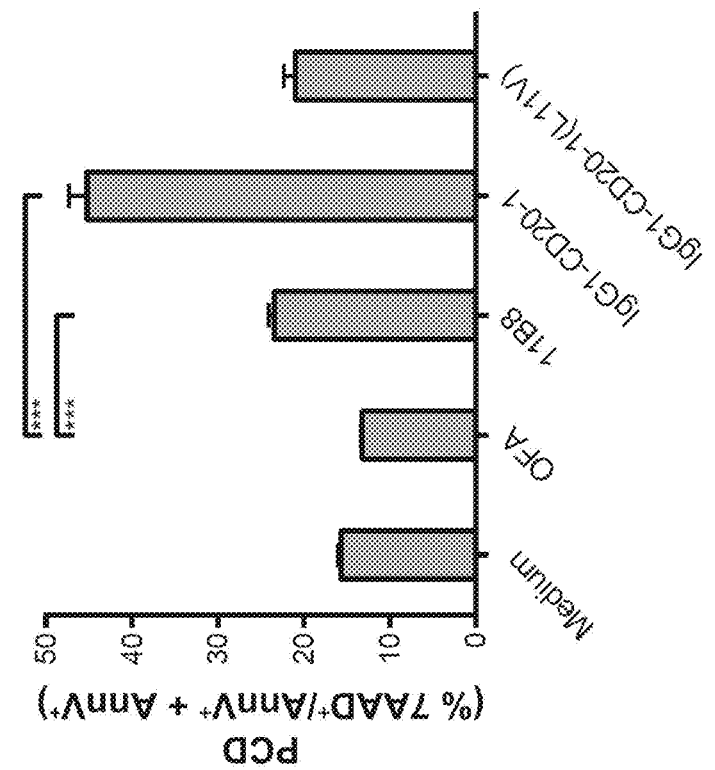

(mIgG2a CD20 mAb).[13] RTX was shown to kill tumor cells to a lower extent via the same caspase-independent pathway.[15] None of the parental mouse CD20 mAbs induced neither homotypic aggregation, as sign for cell death induction, nor an increase in 7-AAD and AnnexinV positivity. As described in Example 1, IgG1-CD20-1 induced PCD of EL4-CD20 cells. Here, the full IgG1-CD20 mAb panel was compared, however, for the other 4 CD20 mAbs, chimerization did not change these characteristics (FIG. 9C).

Figure 10A:
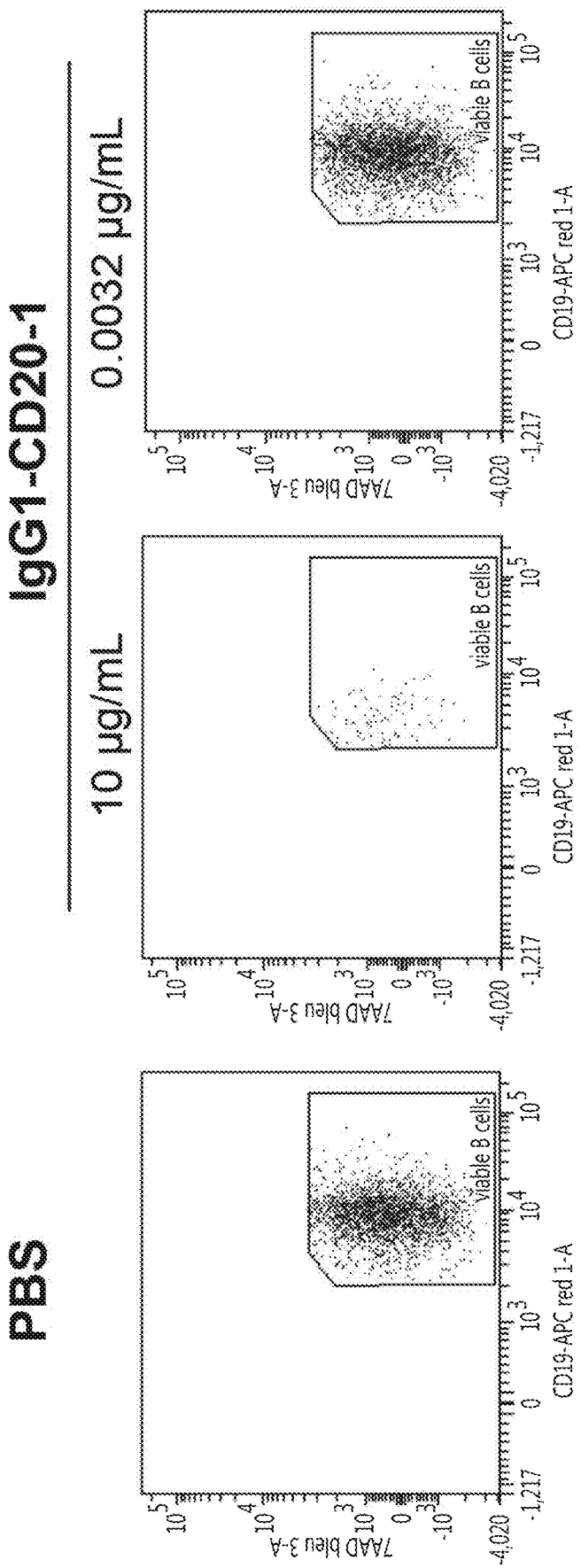
FIGS. 10A, 10B. Disappearance of CD19+ viable B cells in autologous setting. B-cell depletion by CD20 mAbs was determined by incubating mAbs for 1 hour at 37° C. with unprocessed blood from healthy donors.
Figure 10B:
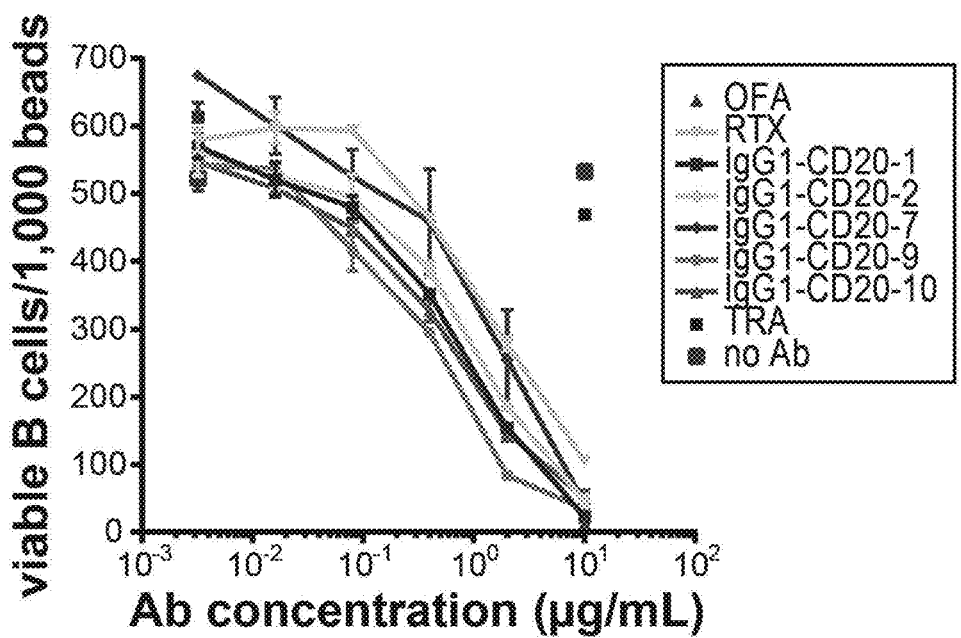

Finally, the degree of B-cell depletion in an autologous whole blood assay was assessed. An increase of 7AAD$^+$ CD19$^+$ B cells upon incubation with mAb at any concentration was not observed, the focus was only on the number of viable CD19$^+$ B cells (FIG. 10A). A mAb concentration dependent decline of viable CD19$^+$ B cells (FIG. 10B) was detected. RTX as the weakest CDC inducer performed the worst. No clear differences could be observed between the new IgG1-CD20 mAbs.

Figure 11:
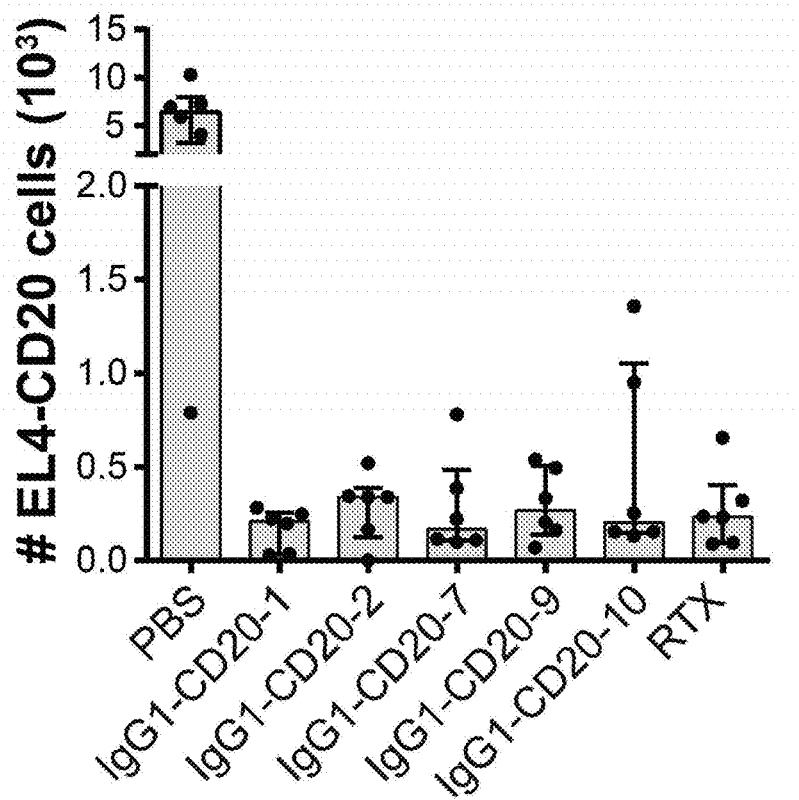
FIG. 11. In vivo efficacy of IgG1-CD20 mAbs. C57BL/6 mice (6 mice/group) were injected intraperitoneally with $5 \times 10^5$ CellTraceViolet labeled EL4-CD20 cells 16 hours prior to mAb (10 µg) or PBS treatment. The anti-tumor response was evaluated 24 hours later by determining the amount of remaining tumor cells in the peritoneal lavage with TruCount tubes (median±interquartile range).

Eventually, using the previously established EL4-CD20 low tumor burden model, it was determined at a fully saturating concentration of 10 μg mAb the efficacy of the chimeric IgG1-CD20 mAbs. No major differences were detectable, but all mAbs showed a potent induction of tumor cell killing in vivo (FIG. 11).

Discussion

Starting with mouse sequences, an important step before humanization is to test chimeric mAbs for their therapeutic potential. Five new chimeric IgG1-CD20 mAbs were generated, and they all induced tumor cell killing in vitro and in vivo. Differences in their ADCC and CDC activity however, did not translate into a better anti-tumor response in vivo.

OBZ, a potent ADCC and PCD inducer, was shown to prolong survival of SCID mice more efficiently than RTX in a NHL xenograft model.[12] However, the individual contribution of ADCC or PCD to the efficacy has not been evaluated yet.

The potential of CD20 mAbs has been studied extensively in whole blood B-cell depletion assays. Commonly, 4 hours to 24 hours incubation times were used.[12, 50, 51] It was shown that OBZ exhibits superior and faster killing of B cells in an autologous setting of healthy but also patient donor blood compared to RTX. However, in those assays all effector mechanisms are likely to contribute. The mAbs was incubated for 1 hour with unprocessed blood. This set-up is beneficial for the evaluation of complement-mediated rather than effector cell-mediated tumor cell killing. CDC is quickly induced, whereas NK-cell-mediated tumor cell eradication requires longer incubation times. This possibly explains the poor results obtained with RTX, the weakest complement activator. The effectiveness of the new CD20 mAbs in the B-cell depletion assay correlated with obtained CDC results. Next to donor variability, a decrease of CD19 expression within the lymphocyte gate was detected, indicating an influence of CD20 mAb treatment on CD19. It was previously shown that RTX treatment induces CD19 shaving or trogocytosis, a neutrophil- and monocyte/macrophage-mediated mechanism.[9-11] As this seems to be a very fast effect, alternative strategies to determine the B-cell depletion potential of CD20 mAbs in an autologous setting are being investigated. Here, CD24 as a secondary B-cell marker is going to be explored. The findings demonstrate that functional characteristics displayed by mouse IgG mAbs are not predictive for a chimer (Table 2). The antibody GA101 (obinutuzumab) does not have significant complement activity see Herter et al (2013) Mol Cancer Ther. 12(10):2031-42. doi: 10.1158/1535-7163.MCT-12-1182.

Example 3

IgG1-CD20 monoclonal antibodies (mAbs) like rituximab, ofatumumab and obinutuzumab are used in the clinics to treat patients diagnosed with different kinds of B-cell malignancies. For IgG1-CD20 mAbs various mechanisms-of-action are known to contribute to the eradication of tumor cells:[56-61] (a) antibody-dependent cytotoxicity and phagocytosis (ADCC/ADCP) mediated by the engagement of Fc gamma receptors (FcγR) on predominantly natural killer cells and monocytes/macrophages; (b) activation of the classical complement pathway by binding C1q, resulting in tumor cell lysis by CDC; (c) induction of PCD upon direct binding to CD20 molecules. Additionally, it was suggested that the treatment with mAbs can induce an adaptive cellular immune response. Findings by Abès and colleagues showed that an Fc-mediated response results in a long-lasting protection of immunocompetent mice after tumor re-challenge.[62] The induction of cytotoxic T-cells might be initiated by dendritic cells, which cross-present tumor-derived peptides after phagocytosis of Ab-opsonized target cells.[63, 64] This long-term anti-tumor immunity has not yet been shown in patients, but might explain why for some patients a durable tumor regression can be achieved with CD20 mAbs.

The engagement of effector cells required for the induction of an anti-tumor response by IgG1-CD20 mAbs relies on the interaction with FcγR. However, single nucleotide polymorphisms (SNPs) within FcγRIIa and FcγRIIIa have been associated with better or worse treatment outcomes.[65-68] Furthermore, due to unknown reasons not all patients respond to IgG1-CD20 mAb therapy. Patients that relapse or develop resistance after rituximab treatment have also been reported.[69-73] Thus, alternative treatment options are required to overcome these limitations. One possibility is the use of a different Ab isotype, namely IgA. IgA is the second most prominent antibody in blood, after IgG, and the predominant Ab at the mucosa. The monomeric version of IgA is mostly found in serum, whereas polymeric IgA is produced at mucosal sites. The 2 Ab subclasses, IgA1 and IgA2, differ structurally in their hinge regions, which is 13 amino acids longer for IgA1 than for IgA2. This might enable an improved reach for antigens that are distant, but at the same time makes it more prone to degradation by proteases.[36] Furthermore, the hinge region of IgA1 mAbs carries several O-linked glycosylation sites, which are absent in IgA2 mAbs. IgA2 exists as 3 allotypes; IgA2(m1) has 2 additional N-linked glycosylation sites compared with IgA1, and IgA2(m2) and IgA2(n), which have 3 additional N-linked glycosylation sites. Contrary to IgG, IgA is a weak activator of the classical complement pathway as it cannot bind C1q.[37] However, IgA mAb have been shown to activate the complement system through the lectin pathway, as the carbohydrate recognition domain (CRD) of mannan-binding lectin (MBL) can bind to IgA[38]

IgA engages immune effector cells by binding to the FcαRI (CD89), which is expressed on cells of the myeloid lineage: neutrophils, monocytes, different macrophage populations and eosinophils.[39] Expression on in vitro generated dendritic cells was shown,[23, 24] but remains controversial. Neutrophils express high levels of the FcαRI, while macrophages have lower expression.[42] In ADCC assays with IgA mAbs targeting solid tumor targets, neutrophils have been shown to efficiently eradicate tumor cells.[43-46] In contrast, IgG1 mAbs were less able to engage this effector cell population. Monocyte/macrophage-mediated tumor cell killing was shown to be comparable between IgA and IgG mAbs.[44] Next to the activating FcγRIIIa, macrophages also express the inhibitory FcγRIIb. It has been shown that the presence of FcγRIIb reduces mAb activity.[47] For IgA, no inhibitory receptor has been described yet.

The knowledge on IgA mAb targeting tumor-associated antigens has increased significantly over the last few years. Several bottlenecks that were faced a few years ago are now overcome, and are currently able to produce and purify sufficient amounts of monomeric IgA mAbs for in vitro and in vivo testing. Mice lack a receptor for IgA, therefore the generation of human FcαRI transgenic now allows in vivo testing.[48] Boross and colleagues eventually showed in an immunocompetent tumor model the great potential of IgA mAbs in a therapeutic setting.[44] The majority of IgA mAbs studied so far are targeting Her2 or EGFR, antigens expressed on solid tumors. Only one study has looked at the potential of monomeric IgA-CD20 mAbs.[49] Complement-mediated tumor cell killing was demonstrated to rely on weak indirect activation of the classical pathway and more pronounced direct activation of the alternative pathway. With a passive immunization strategy in FcαRI transgenic mice, a good protection against tumor development with monomeric IgA2-CD20 mAbs was achieved. However, therapeutic in vivo testing for IgA-CD20 mAbs has not yet been performed. Further, a direct comparison of IgA1 and IgA2 mAbs, in particular, with respect to their complement activation properties is lacking. Therefore, the goal of the current study was to generate several IgA-CD20 mAbs of the different subclasses and characterize them. Described here is the preliminary in vitro characterization of unique IgA1- and IgA2-CD20 mAbs. The previously generated mIgG2c-CD20 mAbs m1 and m2 (Example 1) were selected to be produced as IgA1 and IgA2 variants. Their preliminary in vitro characterization revealed promising potential.

Material and Methods

Antibodies

The following antibodies were used in experiments as positive or negative controls: rituximab (RTX; Pharmacy UMC Utrecht), anti-hCD20-hIgA2 (IgA2-RTX; Invivo-Gen), anti-hCD20-hIgA1 (IgA1-RTX; InvivoGen); IgA1- and IgA2(m1)-Her2 (own production), ofatumumab (OFA, Pharmacy UMC Utrecht), B1 (mIgG2a-CD20 mAbs, kindly provided by Mark Cragg, University Southhampton, UK), and trastuzumab (TRA, Pharmacy UMC Utrecht).

Cell Lines

The Burkitt lymphoma cell lines Ramos and Raji (ATCC) were maintained in RPMI culture medium containing RPMI-1640+HEPES+glutamine (Invitrogen) supplemented with 10% FCS and 1× P/S at 37° C./5% $CO_2$. EL4-CD20 cells were generated as previously described[23] and cultured in RPMI culture medium.

Production of IgA-CD20 mAbs

The variable heavy and light chain (HC and LC) sequences (synthesized by ShineGene) were flanked by the HindIII and NotI restriction sites. The variable regions were cloned into the Lonza vectors pEE14.4-kappaLC, pEE14.4-IgA1, and pEE14.4-IgA2(m1).

For transient antibody production, the HEK FreeStyle™ 293F Cell (Invitrogen) system was used as previously described.[22] Briefly, HEK293F cells were transfected with LC, HC and pAdVAntage™ Vector (Promega) DNA diluted in Opti-MEM (Life Technologies) together with 293fectin™ Transfection Reagent (Life Technologies). After 4 hours 1× P/S (Gibco) was added. Supernatant was harvested 4 days post transfection, filtered and stored until purification at 4° C.

All column purification steps were performed using the AKTAPrime plus system (GE Healthcare). The antibody containing supernatant was diluted 1:1 with the binding buffer (1× PBS; Sigma-Aldrich) and IgA mAbs were purified using a 5 mL HiTrap KappaSelect column (GE-Healthcare). Bound protein was eluted from the column with 0.1 M Glycine, pH 2.5. Fractions were collected, directly neutralized with 1 M Tris, pH 8.8 and pooled based on protein concentration determined by A280 absorption measured on a Nanodrop. Protein containing fractions were subjected to size-exclusion chromathography (SEC) using a HiPrep 26/60 Sephacryl S-300 High Resolution column (GE Healthcare). Fractions containing the monomeric IgA mAbs were collected, pooled, and concentrated using VivaSpin concentration columns (100 000 MWCO; Sartorius). End concentrations of the IgA mAbs were determined by Nanodrop using the following formula:

$$\frac{OD \text{ value at } 280 \text{ nm}}{\text{correction factor (monomeric } IgA \text{ 1.4)}}.$$

IgG and IgA ELISA

A 96-well plate (NUNC maxisorp) was coated with goat-anti-huKappa (Southern Biotech) diluted in 1×PBS (Sigma-Aldrich) at 4° C. overnight. After blocking with 1% BSA/0.05% Tween-PBS and washing with 0.05% Tween-PBS, samples were added and incubated for 90 minutes at room temperature. Samples and standards were diluted in 1% BSA/0.05% Tween-PBS. Purified huIgA (Bethyl Lab) was used as a standard for IgA mAbs. Washed plates were incubated with goat-anti-human IgA-HRP (Southern Biotech) diluted in 0.05% Tween-PBS as secondary antibody for 1 hour at room temperature. Bound antibodies were detected with ABTS (Roche) and subsequent measurement at 405 nm with a Multiscan RC (Thermolab systems).

CD20 Binding Assay $10^5$ Ramos cells were plated out in a 96-wells plate and incubated with mAb diluted in 1×PBS for 45 minutes on ice. After extensive washing, bound Abs were detected by incubating the cells for 45 minutes on ice with goat-F(ab$^1$)$_2$-anti-humanIgA-RPE (Jackson ImmunoResearch). Cells were fixed with 1% paraformaldehyde before measuring them on the FACS Canto II (BD).

CDC Assay $10^5$ Daudi or Ramos cells were opsonized with mAbs diluted in RPMI culture medium for 30 minutes at room temperature. Next, 15.5% normal human serum (NETS) pooled from 8 donors was added and the mixture incubated for different time spans (15, 60, 240, and 360 min) at 37° C. Serum for blocking experiments was treated before addition to the cells by heat-inactivation (30 minutes at 56° C.), pre-incubation with 10 mM EGTA+2 mM $MgCl_2$, or addition of eculizumab (anti-C5 mAb) at a mAb:C5 molar ratio of 5:1 for 15 minutes at room temperature. Cells were washed with 1×PBS and dead cells stained with 7-AAD (BD Pharmingen) for 15 minutes at room temperature. Samples were measured on a FACS Canto II (BD) and complement-dependent tumor cell lysis was determined as the percentage of 7-AAD positive cells.

Cell Death Induction Assay 0.4×10$^5$EL4-CD20 cells were incubated with 1 μg/mL mAb for 24 hours at 37° C. Cross-linking Abs (20 μg/mL rabbit F(ab')$_2$-anti-hIgG; 50 μg/mL rabbit F(ab')$_2$-anti-mIgG, and 20 μg/mL goat F(ab')$_2$-anti-human serum IgA; Jackson) were added 30 minutes after incubation of the cells with the CD20 mAbs. Samples were collected, washed with Annexin V binding buffer and incubated with a mix of AnnexinV-APC and 7-AAD (both BD Pharmingen) for 15 minutes at room temperature. Cells were measured on a FACS Canto II and the extent of programmed cell death was determined as % AnnexinV$^+$/7-AAD$^+$+% AnnexinV$^+$ cells.

B-Cell Depletion Assay

All leukocytes were isolated from healthy donor blood collected in Heparine tubes by Histopaque-ficoll density gradient and subsequent lysis of residual erythrocytes using eryhtrocyte lysis buffer (155 Mm ammonium chloride, 0.1 mM EDTA and 10 mM potassiumbicarbonate, pH 7.4). Isolated leukocytes were combined with antibody dilutions in a 96-well plate at 0.2×10$^6$ leukocytes/well and incubated for 3 hours at 37° C./5% CO$_2$. The supernatant was removed after centrifugation, cells washed with ice-cold PBS/0.1% BSA (FACS buffer) and stained with an antibody mix containing mouse-anti-human CD19-APC (Biolegend), mouse-anti-human CD11b-PE (BD Pharmingen), mouse-anti-human CD14-V500 (BD Pharmingen), mouse-anti-human CD56-AlexaFluor488 (clone B159, BD Pharmingen), and mouse-anti-human CD3-PerCp (Biolegend) for 30 minutes on ice. After washing, cells were resuspended in FACS buffer containing Cyto/Cal Multifluor Plus Violet Flow Cytometer Alignment Beads (Thermo Scientific), and flow cytometry was performed using a BD FACS Canto™ II.

Human PMN ADCC

ADCC assays with $^{51}$Cr-labeled target cells were performed as previously described. Briefly, PMNs were isolated from healthy individuals (MiniDonorDienst UMC Utrecht) by Ficoll/Histopaque separation (GE Healthcare; Sigma-Aldrich). $^{51}$Cr-labeled Daudi cells were combined with PMNs (effector-to-target ratio=40:1) and CD20 mAb in dilution. After 4 hours incubation at 37° C./5% CO$_2$, the supernatant was harvested and counted in a liquid scintillation counter (MicroBeta; Perkin Elmer). Lysis was calculated using the following formula:

$$\% \text{ lysis} = \frac{counts_{sample} - counts_{minimal\ release}}{counts_{maximum\ release} - counts_{minimal\ release}} \times 100.$$

Daudi cells with effector cells in RPMI culture medium or in medium supplemented with 2.5% Triton X-100 (Roche Diagnostics) were used to determine minimal and maximum release, respectively.

Results

Antibody Production and Purification

Figure 12A:
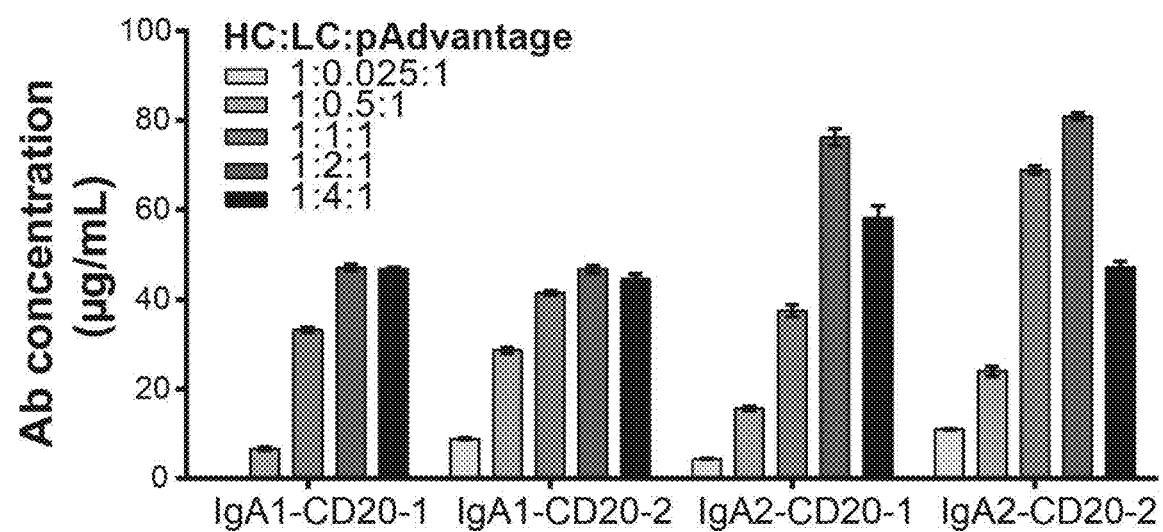

The IgA1 and IgA2 mAbs were produced by transfection of HEK293F cells. First, the optimal ratio between heavy chain, light chain and pAdvantage DNA was determined in a small scale test transfection. For all mAbs, a 1:2:1 ratio to result in the highest production (FIG. 12A) was found. The new mAbs were subsequently produced by a linear upscaling approach. The full-size mAbs were isolated by a two-step purification protocol, including 1) anti-kappa purification (FIG. 12B) and 2) size-exclusion chromatography (SEC) (FIG. 12C). Whereas the kappa purification peaks look the same for both subclasses, a different pattern could be observed during the SEC. Next to the full-size Abs, IgA1 samples contained higher levels of loose kappa light chains (FIG. 12C left). In contrast, IgA2 samples contained more Ab conjugates (shorter retention time; FIG. 12C right). The yields of full-size mAbs obtained after SEC were comparable between both subclasses. Purity and integrity of the purified IgA mAbs was assessed by SDS-PAGE (data not shown).

Functional Characterization

First, the ability of the antibodies to bind to CD20-expressing Ramos cells (FIG. 13) was assessed. Binding capacity was in the same range for all IgA2-CD20 mAbs. However, IgA1 mAbs had a better binding capacity compared to the IgA2 mAbs.

Figure 14:
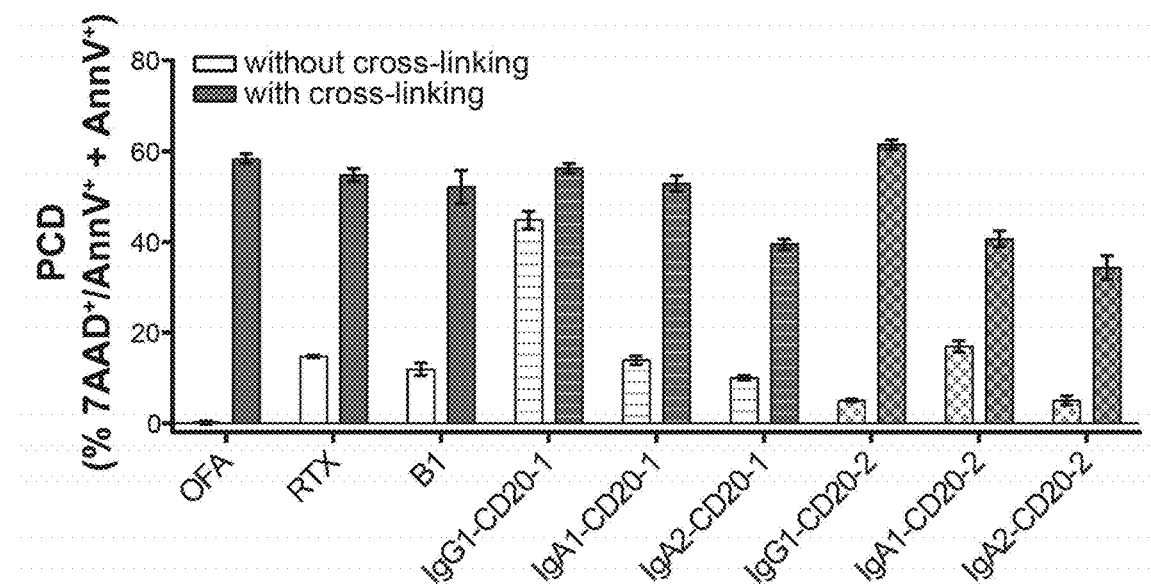
FIG. 14: Variable extent of programmed cell death induction by IgA-CD20 mAbs. EL4-CD20 cells were incubated for 24 hours with 1 µg/mL mAb in the absence and presence of cross-linking Ab (B1: 50 µg/mL; IgG1 and IgA mAbs: 20 µg/mL). The degree of cell death was determined as the sum of AnnexinV+ and AnnexinV+/7AAD+ cells ($value_{sample}-mean_{medium}$+SEM). B1 (mIgG2a-CD20 mAb) and RTX were taken along as positive controls and OFA as a negative control.

Next, the functionality of the newly synthesized antibodies was tested. A subset of IgG-CD20 mAbs, known as Type II CD20 mAbs, induces PCD upon binding to their target. The IgA mAbs was subjected to a cell death induction assay. The incubation of EL4-CD20 tumor cells with the mAbs for 24 hours led to a marginal increase of PCD by the new IgA-CD20 mAbs (FIG. 14). This was slightly more pronounced for IgA1 than IgA2 mAbs.

Figure 15A:
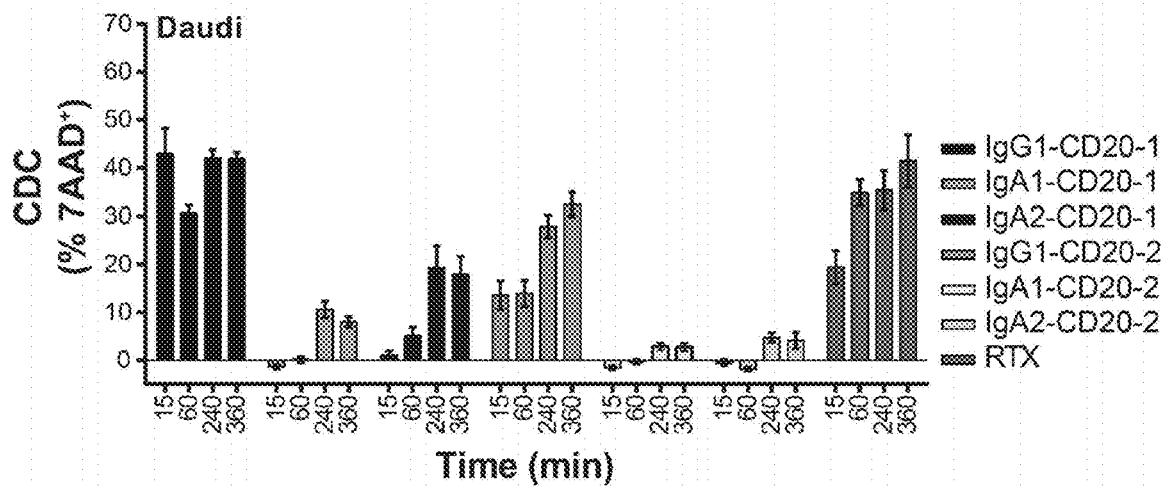
FIGS. 15A-15C: Complement-dependent cytotoxicity induced by IgA-CD20 mAbs. Target cells were incubated for indicated time with 15.5% pooled human serum and degree of CDC was determined as % 7AAD+ cells.
Figure 15B:
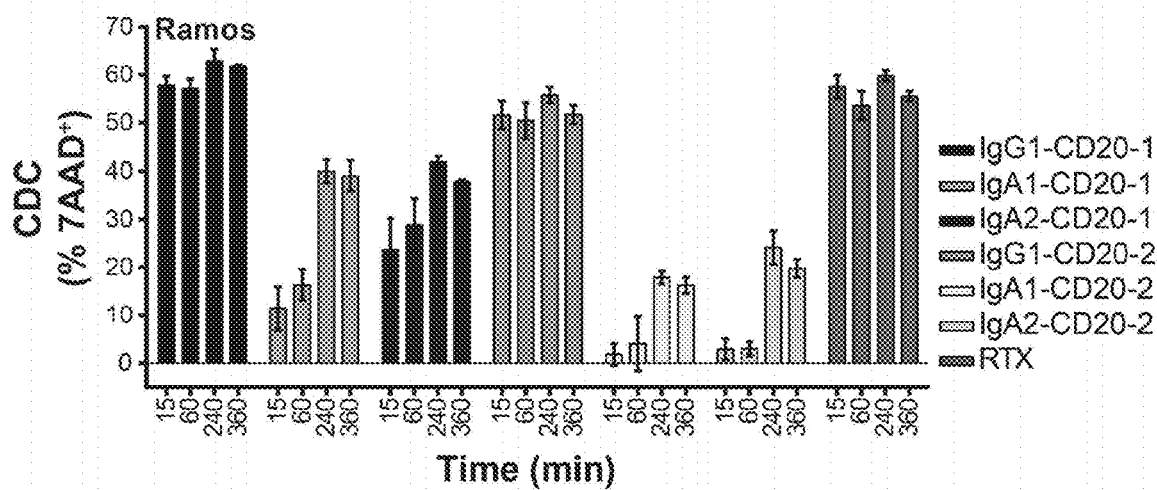
Figure 15C:
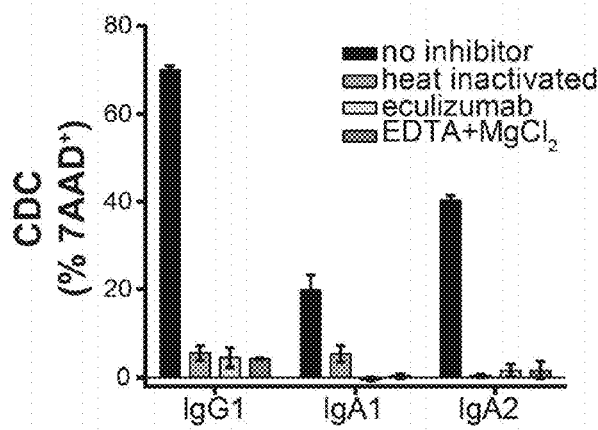

Subsequently, the ability of IgG1- and IgA-CD20 mAbs was compared to induce CDC. Complement-mediated lysis of Daudi cells was observed already after 15 minutes with IgG1-CD20 mAbs, but not with IgA-CD20 mAbs (FIG. 15A). Minor CDC induction by IgA-CD20-1 mAbs was seen after 60 minutes incubation with complement active serum, which increased with longer incubation times. Unexpectedly, Ramos cells, which express less CD20, but higher levels of CD46 and CD59 than Daudi cells, were more susceptible to CDC (FIG. 15B). Furthermore, IgA1-CD20 complement-mediated lysis was delayed but reached a comparable level as IgA2-CD20 mAbs after 240 minutes. To confirm that the IgA-CD20-1 induced lysis was mediated by complement activation, CDC assays were performed in the presence of different complement inhibitors (FIG. 15C). The lysis induced by IgA-CD20-1 mAbs was abolished when heat-inactivated serum and serum pre-treated with eculizumab (anti-C5 mAb), was used. To determine if the alternative pathway is engaged by IgA mAbs, EGTA+MgCl$_2$ was used to inhibit the classical and lectin pathway. Lysis was reduced to background levels not only for IgG1, but also by IgA-CD20-1 mAbs.

After determining the ability of the new IgA-CD20 mAbs to induce PMN-mediated tumor cell lysis in a chromium release assay, the potential of the IgA-CD20 mAbs to deplete human B cells was then analyzed. Incubation of leukocytes from healthy donors with the mAbs resulted in a concentration-dependent decline of CD19$^+$ events (FIG. 16A). This effect was comparable between RTX and the IgA-CD20 mAbs. The number of CD19$^+$ events (FIG. 16B) steadily decreased for all IgA-CD20 mAbs and reached a plateau between 0.05 and 0.5 µg/mL mAbs. In contrast, the number of CD19$^+$ events upon RTX incubation reached a minimum at 0.05 µg/mL, but increased at higher concentrations again. For both isotypes, the number of CD19$^-$ events reached an optimum between 0.05 to 0.5 µg/mL (FIG. 16C).

Discussion

At the moment, all CD20 targeting mAbs on the market are of the IgG1 isotype. The varying response to the treatment stresses the need to develop alternative therapies. In the recent years, researchers have investigated the anti-cancer potential of IgA mAbs targeting, in particular, solid tumor targets like Her2 and EGFR.[43-46, 74] Here, the comparison of IgA1-CD20 and IgA2(m1)-CD20 mAbs is described, which have unique variable domain sequences of two previously selected mouse mAbs. Functional characterization of the parental mouse mAbs m1 and m2 showed distinct behavior in their complement-mediated tumor cell lysis capacity, binding kinetics and epitope recognition (Example 1).

Fab- and Fc-mediated mechanisms were studied leading to the eradication of tumor cells as described for IgG1 mAbs. Some IgG1-CD20 mAbs (e.g., Obinutuzumab and B1) elicit tumor cell killing upon binding to CD20 (Fab-mediated effect). PCD with IgG1-CD20-1 was observed, but not IgG1-CD20-2. In contrast, both IgA-CD20-1 and IgA-CD20-2 induced PCD, albeit at a low level, indicating that this mechanism-of-action for IgA mAbs is independent of the epitope. To strengthen this hypothesis, other known antibodies that differ in their PCD capacity as IgG1 and target different epitopes (e.g., RTX and Obinutuzumab) would need to be compared as IgA variants.

CDC induced by IgG1 is an efficient Fc-mediated mechanism to lyse tumor cells. IgG1-CD20 mAbs activate the classical complement pathway by binding C1q. However, the activation of this pathway is unlikely for IgA mAbs as they lack the C1q recognition site.[37] In literature it was described that IgA Abs isolated from human serum bind MBL.[38] This resulted in C3 deposition, indicating the engagement of the lectin pathway. Still, Pascal and colleagues showed that IgA2-CD20 mAbs lyse a subset of $CD20^+$ tumor cell lines by directly activating the alternative and indirectly engaging the classical pathway.[39] With the data, the involvement of CDC in tumor cell killing by IgA mAbs was confirmed. However, the results exclude activation of the alternative pathway. To further dissect the contribution of the different complement pathways, additional experiments have to be performed with specific inhibitors. For example, C1q depleted serum can be used to block the classical pathway, Factor B depleted serum for inhibition of the alternative pathway, and MASP-1 or MASP-2-specific inhibitors to block the lectin pathway.[75, 76] For the first time, both subclasses next to each other were compared and it showed that IgA2 mAbs are faster at inducing CDC than IgA1 mAbs. This discrepancy might be a consequence of the differential glycosylation pattern of the heavy chain of IgA1 (2 N-linked glycans) and IgA2(m1) (4 N-linked glycans), resulting in a better activation of the lectin pathway by IgA2.

Properties like target antigen expression level, expression of membrane bound complement-regulatory proteins, the epitope, and binding kinetics have been implicated to influence IgG1-mediated CDC. Thus far, only a role for the epitope of IgA mAbs, as IgA-CD20-1 mAbs, could be established, derived from mIgG with better CDC activity, also activate complement better than IgA-CD20-2 mAbs. Whether the other properties are also important, needs to be elucidated.

ADCC by FcαRI expressing effector cells has been shown to be mediated faster by PMNs than by monocytes/macrophages. To determine the role of these immune effector cells in IgA-CD20-mediated B-cell depletion, $CD19^+$ B cells were depleted in an autologous setting in the absence of a complement source. mAb-mediated depletion of $CD19^+$ cells was generally better for IgA-CD20 mAbs than for RTX, with IgA1-CD20 mAbs performing the best. However, both isotypes induce the loss of CD19 expression. This is in line with previously published findings that B cells from healthy donors incubated with RTX lose their CD19 expression without undergoing cell death.[52] The same antigenic modulation was described for CD20, with 75-90% reduction in less than 45 minutes.[55] Neither shedding nor internalization were implicated in the loss of CD19. Instead, shaving/trogocytosis in an Fc-dependent manner, particularly mediated by neutrophils and monocytes, was described as the mechanism-of-action. It is speculated that the stronger engagement of PMNs by IgA mAbs compared to IgG1 mAbs eventually leads to tumor cell death by trogocytosis.[53, 54]

The therapeutic dose of RTX should be carefully determined, as too high concentrations were shown to decrease Ab efficacy in the in vitro B-cell depletion assay. In contrast, this effect was not observed with IgA-CD20 mAbs. Nonetheless, as CD20 mAbs modulate the expression of B-cell markers, B-cell tracking might represent a better approach to properly determine mAb-mediated B-cell depletion.

Example 4

Characteristics of IgA CD20 Antibodies.

Figure 17:
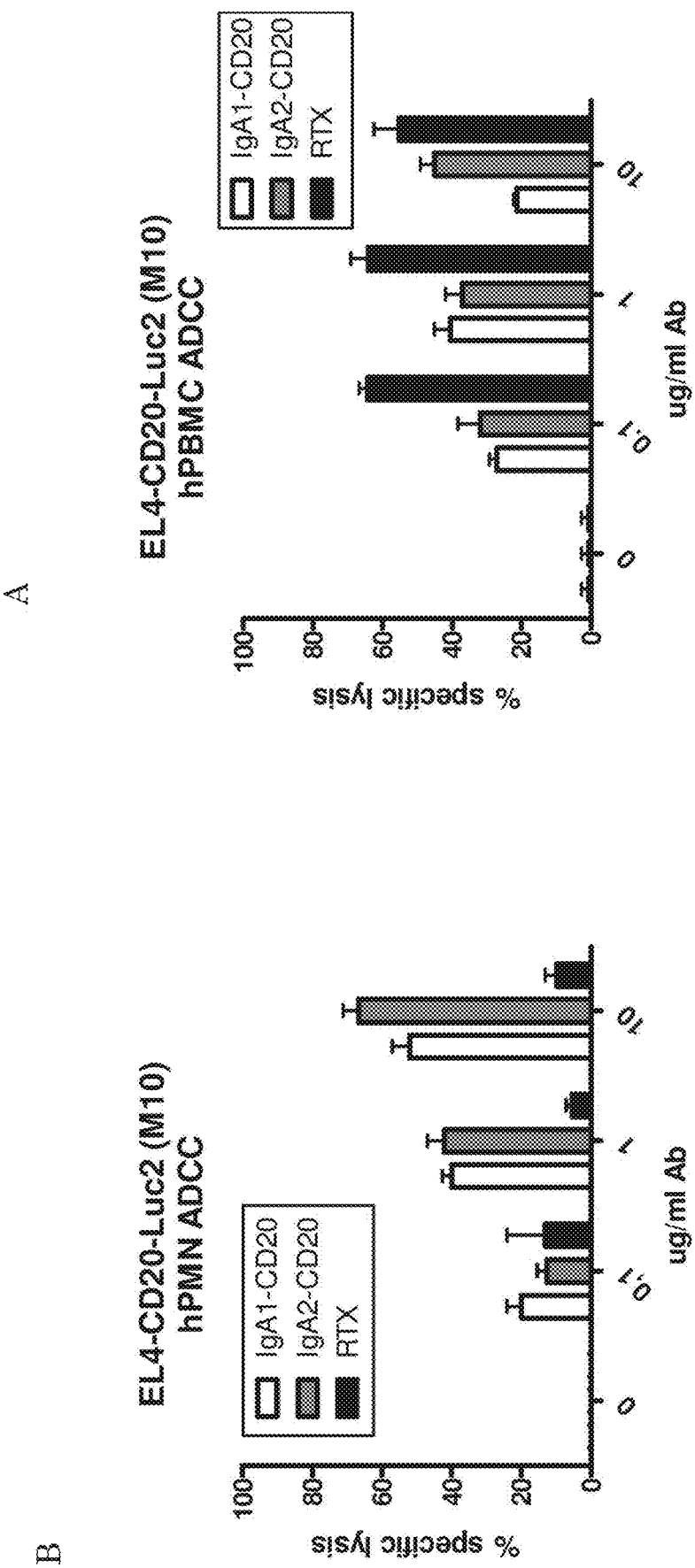
FIG. 17. Anti-CD20 IgA mediates efficient tumor cell lysis of CD20 targets. ADCC as measured by the release of $^{51}$Cr from EL4-CD20-Luc2 cells using (Panel A) PBMC, E:T=100:1, or (Panel B) PMN, E:T=40:1, as effector cells and the indicated antibody concentrations. Anti-CD20 IgA's contain the same variable regions as rituximab.

The human body uses IgA do defend itself against pathogens, predominantly on the mucosa barrier. It kills pathogens either via direct mechanisms or via neutrophil activation. Very low quantities of IgA can effectively trigger neutrophils via the Fcα receptor (FcαR). Importantly, neutrophils are far more effective killer cells than NK cells and possess excellent tissue penetration capacity. Thus, IgA seems an attractive antibody class for tumor immunotherapy. Nevertheless, it is difficult to develop clinical IgA antibodies. Until recently, there were no good in vivo model systems for IgA immunotherapy since mice lack expression of the FcαR. The research group has developed a transgenic mice that expresses human FcαR (CD89) on neutrophils. With this mouse model, it is demonstrated that therapeutic IgA antibodies can effectively defend mice against tumor outgrowth in several in vivo models, long-term and short-term on different locations, and in immunocompetent mice6. Using a unique locally developed immunization method, a broad panel of novel CD20 antibodies (all IgG) was obtained. Two of these antibodies have clinical potential, killing tumor cells in vitro more effectively than all currently available clinical CD20 antibodies. Both antibodies have now been transformed into chimeric antibodies with human IgA Fc fragment (+/−70% huIgA) and currently explored for their efficacy (FIG. 17).

CD20 Internalization

It has been described in references 77-79 that certain antibodies that are used therapeutically in lymphoma treatment (eg, rituximab and ofatumumab) undergo Fcγ receptor IIb (FcγRIIb)-mediated internalization from the B-cell surface with important implications for antibody-based therapeutics.

FcγR expression on target cells themselves is critical for this Ab-CD20 complex internalization. Immune effector cell Fc-FcγR interactions in trans act to deplete the target cell, particularly when the antigen is expressed at high levels. Although the importance of activating FcγR for the efficacy of rituximab in xenograft models was demonstrated before, now it is known that the inhibitory FcR, FcγRIIb, expressed on certain types of B-cell malignancies, also plays a role in Ab-CD20 complex internalization. FcγRIIb contains an immunoreceptor tyrosine-based inhibitory motif that recruits specific phosphatases and acts to oppose signaling by activating FcγRs. FcγRIIb-mediated internalization of rituximab from the B-cell surface was shown to limit effector cell engagement, an effect that may be particularly important in malignancies such as chronic lymphocytic leukemia and mantle cell lymphoma that express high levels of FcγRIIb and show reduced responses to CD20 mAb therapy.

This effect was not seen with the IgA antibodies of antibodies m1, m2, m7, m9, m10. These do not have this negative side effect. Indeed, when B cells were isolated from blood of healthy volunteers, CD20 IgG antibodies show a decrease of the CD20 target molecule of 40 to 60 percent, whereas with the IgA antibodies remained at a level of 80% on the cell surface of B cells (see FIGS. 25, 26.1, 26.2 and 26.3), suggesting that IgA antibodies have a diminished side effect on therapy compared to IgG antibodies.

Methods for CD20 Internalization

PBMC were separated from healthy donors by ficoll (GE healthcare) density gradient and used for B cell isolation using MACS human B cell isolation kit II (Milteny biotec). 5×10e4 isolated B cells were seeded in conical 96 wells plates and incubated with 1 ug/ml AlexaFluor 488 (AL488) labeled (Molecular Probes) Ab for 3 hours at 37° C./5% CO2. Unbound Ab was washed away and the AL488 signal quenched using 25 ug/ml goat-anti-AL488 (life technologies). % remaining CD20 is calculated as ((MFI unquenched−MFI quenched)/MFI unquenched)×100.

Example 5

Materials and Methods
ADCC Assay

ADCC assays with $_{51}$Cr-labeled target cells were performed as previously described.[22, 24] Briefly, PBMC and PMN isolated from healthy individuals (MiniDonorDienst UMC Utrecht) by Ficoll/Histopaque separation (GE Healthcare) were combined with 51Cr-labeled Daudi cells (effector-to-target ratio=100:1) and CD20 mAb in dilution. After 4 hours incubation at 37° C./5% CO2, the supernatant was harvested and counted in a liquid scintillation counter (MicroBeta; Perkin Elmer). Lysis was calculated using the following formula: % lysis=((counts of sample−minimum release)/(maximum release−minimum release))×100. Daudi cells with effector cells in culture medium or in medium supplemented with 5% Triton X-100 (Roche Diagnostics) were used to determine minimum and maximum release, respectively.

EL4-CD20 Lymphoma Model

C57BL/6 mice were purchased from Janvier (France) or bred in the facilities. 4-6 mice/group were injected intraperitoneally (i.p.) with 5×105 CellTraceViolet (10 µM, Invitrogen)-labeled EL4-CD20 cells. After 16 hours, mice were treated with mAb or PBS (100 µl injected i.p. A peritoneal lavage with PBS containing 5 mM EDTA was performed after 24 hours and the amount of remaining tumor cells was determined using TruCount tubes (BD). All Experiments were Approved by the Animal Ethical Committee of the UMC Utrecht.

Saturation of CD20 on EL4-CD20 lymphoma cells

After performing the previously described EL-4 lymphoma model, collected tumor cells were washed twice with PBS and stained with secondary IgA or IgG-PE labelled antibody. Saturation of CD20 with anti-CD20 antibody was shown if no increased signal was present after adding antibody (10 µg/ml) ex vivo to the cells before staining with secondary antibody. Shaving of CD20 was determined by comparing CD20 expression on EL4 cells from PBS treated mice against antibody treated mice.

Figure 13:
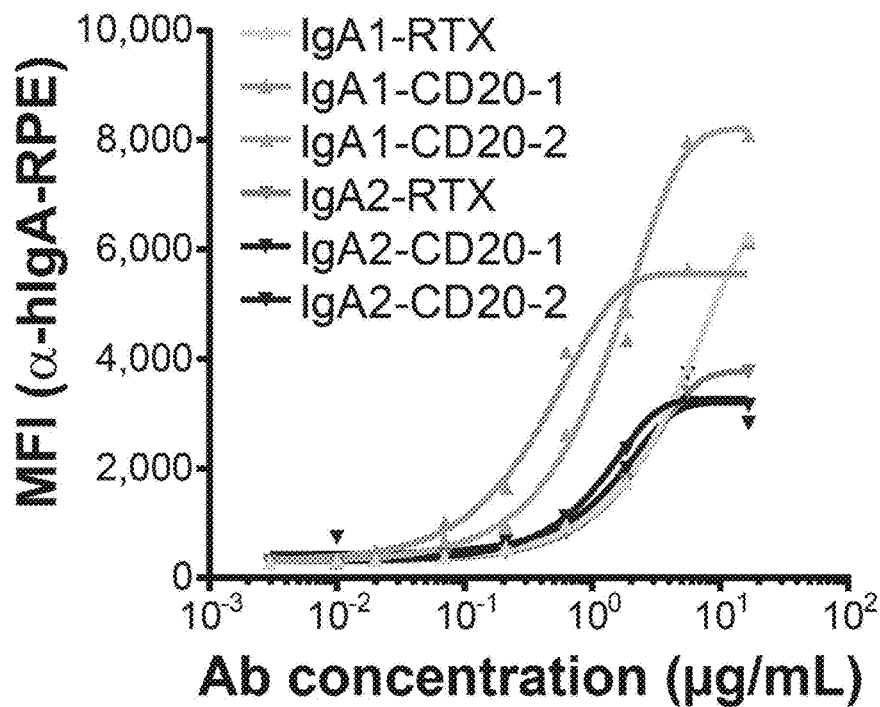
FIG. 13: Binding of IgA-CD20 mAbs to CD20-expressing Ramos cells. Binding was determined by FACS after incubation of Ramos cells with a dilution series of mAb.

Results
Functional Characterization:

The ability of the antibodies to bind to CD20-expressing Ramos cells and the functionality of the antibodies on PCD are depicted in FIG. 13 and FIG. 14. The ability of IgG1- and IgA-CD20 mAbs to induce CDC is depicted in FIGS. 15A-15C (see also Example 3). The ability of the new IgA-CD20 mAbs to induce PMN-mediated tumor cell lysis in a chromium release assay is depicted in FIGS. 27A, 27B. IgA1 antibodies do have similar ADCC potential, but IgA1-CD20 UMAB007 is the most effective (FIG. 27A). For IgA2 antibodies, all antibodies show a similar effectivity, but IgA2-CD20 UMAB010 has the highest killing potential (FIG. 27B). Next, the ability of the IgA-CD20 mAbs to deplete human B cells was analyzed. Incubation of leukocytes from healthy donors with the mAbs resulted in a concentration-dependent decline of CD19+ events (FIG. 16A). This effect was comparable between RTX and the IgA-CD20 mAbs. The number of CD19+ events (FIG. 16B) steadily decreased for all IgA-CD20 mAbs and reached a plateau between 0.05 and 0.5 µg/mL mAbs. In contrast, the number of CD19+ events upon RTX incubation reached a minimum at 0.05 µg/mL, but increased 5 at higher concentrations again. For both isotypes, the number of CD19− events reached an optimum between 0.05 to 0.5 µg/mL (FIG. 16C). The in vivo efficacy of a selection of these antibodies was studied in the EL4-CD20 lymphoma model (FIGS. 28A-28C). IgA2-CD20 UMAB002 and IgA1-CD20 UMAB007 were as potent as rituximab, which shows the potential of IgA antibodies in vivo. Finally, it was shown that loss of CD20 expression was seen after treatment with rituximab (FIG. 28A), but that expression is not lowered after treatment with IgA antibodies (FIGS. 28B, 28C). Next the CD20 expression of the EL4-CD20 cells was determined in the samples. It is shown that CD20 expression is lost after IgG treatment, but not after IgA treatment in vivo (FIG. 29). Umab 002 and 007 seem to perform better than umab 001 in this particular assay. IgA2 appears to be the better isotype for umab 001 and umab 002, while IgA1 is better in combination with umab 007. IgA1-CD20 UMAB . . . where the dots indicate three digits is an antibody with the indicated constant region and a variable domain of one of the five specified murine antibody. The last digit of the UMAB reference indicates the variable domain of the m antibody with the same digit.

TABLE 1

Panel of novel CD20 mIgG antibodies.

| mouse # | name | isotype | sequencing HC | sequencing LC | purified |
|---|---|---|---|---|---|
| 1 | m1 | IgG2c | x | x | x |
|  | m2 | IgG2c | x | x | x |
|  | m3 | IgG2b | x | x | x |
|  | m4 | IgG2b | x | x | x |
|  | m5 | IgG2b | x | x | x |
|  | m6 | IgG2b | x | x | x |
|  | m7 | IgG2b | x | x | x |
| 2 | m8 | IgG2b | x | x |  |
|  | m9 | IgG2c | x | x | x |
| 3 | m10 | IgG2c | x | x | x |
|  | m11 | IgG2b |  | x | x |
| 4 | m12 | unknown |  | x |  |
| 5 | m13 | IgG2c | x | x |  |
|  | m14 | IgG2c | x |  |  |
|  | m15 | IgG2c | x | x |  |
| 6 | m16 | IgG3 | x | x |  |
|  | m17 | IgG2b | x | x | x |

TABLE 2

| Name | Functionality in vitro CDC | ADCC | PCD |
|---|---|---|---|
| m1 (mIgG2c) | +++ | ++ | − |
| IgG1-CD20-1 | + | + | ++ |
| m2 (mIgG2c) | + | ++ | − |
| IgG1-CD20-2 | +/− | +++ | − |
| m7 (mIgG2b) | +++ | − | − |
| IgG1-CD20-7 | +++ | ++ | − |
| m9 (mIgG2c) | +++ | ++ | − |
| IgG1-CD20-9 | ++ | +++ | − |
| m10 (mIgG2c) | ++ | ++ | − |
| IgG1-CD20-10 | + | +++ | − |

TABLE 3

Affinity values of CD20 mAbs. Values were obtained by fitting a OneToOne binding model to the binding curves that had an association time of one hour and a dissociation time of three hours. The affinity ($K_D$) is obtained from the ratio between the dissociation rate constant ($k_{off}$) and the association rate constant ($k_{on}$).

| | non-competitive | | | competitive | | |
|---|---|---|---|---|---|---|
| | $k_{on}$ (1/M*s) | $k_{off}$ (1/s) | $K_D$ (nM) | $k_{on}$ (1/M*s) | $k_{off}$ (1/s) | $K_D$ (nM) |
| m1 | 3.73E+04 | 3.91E−05 | 1.05 | 2.61E+04 | 6.92E−05 | 2.65 |
| m2 | 8.54E+04 | 1.77E−05 | 0.21 | 8.17E+04 | 7.80E−05 | 0.96 |
| m9 | 4.57E+04 | 1.13E−05 | 0.25 | 5.39E+04 | 6.53E−06 | 0.12 |
| m10 | 4.42E+04 | 8.17E−06 | 0.19 | 5.57E+04 | 2.82E−05 | 0.51 |
| OFA | 5.01E+04 | 5.71E−06 | 0.11 | 7.70E+04 | 3.06E−05 | 0.40 |
| RTX | 5.14E+04 | 3.05E−05 | 0.59 | 7.35E+04 | 5.50E−05 | 0.75 |

CITED ART

Hallek M. et al. Addition of rituximab to fludarabine and cyclophosphamide in patients with chronic lymphocytic leukaemia: a randomised, open-label, phase 3 trial. Lancet 376:1164-1174 (2010).

2. Coiffier B. et al. Long-term outcome of patients in the LNH-98.5 trial, the first randomized study comparing rituximab-CHOP to standard CHOP chemotherapy in DLBCL patients: a study by the Groupe d'Etudes des Lymphomes de l'Adulte. Blood 116:2040-2045 (2010).

3. Keating G. M. Rituximab: a review of its use in chronic lymphocytic leukaemia, low-grade or follicular lymphoma and diffuse large B-cell lymphoma. Drugs 70:1445-1476 (2010).

4. Rastetter, W., A. Molina and C. A. White. Rituximab: expanding role in therapy for lymphomas and autoimmune diseases. Annu. Rev. Med. 55:477-503 (2004).

5. Badin, F. and J. Hayslip. Rituximab in the treatment of B-cell non-Hodgkin lymphoma, focus on outcomes and comparative effectiveness. Clinicoecon Outcomes Res. 2:37-45 (2010).

6. Sandhu, S. and S. P. Mulligan. Ofatumumab and its role as immunotherapy in chronic lymphocytic leukemia. Haematologica 100:411-414 (2015).

7. Laurenti L., I. Innocenti, F. Autore, S. Sica and D. G. Efremov. New developments in the management of chronic lymphocytic leukaemia: role of ofatumumab. Onco Targets Ther. 9:421-429 (2016).

8. Goede V. et al. Obinutuzumab plus chlorambucil in patients with CLL and coexisting conditions. N. Engl. J. Med. 370:1101-1110 (2014).

9. Sehn L. H. et al. GADOLIN: Primary results from a phase III study of obinutuzumab plus bendamustine compared with bendamustine alone in patients with rituximab-refractory indolent non-Hodgkin lymphoma. Journal of Clinical Oncology, 2015 ASCO Annual Meeting Vol 33, No 15 suppl (May 20 Supplement) (2015).

10. Cragg M. S. et al. Complement-mediated lysis by anti-CD20 mAb correlates with segregation into lipid rafts. Blood 101:1045-1052 (2003).

11. Chan H. T. et al. CD20-induced lymphoma cell death is independent of both caspases and its redistribution into triton X-100 insoluble membrane rafts. Cancer Res. 63:5480-5489 (2003).

12. Mossner E. et al. Increasing the efficacy of CD20 antibody therapy through the engineering of a new type II anti-CD20 antibody with enhanced direct and immune effector cell-mediated B-cell cytotoxicity. Blood 115: 4393-4402 (2010).

13. Beers S. A. et al. Type II (tositumomab) anti-CD20 monoclonal antibody out performs type I (rituximab-like) reagents in B-cell depletion regardless of complement activation. Blood 112:4170-4177 (2008).

14. Teeling J. L. et al. Characterization of new human CD20 monoclonal antibodies with potent cytolytic activity against non-Hodgkin lymphomas. Blood 104:1793-1800 (2004).

15. Stanglmaier M., S. Reis and M. Hallek. Rituximab and alemtuzumab induce a nonclassic, caspase-independent apoptotic pathway in B-lymphoid cell lines and in chronic lymphocytic leukemia cells. Ann. Hematol. 83:634-645 (2004).

16. Bornstein G. G. et al. Development of a new fully human anti-CD20 monoclonal antibody for the treatment of B-cell malignancies. Invest. New Drugs 28:561-574 (2010).

17. Du J. et al. Structural basis for recognition of CD20 by therapeutic antibody Rituximab. J. Biol. Chem. 282: 15073-15080 (2007).

18. Niederfellner G. et al. Epitope characterization and crystal structure of GA101 provide insights into the molecular basis for type I/II distinction of CD20 antibodies. Blood 118:358-367 (2011).

19. Polyak M. J. and J. P. Deans. Alanine-170 and proline-172 are critical determinants for extracellular CD20 epitopes; heterogeneity in the fine specificity of CD20 monoclonal antibodies is defined by additional requirements imposed by both amino acid sequence and quaternary structure. Blood 99:3256-3262 (2002).

20. Teeling J. L. et al. The biological activity of human CD20 monoclonal antibodies is linked to unique epitopes on CD20. J. Immunol. 177:362-371 (2006).

21. Goldenberg D. M., F. Morschhauser and W. A Wegene. Veltuzumab (humanized anti-CD20 monoclonal antibody): characterization, current clinical results, and future prospects. Leuk. Lymphoma 51:747-755 (2010).

22. Meyer S. et al. Improved in vivo anti-tumor effects of IgA-Her2 antibodies through half-life extension and serum exposure enhancement by FcRn targeting. MAbs 8:87-98 (2016).

23. DiGaetano N. et al. Complement activation determines the therapeutic activity of rituximab in vivo. J. Immunol. 171:1581-1587 (2003).

24. Congdon E. E., J. Gu, H. B. R. Sait and E. M. Sigurdsson. Antibody Uptake into Neurons Occurs Primarily via Clathrin-dependent Fcγ Receptor Endocytosis and Is a Prerequisite for Acute Tau Protein Clearance*. J. Biol. Chem. 288:35452-35465 (2013).

25. Slootstra J. W., W. C. Puijk, G. J. Ligtvoet, J. P. Langeveld and R. H. Meloen, Structural aspects of antibody-antigen interaction revealed through small random peptide libraries. Mol. Divers. 1:87-96 (1996).

26. Timmerman P., J. Beld, W. C. Puijk, and R. H. Meloen. Rapid and quantitative cyclization of multiple peptide loops onto synthetic scaffolds for structural mimicry of protein surfaces. Chembiochem. 6:821-824 (2005).

27. Boross P. et al. The in vivo mechanism of action of CD20 monoclonal antibodies depends on local tumor burden. Haematologica 96:1822-1830 (2011).

28. Esser C. and A. Radbruch. Immunoglobulin class switching: molecular and cellular analysis. Annu. Rev. Immunol. 8:717-735 (1990).

29. Klein C. et al. Epitope interactions of monoclonal antibodies targeting CD20 and their relationship to functional properties. MAbs 5:22-33 (2013).
30. Umana P. et al. Novel 3rd Generation Humanized Type II CD20 Antibody with Glycoengineered Fc and Modified Elbow Hinge for Enhanced ADCC and Superior Apoptosis Induction. 11:108 (2006).
31. Withoff S. et al. Characterization of BIS20x3, a bi-specific antibody activating and retargeting T-cells to CD20-positive B-cells. Br. J. Cancer 84:1115-1121 (2001).
32. Goldenberg D. M. et al. Properties and structure-function relationships of veltuzumab (hA20), a humanized anti-CD20 monoclonal antibody. Blood 113:1062-1070 (2009).
33. Li B. et al. Characterization of a rituximab variant with potent antitumor activity against rituximab-resistant B-cell lymphoma. Blood 114:5007-5015 (2009).
34. Diebolder C. A. et al. Complement is activated by IgG hexamers assembled at the cell surface. Science 343: 1260-1263 (2014).
35. de Jong R. N. et al. A Novel Platform for the Potentiation of Therapeutic Antibodies Based on Antigen-Dependent Formation of IgG Hexamers at the Cell Surface. PLoS Biol. 14, e1002344 (2016).
36. Senior B W, J M Woof. The influences of hinge length and composition on the susceptibility of human IgA to cleavage by diverse bacterial IgA1 proteases. *J Immunol* 2005; 174: 7792-9.
37. Bakema J E, M van Egmond. Immunoglobulin A: A next generation of therapeutic antibodies? *MAbs* 2011; 3: 352-61.
38. Roos A, L H Bouwman, D J van Gijlswijk-Janssen, M C Faber-Krol, G L Stahl, M R Daha. Human IgA activates the complement system via the mannan-binding lectin pathway. *J Immunol* 2001; 167: 2861-8.
39. Otten M A, M van Egmond. The Fc receptor for IgA (FcalphaRI, CD89). *Immunol Lett* 2004; 92: 23-31.
40. Geissmann F, P Launay, B Pasquier, Y Lepelletier, M Leborgne, Lehuen A, et al. A subset of human dendritic cells expresses IgA Fc receptor (CD89), which mediates internalization and activation upon cross-linking by IgA complexes. *J Immunol* 2001; 166: 346-52.
41. Heystek H C, C Moulon, A M Woltman, P Garonne, C van Kooten. Human immature dendritic cells efficiently bind and take up secretory IgA without the induction of maturation. *J Immunol* 2002; 168: 102-7.
42. Hamre R, I N Farstad, P Brandtzaeg, H C Morton. Expression and modulation of the human immunoglobulin A Fc receptor (CD89) and the FcR gamma chain on myeloid cells in blood and tissue. *Scand J Immunol* 2003; 57: 506-16.
43. Lohse S, C Brunke, S Derer, M Peipp, C Boross, C Kellner, et al. Characterization of a mutated IgA2 antibody of the m(1) allotype against the epidermal growth factor receptor for the recruitment of monocytes and macrophages. *J Biol Chem* 2012; 287: 25139-50.
44. Boross P, S Lohse, M Nederend, J H Jansen, G van Tetering, M Dechant, et al. IgA EGFR antibodies mediate tumour killing in vivo. *EMBO Mol Med* 2013; 5: 1213-26.
45. Meyer S, M Nederend, J H Jansen, K R Reiding, S R Jacobino, J Meeldijk, et al. Improved in vivo anti-tumor effects of IgA-Her2 antibodies through half-life extension and serum exposure enhancement by FcRn targeting. *MAbs* 2016; 8: 87-98.
46. Rouwendal G J A, M M van der Lee, S Meyer, K R Reiding, J Schouten, G de Roo, et al. A comparison of anti-HER2 IgA and IgG1 in vivo efficacy is facilitated by high N-glycan sialylation of the IgA. *mAbs* 2016.
47. R A Clynes, T L Towers, L G Presta, J V Ravetch. Inhibitory Fc receptors modulate in vivo cytotoxicity against tumor targets. *Nat Med* 2000; 6: 443-6.
48. van Egmond M, A J van Vuuren, H C Morton, A B van Spriel, L Shen, F M Hofhuis, et al. Human immunoglobulin A receptor (FcalphaRI, CD89) function in transgenic mice requires both FcR gamma chain and CR3 (CD11b/CD18). *Blood* 1999; 93: 4387-94.
49. Pascal V, B Laffleur, A Debin, A Cuvillier, M van Egmond, D Drocourt, et al. Anti-CD20 IgA can protect mice against lymphoma development: evaluation of the direct impact of IgA and cytotoxic effector recruitment on CD20 target cells. *Haematologica* 2012; 97: 1686-94.
50. Bologna L, E Gotti, M Manganini, A Rambaldi, T Intermesoli, M Introna, et al. Mechanism of action of type II, glycoengineered, anti-CD20 monoclonal antibody GA101 in B-chronic lymphocytic leukemia whole blood assays in comparison with rituximab and alemtuzumab. J Immunol 2011; 186: 3762-9.
51. Bologna L, E Gotti, R F Da, T Intermesoli, A Rambaldi, M Introna, et al. Ofatumumab is more efficient than rituximab in lysing B chronic lymphocytic leukemia cells in whole blood and in combination with chemotherapy. J Immunol 2013; 190: 231-9.
52. Jones J D, B J Hamilton, W F Rigby. Rituximab mediates loss of CD19 on B cells in the absence of cell death. Arthritis Rheum 2012; 64: 3111-8.
53. Homer H, C Frank, C Dechant, R Repp, M Glennie, M Herrmann, et al. Intimate cell conjugate formation and exchange of membrane lipids precede apoptosis induction in target cells during antibody-dependent, granulocyte-mediated cytotoxicity. J Immunol 2007; 179: 337-45.
54. Zhao W. Targeting CD47-SIRPa interactions for potentiating therapeutic antibody-mediated tumor cell destruction by phagocytes. 2014.
55. Beum P V, E M Peek, M A Lindorfer, F J Beurskens, P J Engelberts, P W Parren, et al. Loss of CD20 and bound CD20 antibody from opsonized B cells occurs more rapidly because of trogocytosis-mediated by Fc receptor-expressing effector cells than direct internalization by the B cells. J Immunol 2011; 187: 3438-47.
56. Glennie M J, R R French, M S Cragg, R P Taylor. Mechanisms of killing by anti-CD20 monoclonal antibodies. *Mol Immunol* 2007; 44: 3823-37.
57. Weiner G J. Rituximab: mechanism of action. *Semin Hematol* 2010; 47: 115-23.
58. Lim S H, S A Beers, R R French, P W Johnson, M J Glennie M J, M S Cragg. Anti-CD20 monoclonal antibodies: historical and future perspectives. *Haematologica* 2010; 95: 135-43.
59. Golay J, M Introna. Mechanism of action of therapeutic monoclonal antibodies: promises and pitfalls of in vitro and in vivo assays. *Arch Biochem Biophys* 2012; 526: 146-53.
60. Boross P, J H Leusen. Mechanisms of action of CD20 antibodies. *Am J Cancer Res* 2012; 2: 676-90.
61. Okroj M, A Osterborg, A M Blom. Effector mechanisms of anti-CD20 monoclonal antibodies in B cell malignancies. *Cancer Treat Rev* 2013; 39: 632-9.
62. Abes R, E Gelize, W H Fridman, J L Teillaud. Long-lasting antitumor protection by anti-CD20 antibody through cellular immune response. *Blood* 2010; 116: 926-34.

63. Weiner L M, M V Dhodapkar, S Ferrone. Monoclonal antibodies for cancer immunotherapy. *Lancet* 2009; 373: 1033-40.
64. Rafiq K, A Bergtold, R Clynes. Immune complex-mediated antigen presentation induces tumor immunity. *J Clin Invest* 2002; 110: 71-9.
65. Paiva M, H Marques, A Martins, P Ferreira, R Catarino, R Medeiros. FcgammaRlla polymorphism and clinical response to rituximab in non-Hodgkin lymphoma patients. *Cancer Genet Cytogenet* 2008; 183: 35-40.
66. Zhang W, M Gordon, A M Schultheis, D Y Yang, F Nagashima, M Azuma, et al. FCGR2A and FCGR3A polymorphisms associated with clinical outcome of epidermal growth factor receptor expressing metastatic colorectal cancer patients treated with single-agent cetuximab. *J Clin Oncol* 2007; 25: 3712-8.
67. Musolino A, N Naldi, B Bortesi, D Pezzuolo, M Capelletti, G Missale, et al. Immunoglobulin G fragment C receptor polymorphisms and clinical efficacy of trastuzumab-based therapy in patients with HER-2/neu-positive metastatic breast cancer. *J Clin Oncol* 2008; 26: 1789-96.
68. Dall'Ozzo S, S Tartas, G Paintaud, G Cartron, P Colombat, P Bardos, et al. Rituximab-dependent cytotoxicity by natural killer cells: influence of FCGR3A polymorphism on the concentration-effect relationship. *Cancer Res* 2004; 64: 4664-9.
69. Rezvani A R, D G Maloney. Rituximab resistance. *Best Pract Res Clin Haematol* 2011; 24: 203-16.
70. Small G W, H L McLeod, K L Richards. Analysis of innate and acquired resistance to anti-CD20 antibodies in malignant and nonmalignant B cells. *Peer J* 2013; 1: e31.
71. McLaughlin P, A J Grillo-Lopez, B K Link, R Levy, M S Czuczman, M E Williams, et al. Rituximab chimeric anti-CD20 monoclonal antibody therapy for relapsed indolent lymphoma: half of patients respond to a four-dose treatment program. *J Clin Oncol* 1998; 16: 2825-33.
72. Davis T A, A J Grillo-Lopez, C A White, P McLaughlin, M S Czuczman, B K Link, et al. Rituximab anti-CD20 monoclonal antibody therapy in non-Hodgkin's lymphoma: safety and efficacy of re-treatment. *J Clin Oncol* 2000; 18: 3135-43.
73. Kiss F, J Buslig, I Szegedi, B Scholtz, J Kappelmayer, C Kiss. Early relapse after rituximab chemoimmunotherapy. *Pediatr Blood Cancer* 2008; 50: 372-5.
74. Dechant M, T Beyer, T Schneider-Merck, W Weisner, M Peipp, J G van de Winkel, et al. Effector mechanisms of recombinant IgA antibodies against epidermal growth factor receptor. J Immunol 2007; 179: 2936-43.
75. Kocsis A, K A Kekesi, R Szasz, B M Vegh, J Balczer, J Dobo, et al. Selective inhibition of the lectin pathway of complement with phage display selected peptides against mannose-binding lectin-associated serine protease (MASP)-1 and -2: significant contribution of MASP-1 to lectin pathway activation. J Immunol 2010; 185: 4169-78.
76. Dunkelberger J R, W C Song. Complement and its role in innate and adaptive immune responses. Cell Res 2010; 20: 34-50.
77. Tipton T R, A Roghanian, R J Oldham, M J Carter, K L Cox, C I Mockridge, R R French, L N Dahal, P J Duriez, P G Hargreaves, M S Cragg, S A Beers. Blood. 2015 Mar. 19; 125(12):1901-9. doi: 10.1182/blood-2014-07-588376. Epub 2015 Jan. 28, Inhibitory FcγRIIb (CD32b) becomes activated by therapeutic mAb in both cis and trans and drives internalization according to antibody specificity.
78. Vaughan A T, C Iriyama, S A Beers, C H Chan, S H Lim, E L Williams, V Shah, A Roghanian, B Frendéus, M J Glennie, M S Cragg. Blood. 2014 Jan. 30; 123(5):669-77. doi: 10.1182/blood-2013-04-490821. Epub 2013 Nov. 13. Fc gamma receptor IIb on target B cells promotes rituximab internalization and reduces clinical efficacy.
79. Lim S H, A T Vaughan, M Ashton-Key, E L Williams, S V Dixon, H T Chan, S A Beers, R R French, K L Cox, A J Davies, K N Potter, C I Mockridge, D G Oscier, P W Johnson, M S Cragg, M J Glennie. Blood. 2011 Sep. 1; 118(9):2530-40. doi: 10.1182/blood-2011-01-330357. Epub 2011 Jul. 18, Antigenic modulation limits the effector cell mechanisms employed by type I anti-CD20 monoclonal antibodies.

What is claimed is:

1. An isolated antibody that can bind to an extracellular part of human CD20 expressed on Ramos cells, the antibody comprising:
a variable domain with
a heavy chain variable region, and
a light chain variable region,
wherein the heavy chain variable region comprises a CDR1, CDR2 and CDR3 region with the sequence SYNLH (SEQ ID NO:26), ATYPGNGDTSYNQKFKG (SEQ ID NO: 27), and SNSYGSTYWYFDV (SEQ ID NO: 21), respectively, and
wherein the light chain variable region comprises a CDR1, CDR2 and CDR3 region with the sequence RARSSVSYMD (SEQ ID NO: 31), ATSNLAS (SEQ ID NO: 32), and QOQWTSNPPT (SEQ. ID NO: 33), respectively.

2. The antibody of claim 1, wherein the heavy chain variable region comprises the sequence of SEQ ID NO: 1, with 0-5 amino acid insertions, deletions, substitutions, additions or a combination thereof at one or more positions other than positions of the amino acids that constitute the CDR1, CDR2 and CDR3 regions.

3. The antibody of claim 1, wherein the light chain variable region comprises the sequence of SEQ ID NO:2, with 0-5 amino acid insertions, deletions, substitutions, additions or a combination thereof at one or more positions other than positions of the amino acids that constitute the CDR1, CDR2 and CDR3 regions.

4. An isolated antibody comprising:
a heavy chain that comprises the sequence of SEQ ID NO: 1 and the sequences of SEQ ID NO:3, SEQ ID NO:4 or SEQ ID NO:5, and
a light chain that comprises the sequence of SEQ ID NO:2 and the sequence of SEQ ID NO:6;
wherein the antibody has an increased Complement-Dependent Cytotoxicity ("CDC") and/or increased antibody-dependent cellular cytotoxicity ("ADCC") functionality when compared to Rituximab with a constant region of the same isotype.

5. The antibody of claim 1, comprising a mouse IgG2; a human IgG1, human IgG2, human IgG3, human IgG4, human IgM, human IgE, human IgA heavy chain constant region or a combination thereof.

6. The antibody of claim 5, comprising a human IgG1, human IgG2, human IgA1 or human IgA2 heavy chain constant region or a combination thereof.

7. The antibody of claim 1, comprising a heavy chain and a light chain, wherein the heavy chain comprises the sequence of SEQ ID NO: 1 and the sequence of SEQ ID NO:3, SEQ ID NO:4 or SEQ ID NO:5 with 0-15 amino acid insertions, deletions, substitutions, additions or a combination thereof at one or more positions other than positions of the amino acids that constitute the CDR1, CDR2 and CDR3 regions.

8. The antibody of claim 1, wherein the light chain comprises the sequence of SEQ ID NO:2 and the sequence of SEQ ID NO:6 with 0-15 amino acid insertions, deletions, substitutions, additions or a combination thereof at one or more positions other than positions of the amino acids that constitute the CDR1, CDR2 and CDR3 regions.

9. The antibody of claim 1, wherein the antibody has an increased programmed cell death ("PCD") functionality when compared to Rituximab with a constant region of the same isotype.

10. The antibody of claim 1, wherein the heavy chain comprises the sequence of SEQ ID NO: 1 and the sequence of SEQ ID NO:3, SEQ ID NO:4 or SEQ ID NO:5.

11. The antibody of claim 1, wherein the light chain comprises the sequence of SEQ ID NO:2 and the sequence of SEQ ID NO:6.

\* \* \* \* \*